(12) United States Patent
Schoentjes et al.

(10) Patent No.: US 8,541,442 B2
(45) Date of Patent: Sep. 24, 2013

(54) INDOLE DERIVATIVES AS ANTICANCER AGENTS

(75) Inventors: Bruno Schoentjes, Brussels (BE); Sophie Descamps, Belbeuf (FR); Nathalie Claudie Isabelle Amblard, Amfreville la Campagne (FR)

(73) Assignee: Janssen Pharmaceutica N.V., Beerse (BE)

( * ) Notice: Subject to any disclaimer, the term of this patent is extended or adjusted under 35 U.S.C. 154(b) by 253 days.

(21) Appl. No.: 13/147,707

(22) PCT Filed: Feb. 3, 2010

(86) PCT No.: PCT/EP2010/051316
§ 371 (c)(1), (2), (4) Date: Aug. 3, 2011

(87) PCT Pub. No.: WO2010/089327
PCT Pub. Date: Aug. 12, 2010

(65) Prior Publication Data
US 2011/0294846 A1 Dec. 1, 2011

(30) Foreign Application Priority Data
Feb. 4, 2009 (EP) .................................. 09152089

(51) Int. Cl.
A61K 31/435 (2006.01)
A61K 31/4439 (2006.01)
A61P 35/00 (2006.01)
C07D 401/12 (2006.01)

(52) U.S. Cl.
USPC ......... 514/299; 514/339; 546/112; 546/277.4

(58) Field of Classification Search
USPC ....................... 514/299, 339; 546/112, 277.4
See application file for complete search history.

(56) References Cited

FOREIGN PATENT DOCUMENTS

| EP | 1317443 B1 | 6/2003 |
|---|---|---|
| EP | 1379239 B1 | 1/2004 |
| EP | 1443937 B1 | 8/2004 |
| EP | 1458380 B1 | 9/2004 |
| EP | 1519932 B1 | 4/2005 |
| EP | 1809622 B1 | 7/2007 |
| JP | 11130750 A | 5/1999 |
| WO | WO 00/15357 A2 | 3/2000 |
| WO | WO 00/27819 A2 | 5/2000 |
| WO | WO 00/32175 A2 | 6/2000 |
| WO | WO 01/42224 A1 | 6/2001 |
| WO | WO 02/078693 A2 | 10/2002 |
| WO | WO 03/040402 A2 | 5/2003 |
| WO | 2006032631 * | 3/2006 |
| WO | WO 2006/032631 A1 | 3/2006 |
| WO | WO 2007/107543 A1 | 9/2007 |
| WO | WO 2007/107545 A1 | 9/2007 |
| WO | WO 2009/019274 A1 | 2/2009 |
| WO | WO 2009/037308 A1 | 3/2009 |
| WO | WO 2009/037343 A1 | 3/2009 |

OTHER PUBLICATIONS

Bissery, MC, et al., "Historique et récents développements des méthods de criblage et d'évaluation des molécules anticancéreuses in vitro et in vivo", Bull Cancer (1991), vol. 78, pp. 587-602.
Colpaert, F.C., et al., "A Critical Study on RO-4-1284 Antagonism in Mice", Arch. Int. Pharmacodyn (1975), vol. 215, pp. 40-90.
Colzi, A., et al., "Monoamine Oxidase-A Inhibitors and Dopamine Metabolism in Rat Caudatus: Evidence That an Increased Cyosolic Level of Dopamine Displaces Reversible Monoamine Oxidase-A Inhibitors in Vivo", Journal of Pharmacology and Experimental Therapeutics (1993), vol. 265, No. 1, pp. 103-111.
Crespi, C.L., et al., "Microtiter Plate Assays for Inhibition of Human, Drug-Metabolizing Cytochromes P450", Analytical Biochemistry (1997), vol. 248, pp. 188-190.
Filinger, E.J., "Effect of a Reserpine-like Agent on the Release and Metabolism of [3H]NA in Cell Bodies and Terminals", Gen. Pharmac (1994), vol. 25, No. 5, pp. 1039-1043.
Finney, D. J., "Graded Response: The Linear Dosage-Response Curve", Probit Analysis, 2nd Edition, Chapter 10 (1962), Cambridge Publishing Press, 16 page article.
Verkade, P.E., et al., "IUPAC Tentative Rules for the Nomenclature of Organic Chemistry. Section E. Fundamental Stereochemistry", Journal of Organic Chemistry (1970), vol. 35, No. 9, pp. 2849-2867.
Workman, P., et al., "United Kingdom Co-ordinating Committee on Cancer Research (UKCCCR) Guidelines for the Welfare of Animals in Experimental Neoplasia (Second Edition)", British Journal of Cancer (1998), vol. 77, No. 1, pp. 1-10.
International Search Report PCT/EP2010/051316, mailed Aug. 31, 2010.

* cited by examiner

*Primary Examiner* — Niloofar Rahmani
(74) *Attorney, Agent, or Firm* — Rajiv S. Shah

(57) ABSTRACT

The present invention provides compounds of formula (I), their use for the treatment of cancer as well as pharmaceutical compositions comprising said compounds of formula (I).

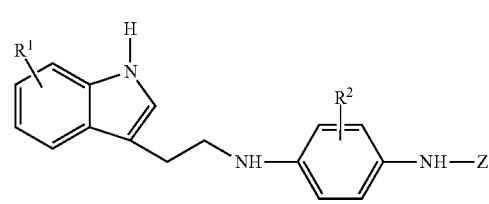

14 Claims, No Drawings

INDOLE DERIVATIVES AS ANTICANCER AGENTS

CROSS REFERENCE TO RELATED APPLICATIONS

This application is a national stage of PCT Application No. PCT/EP2010/051316, filed Feb. 3, 2010, which claims priority for EPO Patent Application No. 09152089.0, filed Feb. 4, 2009, all of which are hereby incorporated by reference in their entirety.

FIELD OF THE INVENTION

The present invention relates to indole compounds and compositions containing said compounds acting as anticancer agents. Moreover, the present invention provides processes for the preparation of the disclosed compounds, compositions comprising them and methods of using them, for instance as a medicine, in particular for the treatment of cancer.

The present application claims priority of European patent application No. 09152089.0, which is incorporated herein by reference. Without being bound to any theory, it is currently thought that although MDM2 and p53 represent key elements in tumor cell biology and have key roles in the cellular response to cell insult or stress and although the present compounds increase the expression of p53, it appears that they may not represent the primary molecular targets by which the present compounds elicit their demonstrated potent preclinical anti-tumor activity. Initial observations point at a direct or indirect effect on DNA synthesis and/or replicative-stress response as support for the observed preclinical anti-tumor activity of the compounds. The present compounds also exhibit anti-proliferative effects in tumour cells that are devoid of p53, devoid of functional p53, or having mutant p53, and furthermore they can sensitise tumorigenic cells for chemotherapy and radiotherapy.

p53 is a tumour suppressor protein which plays a pivotal role in the regulation of the balance between cell proliferation and cell growth arrest/apoptosis. Under normal conditions the half life of p53 is very short and consequently the level of p53 in cells is low. However, in response to cellular DNA damage or cellular stress (e.g. oncogene activation, telomere erosion, hypoxia), levels of p53 increase. This increase in p53 levels leads to the activation of the transcription of a number of genes which drives the cell into either growth arrest or into the processes of apoptosis. Thus, an important function of p53 is to prevent the uncontrolled proliferation of damaged cells and thus protect the organism from the development of cancer. The term "MDM2" (Murine Double Minute2) is used herein to mean a protein obtained as a result of expression of the mdm2 gene. Within the meaning of this term, MDM2 encompass all proteins encoded by mdm2, mutants thereof, alternative slice proteins thereof, and phosphorylated proteins thereof. Additionally, as used herein, the term "MDM2" includes MDM2 analogues, e.g. MDMX, also known as MDM4, and MDM2 homologues and analogues of other animals, e.g. the human homologue HDM2 or the human analogue HDMX. MDM2 is a key negative regulator of p53 function. It forms a negative autoregulatory loop by binding to the amino terminal transactivation domain of p53 and thus MDM2 both inhibits the ability of p53 to activate transcription and targets p53 for proteolytic degradation. Under normal conditions this regulatory loop is responsible for maintaining the low levels of p53.

BACKGROUND OF THE INVENTION

JP 11130750 describes amongst others, substituted phenylaminocarbonylindolyl derivatives as 5-HT receptor antagonists.

EP1129074 describes anthranilic acid amides as inhibitors of vascular endothelial growth factor receptors (VEGFR) and useful in the treatment of angiogenic disorders. WO01/42224 provides carboxyamido derivatives for the treatment of Alzheimer disease. EP1317443 discloses tricyclic tert-amine derivatives, useful as chemokine receptor CXCR4 or CCR5 modulators for treating human immunodeficiency virus and feline immunodeficiency virus.

EP1379239 discloses N-(2-arylethyl)benzylamines as antagonists of the 5-HT$_6$ receptor. WO00/15357 provides piperazine-4-phenyl derivatives as inhibitors of the interaction between MDM2 and p53. EP1137418 provides tricyclic compounds for restoring conformational stability of a protein of the p53 family. WO03/040402 provides compounds that inhibit the interactions between proteins, such as the interaction between MDM2 and p53. EP1443937 describes substituted 1,4-benzodiazepines and the uses thereof as inhibitors of the MDM2-p53 interactions. EP1458380 provides cis-2,4,5-triphenyl-imidazolones that inhibit the interaction of MDM2 protein with p53-like peptides and have antiproliferative activity.

EP1519932 discloses bisarylsulfonamide compounds that bind to MDM2 and can be used in cancer therapy.

WO2006/032631, WO2007/107543, WO2007/107545, WO2009/019274, WO2009/037308 and WO2009/037343 disclose inhibitors of the interaction between MDM2 and p53.

There is a need for effective small molecules that have potent inhibitory effect against tumor cell growth, have a broad safety profile, and less undesired side effects.

The compounds of the present invention show excellent in-vitro activity and excellent in vivo anti tumor effects. They have low affinity for the P450 enzymes which reduces the risk of adverse drug-drug interaction allowing for a wider safety margin. Moreover, the compounds of the present invention have low drug induced neurological effects and have an improved cardiovascular profile which may favorably influence the dose limiting toxicity of the compounds.

DESCRIPTION OF THE INVENTION

The present invention provides compounds, compositions for, and methods of treating cancer. Furthermore the compounds and compositions of the present invention are useful in enhancing the effectiveness of chemotherapy and radiotherapy.

This invention concerns compounds of formula (I)

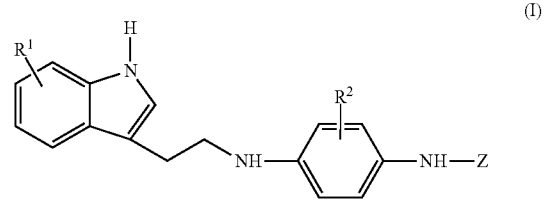

including any stereochemically isomeric form thereof, wherein $R^1$ is hydroxyC$_{1-6}$alkyl or C$_{2-6}$alkenyl; provided that the $R^1$ substituent is placed in position 6 or 7 of the indole moiety;
$R^2$ is hydrogen or C$_{1-4}$alkyl;
Z is a radical selected from

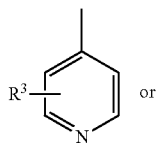

(z-1)

or

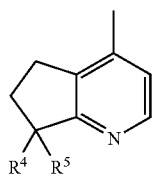

(z-2)

$R^3$ is hydrogen or hydroxyC$_{1-4}$alkyl;
$R^4$ is hydroxy or C$_{1-4}$alkyloxy;
$R^5$ is hydrogen or C$_{1-4}$alkyl; or
$R^4$ and $R^5$ are taken together to form oxo;
a pharmaceutically acceptable salt thereof or a solvate thereof.

The compounds of formula (I) may also exist in their tautomeric forms. Such forms although not explicitly indicated in the above formula are intended to be included within the scope of the present invention.

The present invention also relates to the use of a compound of formula (I) for the manufacture of a medicament for treating cancer and to a compound of formula (I) for use in the treatment of cancer.

A number of terms used in the foregoing definitions and hereinafter are explained hereunder. These terms are sometimes used as such or in composite terms.

C$_{1-4}$alkyl as a group or part of a group defines straight or branched chain saturated hydrocarbon radicals having from 1 to 4 carbon atoms such as methyl, ethyl, propyl, 1-methylethyl, butyl; C$_{1-6}$alkyl as a group or part of a group defines straight or branched chain saturated hydrocarbon radicals having from 1 to 6 carbon atoms such as the group defined for C$_{1-4}$alkyl and pentyl, hexyl, 2-methylbutyl and the like. C$_{2-6}$alkenyl defines straight and branched chain hydrocarbon radicals containing a double bond and having from 2 to 6 carbon atoms such as, for example, ethenyl, 2-propenyl, 3-butenyl, 2-pentenyl, 3-pentenyl, 3-methyl-2-butenyl, and the like.

Lines drawn from substituents into ring systems indicate that the bond may be attached to any of the suitable ring atoms.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable salts as mentioned hereinbefore or hereinafter are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfonic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. The pharmaceutically acceptable salts as mentioned hereinbefore or hereinafter are meant to also comprise the therapeutically active non-toxic metal or amine addition salt forms (base addition salt forms) which the compounds of formula (I) are able to form. Appropriate base addition salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like.

Conversely the salt form can be converted by treatment with acid into the free acid form.

The term salt also comprises the quaternary ammonium salts (quaternary amines) which the compounds of formula (I) are able to form by reaction between a basic nitrogen of a compound of formula (I) and an appropriate quaternizing agent, such as, for example, an optionally substituted C$_{1-6}$alkylhalide, arylhalide, C$_{1-6}$alkylcarbonylhalide, arylcarbonylhalide, or arylC$_{1-6}$alkylhalide, e.g. methyliodide or benzyliodide, wherein aryl represents unsubstituted or substituted phenyl. Other reactants with good leaving groups may also be used, such as for example C$_{1-6}$alkyl trifluoromethanesulfonates, C$_{1-6}$alkyl methanesulfonates, and C$_{1-6}$alkyl p-toluenesulfonates. A quaternary amine has a positively charged nitrogen.

Pharmaceutically acceptable counterions include chloro, bromo, iodo, trifluoroacetate, acetate, triflate, sulfate, sulfonate. The counterion of choice can be introduced using ion exchange resins.

Preferably, the term salt means the pharmaceutically acceptable acid addition salt forms and the pharmaceutically acceptable metal or amine addition salt forms.

The term solvate comprises the hydrates and solvent addition forms which the compounds of formula (I) are able to form, as well as the salts thereof. Examples of such forms are e.g. hydrates, alcoholates and the like.

It will be appreciated that some of the compounds of formula (I) and their salts, and solvates may contain one or more centers of chirality and exist as stereochemically isomeric forms.

The term "stereochemically isomeric forms of compounds of formula (I)", as used hereinbefore, defines all possible compounds made up of the same atoms bonded by the same sequence of bonds but having different three-dimensional structures which are not interchangeable, which the compounds of formula (I) and their pharmaceutically acceptable salts or physiologically functional derivatives may possess.

Unless otherwise mentioned or indicated, the chemical designation of compounds denotes the mixture of all possible stereochemically isomeric forms, as well as each of the individual isomeric forms of formula (I) and their salts or solvates, substantially free, i.e. associated with less than 50%, preferably less than 20%, more preferably less than 10%, even more preferably less than 5%, further preferably less than 2% and most preferably less than 1% of the other isomer(s). Thus, when a compound of formula (I) is for instance specified as R, this means that the compound is substantially free of the S isomer. Or if a compound of formula (I) is for instance specified as E, this means that the compound is substantially free of the Z isomer.

In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (I) are obviously intended to be embraced within the scope of this invention.

Of special interest are those compounds of formula (I) which are stereochemically pure.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S-[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

The terms cis and trans when used herein are in accordance with Chemical Abstracts nomenclature (J. Org. Chem. 1970, 35 (9), 2849-2867), and refer to the position of the substituents on a ring moiety.

The compounds of (I) may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The present invention is also intended to include any isotopes of atoms present in the compounds of the invention. For example, isotopes of hydrogen include tritium and deuterium and isotopes of carbon include C-13 and C-14.

Whenever used hereinafter, the term "compounds of formula (I)" or "compounds of the present invention" is meant to include also the pharmaceutically acceptable salts, in particular the acid or base (metal or amine) addition salts, all stereoisomeric forms, the solvates, and all polymorphic crystalline forms or amorphous forms.

Whenever used hereinbefore or hereinafter that substituents can be selected each independently out of a list of numerous definitions, all possible combinations are intended which are chemically possible.

An interesting embodiment of the present invention are those compounds of formula (I) wherein the $R^1$ substituent is placed in position 7 of the indole moiety. Hence, compounds having the following formula

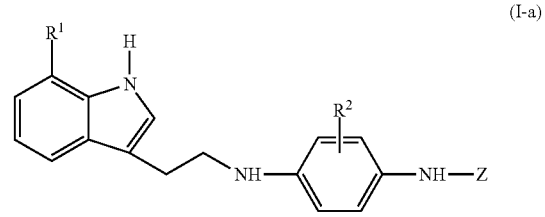

(I-a)

An interesting embodiment of the present invention are those compounds of formula (I) wherein the $R^1$ substituent is placed in position 6 of the indole moiety. Hence, compounds having the following formula

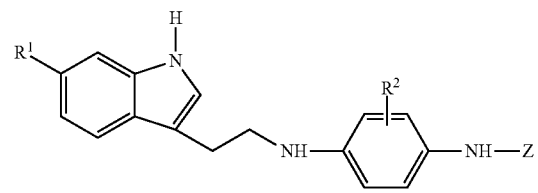

(I-b)

An interesting embodiment of the present invention are those compounds of formula (I), (I-a) or (I-b) wherein $R^1$ is hydroxyC$_{1-6}$alkyl, in particular —CH$_2$—OH, —C(CH$_3$)$_2$—OH, —CH(CH$_3$)—OH, —CH$_2$—CH$_2$—OH, —CH(CH(CH$_3$)$_2$)—OH, —CH$_2$—CH$_2$—CHOH—CH$_3$, more in particular —C(CH$_3$)$_2$—OH.

An interesting embodiment of the present invention are those compounds of formula (I), (I-a) or (I-b) wherein $R^1$ is C$_{2-6}$alkenyl, in particular —CH=CH$_2$, —C(CH$_3$)=CH$_2$.

An interesting embodiment of the present invention are those compounds of formula (I), (I-a) or (I-b) or an interesting embodiment thereof as indicated above, wherein $R^2$ is hydrogen.

An interesting embodiment of the present invention are those compounds of formula (I), (I-a) or (I-b) or, whenever possible, an interesting embodiment thereof as indicated above, wherein $R^2$ is $C_{1-4}$alkyl, in particular methyl.

An interesting embodiment of the present invention are those compounds of formula (I), (I-a) or (I-b) or, whenever possible, an interesting embodiment thereof as indicated above, wherein $R^3$ represents hydrogen.

An interesting embodiment of the present invention are those compounds of formula (I), (I-a) or (I-b) or, whenever possible, an interesting embodiment thereof as indicated above, wherein $R^3$ represent hydroxy$C_{1-4}$alkyl, in particular —$CH_2$—OH. Preferably this $R^3$ substituent is placed in position 2 of the pyridine moiety.

An interesting embodiment of the present invention are those compounds of formula (I), (I-a) or (I-b) or, whenever possible, an interesting embodiment thereof as indicated above, wherein $R^4$ represents hydroxy.

An interesting embodiment of the present invention are those compounds of formula (I), (I-a) or (I-b) or, whenever possible, an interesting embodiment thereof as indicated above, wherein $R^4$ represents $C_{1-4}$alkyloxy, in particular methoxy.

An interesting embodiment of the present invention are those compounds of formula (I), (I-a) or (I-b) or, whenever possible, an interesting embodiment thereof as indicated above, wherein $R^5$ represents hydrogen.

An interesting embodiment of the present invention are those compounds of formula (I), (I-a) or (I-b) or, whenever possible, an interesting embodiment thereof as indicated above, wherein $R^5$ represents $C_{1-4}$alkyl, in particular methyl.

An interesting embodiment of the present invention are those compounds of formula (I), (I-a) or (I-b) or, whenever possible, an interesting embodiment thereof as indicated above, wherein $R^4$ and $R^5$ are taken together to form oxo.

An interesting embodiment of the present invention are those compounds of formula (I), (I-a) or (I-b) or, whenever possible, an interesting embodiment thereof as indicated above, wherein $R^4$ is hydroxyl and $R^5$ is hydrogen.

An interesting embodiment of the present invention are those compounds of formula (I), (I-a) or (I-b) or, whenever possible, an interesting embodiment thereof as indicated above, wherein $R^4$ is hydroxyl and $R^5$ is $C_{1-4}$alkyl, in particular methyl.

An interesting embodiment of the present invention are those compounds of formula (I), (I-a) or (I-b) or, whenever possible, an interesting embodiment thereof as indicated above, wherein $R^4$ is $C_{1-4}$alkyloxy and $R^5$ is hydrogen.

An interesting embodiment of the present invention are those compounds of formula (I), (I-a) or (I-b) or, whenever possible, an interesting embodiment thereof as indicated above, wherein Z is a radical of formula (z-1).

An interesting embodiment of the present invention are those compounds of formula (I), (I-a) or (I-b) or, whenever possible, an interesting embodiment thereof as indicated above, wherein Z is a radical of formula (z-2).

All possible combinations of the above-indicated interesting embodiments are considered to be embraced within the scope of this invention.

An interesting embodiment of the present invention are those compounds of formula (I), (I-a) or (I-b) wherein $R^1$ is —$CH_2$—OH, —$C(CH_3)_2$—OH, —$CH(CH_3)$—OH, —$CH_2$—$CH_2$—OH, —$CH(CH(CH_3)_2)$—OH, —$CH_2$—$CH_2$—CHOH—$CH_3$, —$CH$=$CH_2$ or $C(CH_3)$=$CH_2$; $R^2$ is hydrogen or methyl; $R^3$ is hydrogen or —$CH_2$—OH; $R^4$ is hydroxy or methyloxy; $R^5$ is hydrogen or methyl, or $R^4$ and $R^5$ are taken together to form oxo.

Preferably, the compounds of the above-indicated interesting embodiments are stereochemically pure.

Preferred compounds of the present invention are selected from the group consisting of

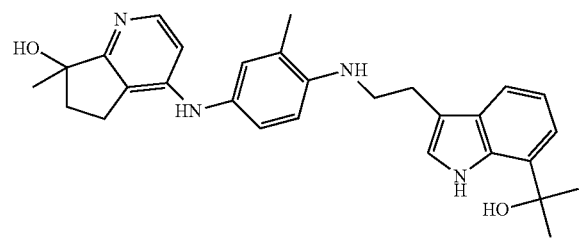

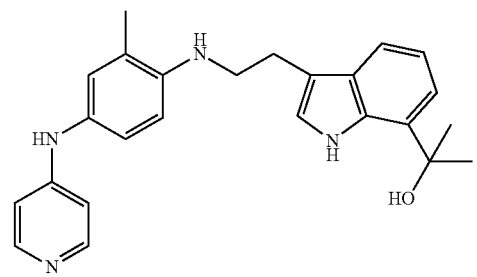

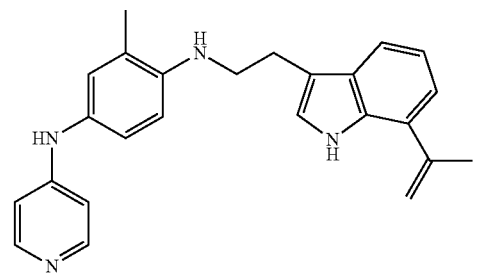

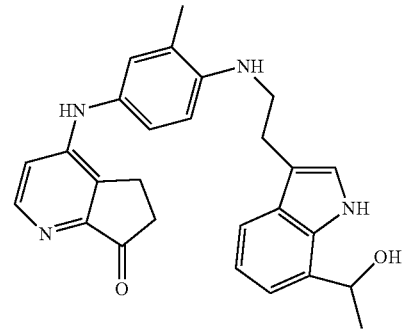

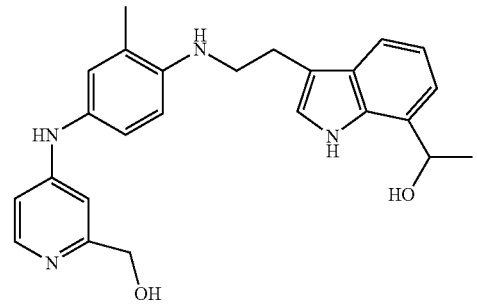

| 9 | 10 |
|---|---|
| -continued | -continued |
| 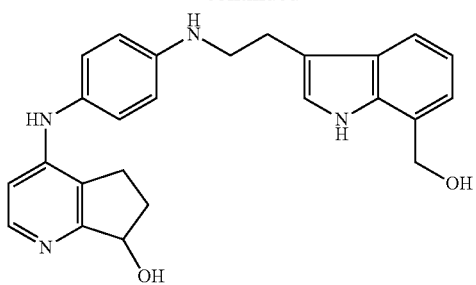 | 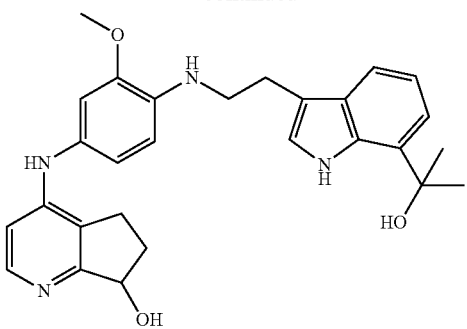 |
| 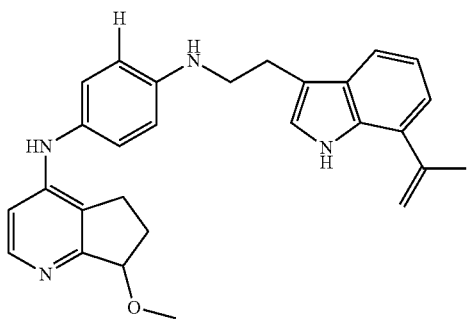 | 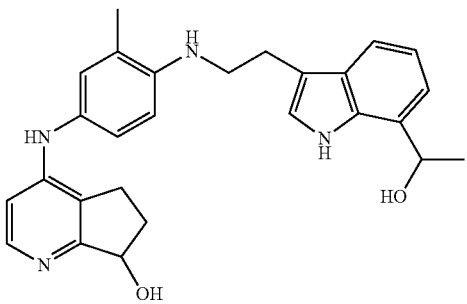 |
| 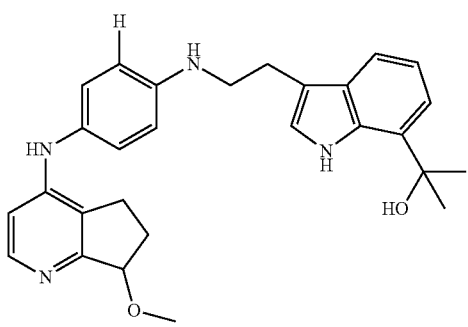 | 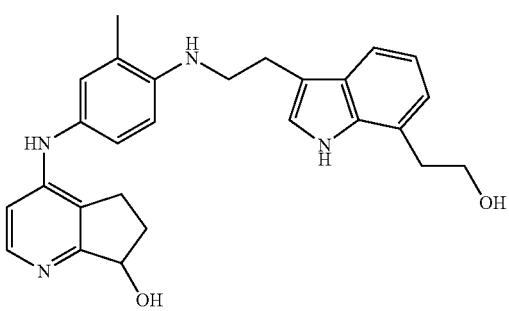 |
| 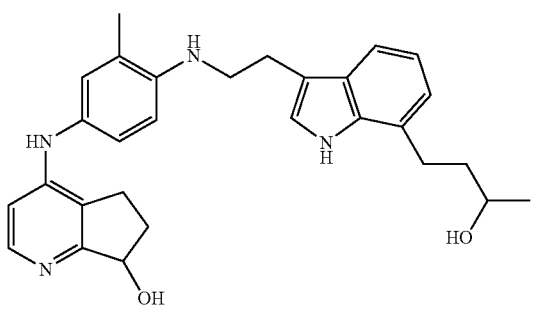 | 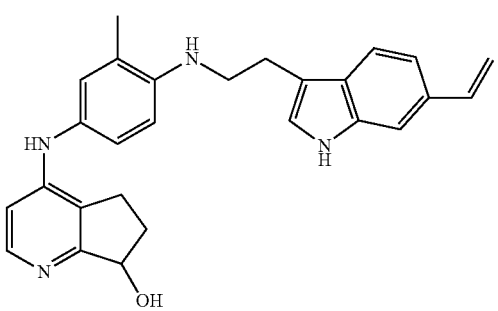 |
| 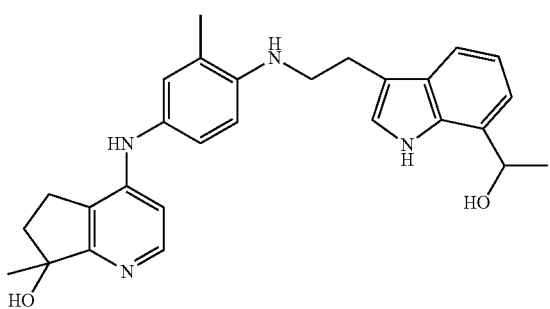 | 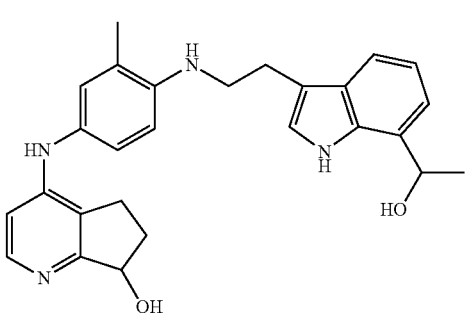 |

11
-continued
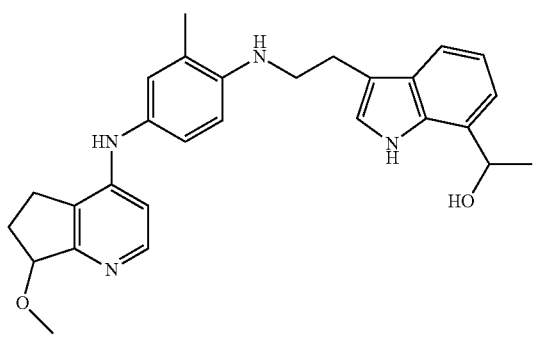
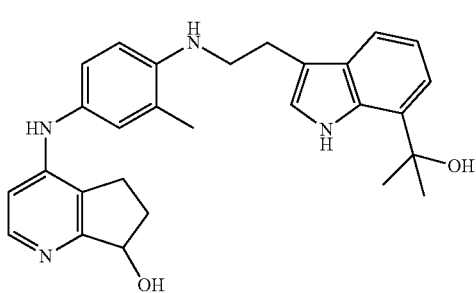
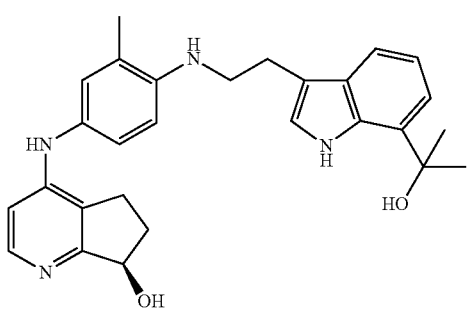
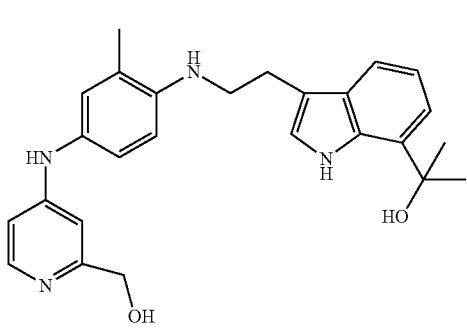
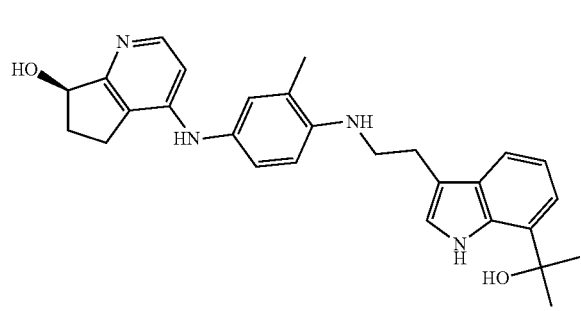
12
-continued
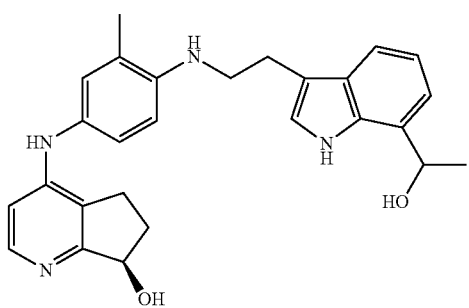
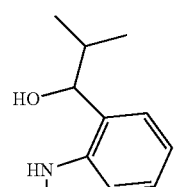
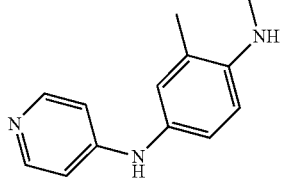
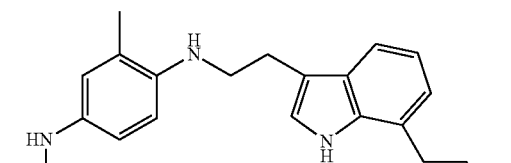
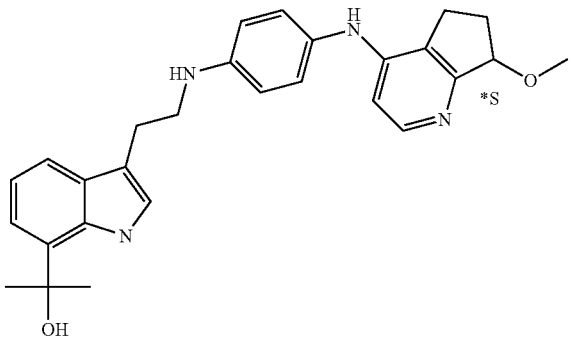

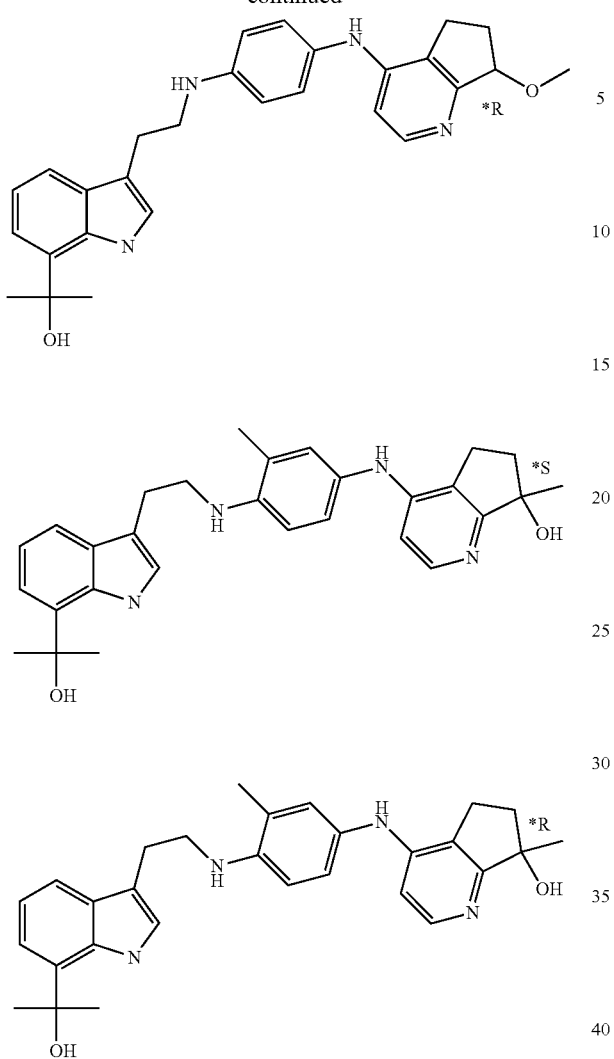
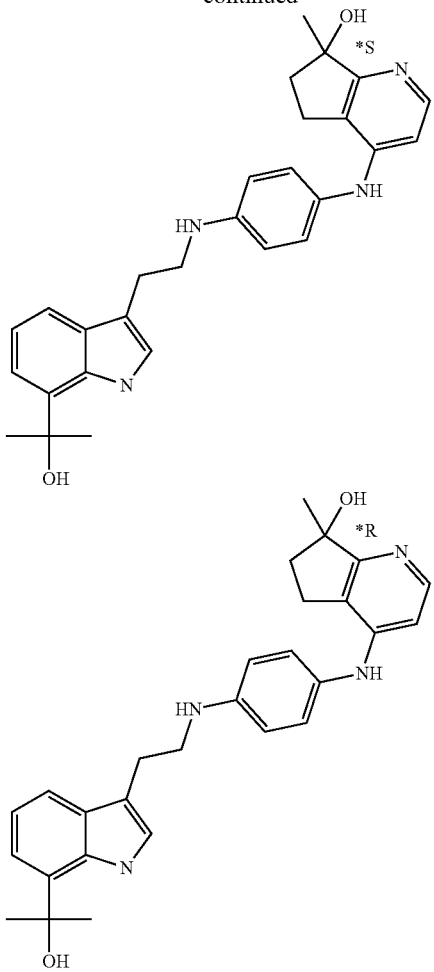
including any stereochemically isomeric form thereof; a pharmaceutically acceptable salt thereof or a solvate thereof
(* means relative stereochemistry)
Preferred compounds of the present invention are selected from the group consisting of
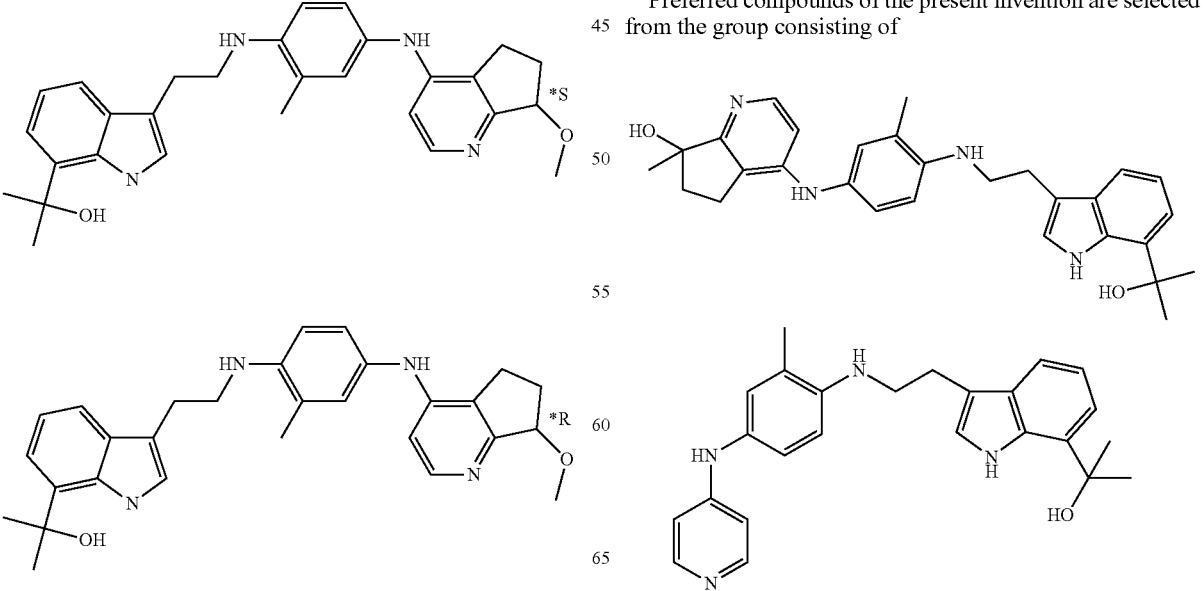

| 15 | 16 |
|---|---|
| -continued | -continued |
| 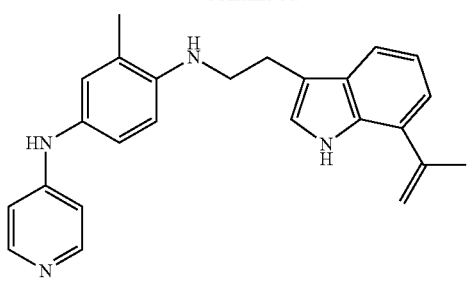 | 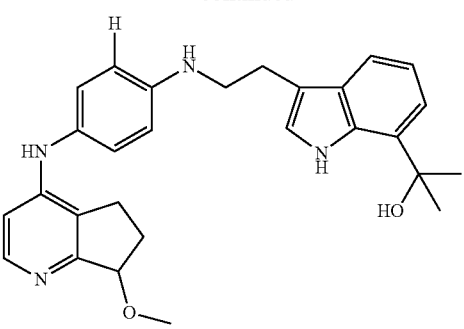 |
| 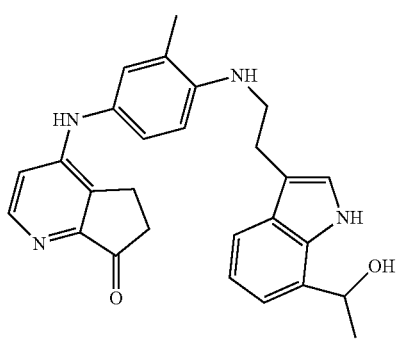 | 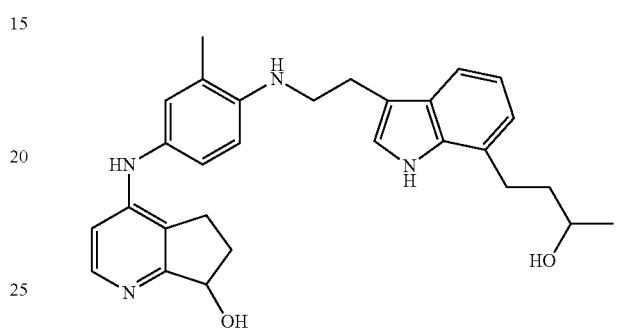 |
| 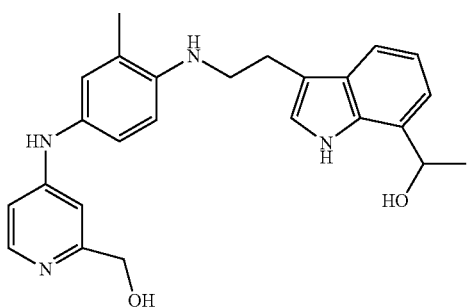 | 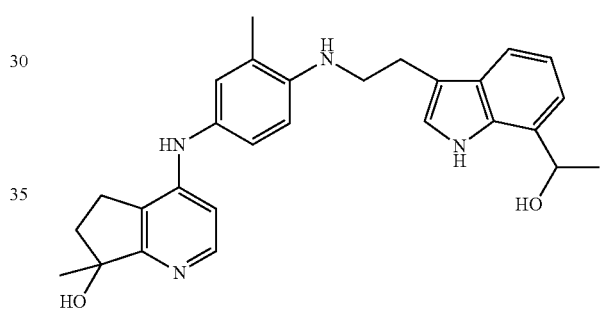 |
| 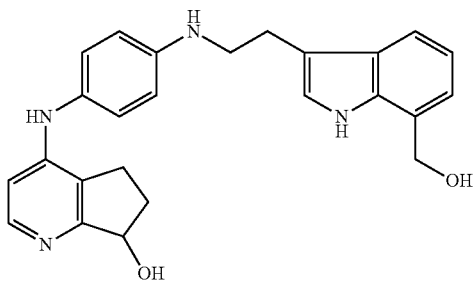 | 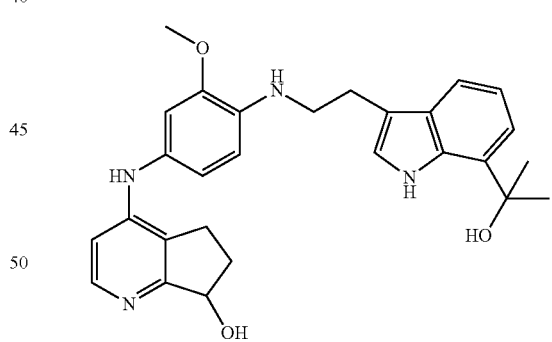 |
| 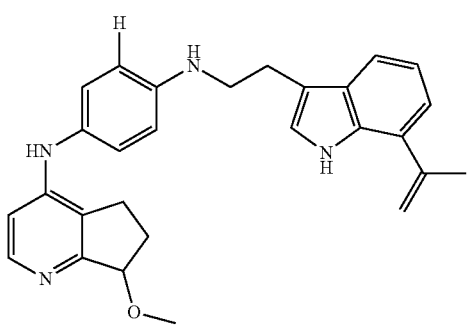 | 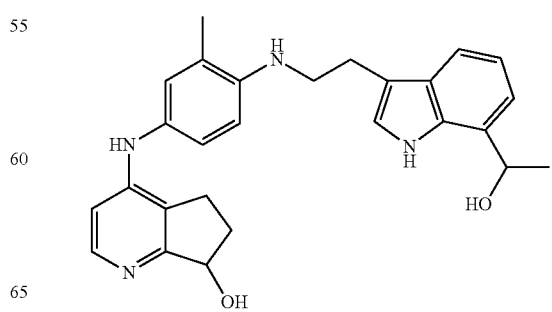 |

-continued
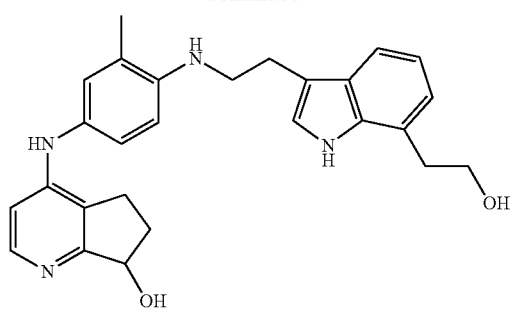
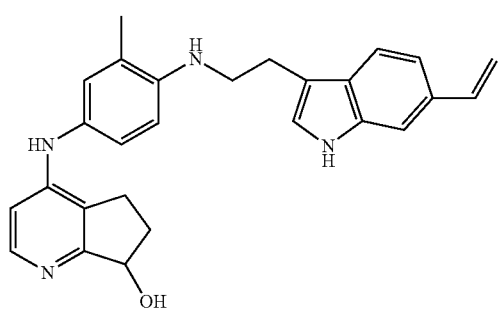
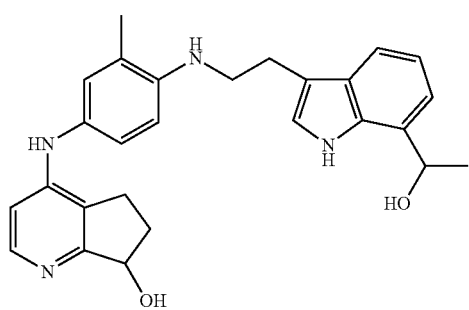
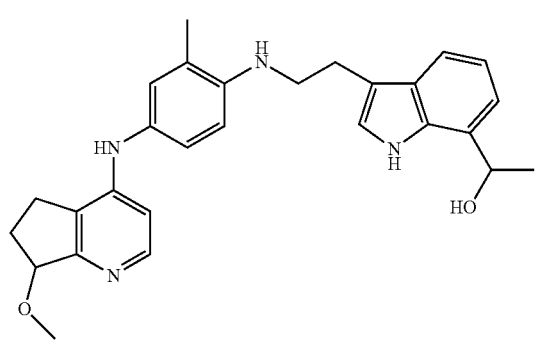
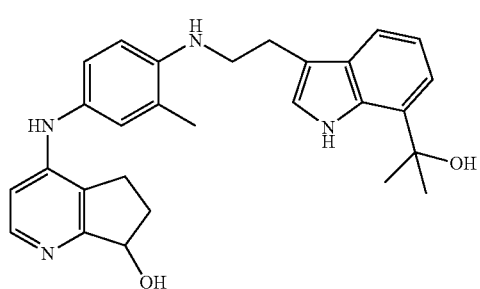
-continued
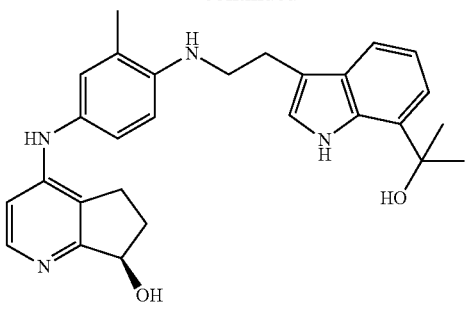
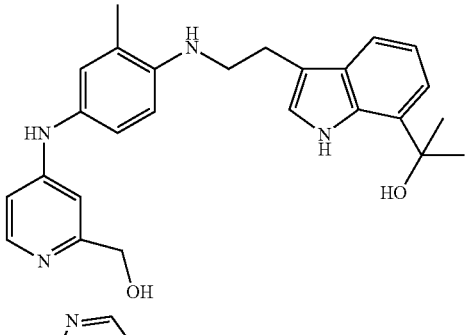
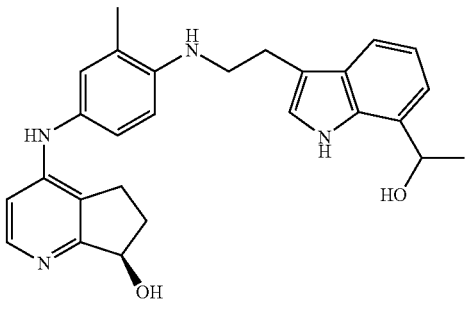
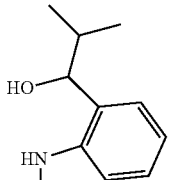
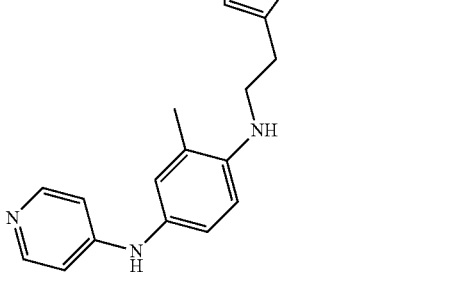

including any stereochemically isomeric form thereof;

a pharmaceutically acceptable salt thereof or a solvate thereof.

A preferred compound of the present invention is the compound having the following formula

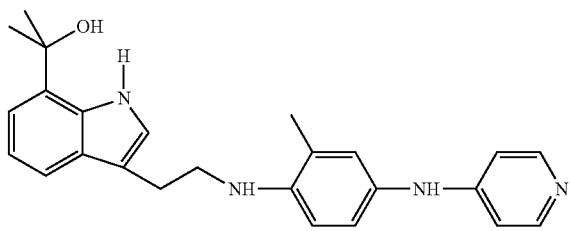 [SMILES: Cc1cc(Nc2ccncc2)ccc1NCCc1c[nH]c2c(C(C)(C)O)cccc12]

a pharmaceutically acceptable salt thereof or a solvate thereof.

A preferred compound of the present invention is the compound having the following formula

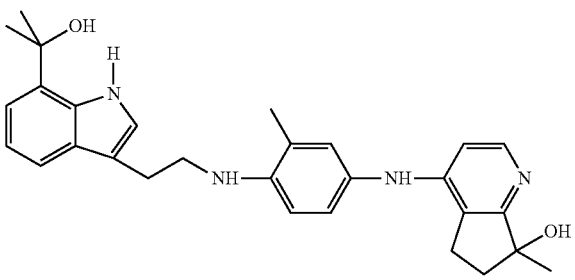 [SMILES: Cc1cc(Nc2ccnc3c2CCC3(C)O)ccc1NCCc1c[nH]c2c(C(C)(C)O)cccc12]

including any stereochemically isomeric form thereof;

a pharmaceutically acceptable salt thereof or a solvate thereof.

A preferred compound of the present invention is the enantiomer having the following formula

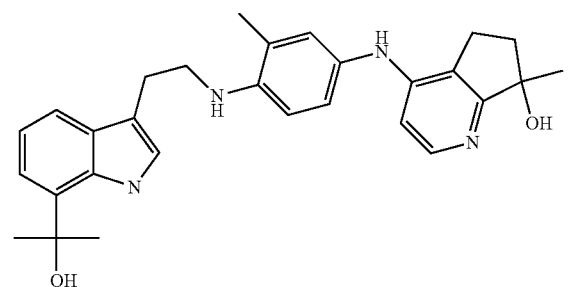 [SMILES: Cc1cc(Nc2ccnc3c2CCC3(C)O)ccc1NCCc1c[nH]c2c(C(C)(C)O)cccc12]

and having a levorotatory rotation measured with light at the wavelength of the D-line of sodium (589 nm) at a temperature of 20° C. and a cell pathlength of 1 dm in chloroform at a concentration of 8.59 mg/ml; or a pharmaceutically acceptable salt thereof or a solvate thereof.

A preferred compound of the present invention is the enantiomer having the following formula

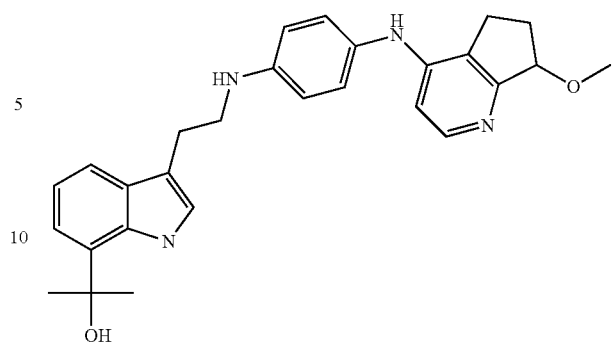

and having a dextrorotatory rotation measured with light at the wavelength of the D-line of sodium (589 nm) at a temperature of 20° C. and a cell pathlength of 1 dm in methanol at a concentration of 10.33 mg/ml; or a pharmaceutically acceptable salt thereof or a solvate thereof.

A preferred compound of the present invention is the enantiomer having the following formula

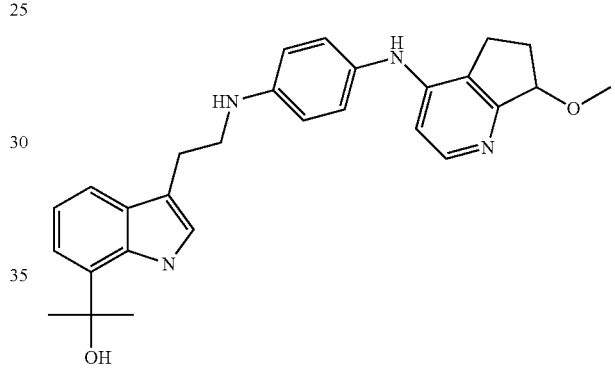

and having a levorotatory rotation measured with light at the wavelength of the D-line of sodium (589 nm) at a temperature of 20° C. and a cell pathlength of 1 dm in methanol at a concentration of 10.74 mg/ml; or a pharmaceutically acceptable salt thereof or a solvate thereof.

The compounds of formula (I), their pharmaceutically acceptable salts and stereochemically isomeric forms thereof may be prepared in conventional manner. The starting materials and some of the intermediates are known compounds and are commercially available or may be prepared according to conventional reaction procedures as generally known in the art. Reference in this respect is also made to synthesis methods described in WO2006/032631.

A number of such preparation methods will be described hereinafter in more detail. Other methods for obtaining final compounds of formula (I) are described in the examples.

In general, compounds of formula (I) can be prepared by reacting an intermediate of formula (II) with an intermediate of formula (III) wherein $W_1$ is a suitable leaving group such as, for example, halo, e.g. fluoro, chloro, bromo or iodo, or a sulfonyloxy radical such as methylsulfonyloxy, 4-methylphenylsulfonyloxy and the like. The reaction can be performed in a reaction-inert solvent such as, for example, an alcohol, e.g. methanol, ethanol, 2-methoxy-ethanol, propanol, butanol and the like; an ether, e.g. 1,4-dioxane preferably in the presence of a suitable acid, such as for example HCl, 1,1'-oxybispropane and the like; a ketone, e.g. 4-methyl-2-pentanone; or N,N-dimethylformamide, nitrobenzene, acetonitrile and the like. The addition of an appropriate base such as, for example, an alkali or earth alkaline metal carbonate or hydrogen carbonate or an organic base, e.g. N,N-diisopropylethylamine, triethylamine, sodium carbonate or potassium carbonate, may be utilized to pick up the acid which is liberated during the course of the reaction. A small amount of an appropriate metal iodide, e.g., sodium or potassium iodide may be added to promote the reaction. Stirring may enhance the rate of the reaction. The reaction may conveniently be carried out at a temperature ranging between room temperature and the reflux temperature of the reaction mixture and, if desired, the reaction may be carried out at an increased pressure.

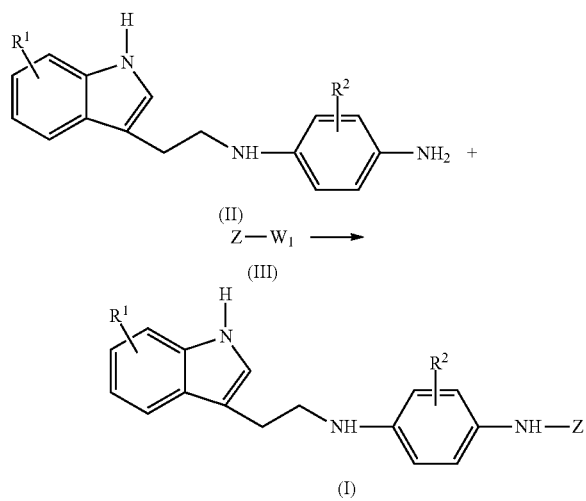

In the above reaction, intermediates of formula (II) wherein $R^1$ is —C(OH)(CH$_3$)$_2$ can result in the corresponding final compound of formula (I) wherein $R^1$ is —C(CH$_3$)═CH$_2$.

The above reaction of an intermediate of formula (III) with an intermediate of formula (II) can also be performed in the presence of a suitable catalyst, such as for example Pd(dba)$_2$ (bis[(1,2,4,5-η)-1,5-diphenyl-1,4-pentadien-3-one]-palladium) a suitable ligand, such as for example BINAP (2,2'-bis (diphenylphosphino)-1,1'-binaphthyl), a suitable base, such as for example sodium tertiair butoxide, and a suitable solvent, such as for example toluene.

Compounds of formula (I) wherein $R^1$ represents hydroxyC$_{1-4}$alkyl, said compounds being represented by formula (I-1), can also be prepared by reducing the corresponding carbonyl derivative of formula (IV) in the presence of a suitable reducing agent, such as for example NaBH$_4$, and a suitable solvent, such as for example an alcohol, e.g. methanol and the like.

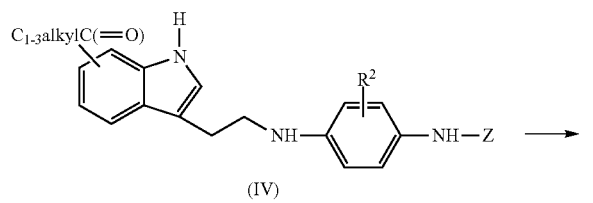

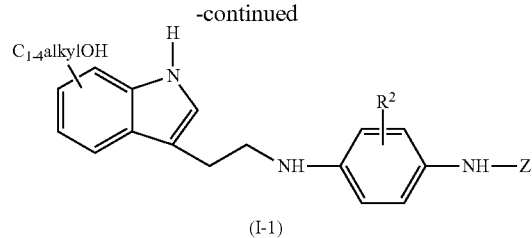

Compounds of formula (I-1) can also be prepared by reducing the corresponding ester derivative of formula (V) wherein Rx represents —C$_{1-3}$alkylC(═O)OC$_{1-4}$alkyl, in the presence of a suitable reducing agent, such as for example LiAlH$_4$, and a suitable solvent, such as for example tetrahydrofuran.

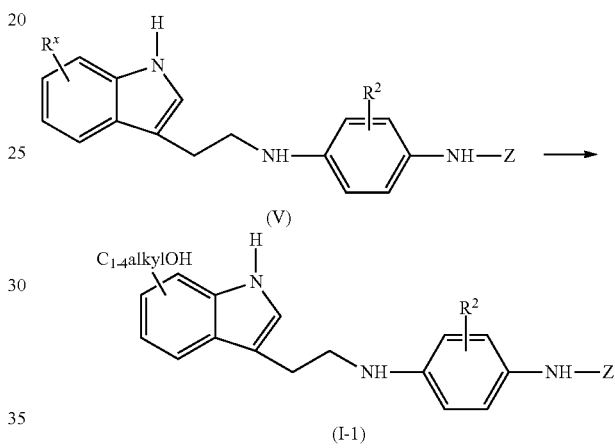

Compounds of formula (I-1) wherein the $R^1$ represents hydroxyC$_{1-4}$alkyl and said hydroxyC$_{1-4}$alkyl is placed in position 7 of the indole moiety, said compounds being represented by formula (I-1-a), can also be prepared by hydrolysis of an intermediate of formula (VI) with a suitable base, such as for example sodium hydroxide, and a suitable solvent, such as for example tetrahydrofuran, or an alcohol, e.g. ethanol and the like.

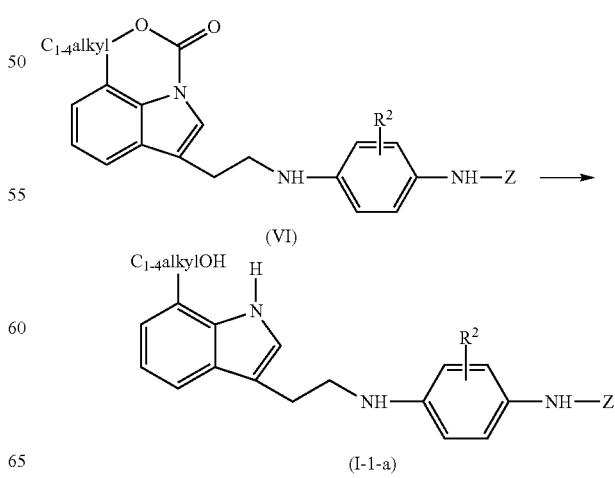

The compounds of formula (I) may also be converted into each other via art-known reactions or functional group transformations.

The compounds of formula (I) can also be converted into a pharmaceutically acceptable acid addition salt by reaction with an appropriate acid, such as for example hydrochloric acid, in a suitable solvent, such as for example an alcohol, e.g. 2-propanol, diethylether, diisopropyl ether.

Some of the intermediates and starting materials are known compounds and may be commercially available or may be prepared according to art-known procedures.

In general, intermediates of formula (II) can be prepared by hydrogenating an intermediate of formula (VII) in the presence of a suitable metal catalyst, such as for example Raney nickel, in the presence of a suitable solvent, such as for example an alcohol, e.g. methanol or ethanol and the like; or platina on charcoal, in the presence of a suitable catalyst poison, such as a thiophene solution and vanadium pentoxide, in the presence of a suitable solvent, such as foexample tetrahydrofuran.

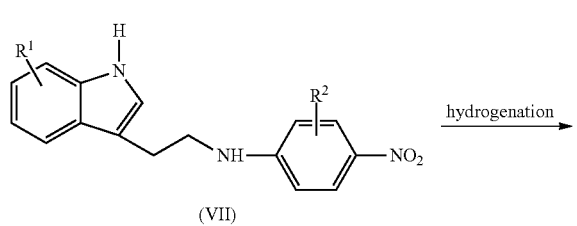

Intermediates of formula (VII) can be prepared by reacting an intermediate of formula (VIII) with an intermediate of formula (IX) wherein $W_2$ represents a suitable leaving group, such as for example a halo atom, e.g. chloro, bromo, fluoro and the like, in the presence of a suitable solvent, such as for example N,N-dimethylsulfoxide. The addition of an appropriate base such as, for example, an alkali or earth alkaline metal carbonate or hydrogen carbonate or an organic base, e.g. N,N-diisopropylethylamine, triethylamine, sodium carbonate, sodium hydrogen carbonate, or potassium carbonate, may be utilized to pick up the acid which is liberated during the course of the reaction.

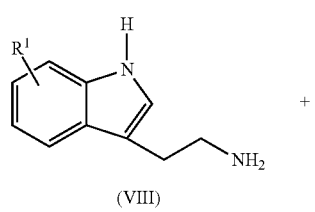

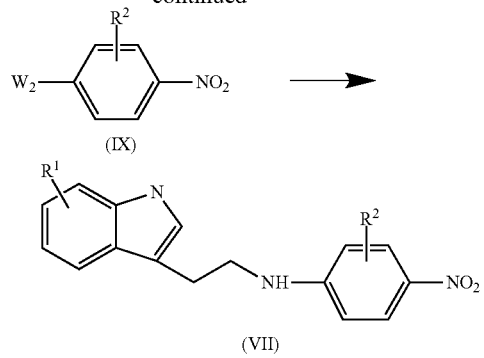

Intermediates of formula (VIII) can be prepared from the corresponding intermediate of formula (X) in the presence of Raney Nickel and $NH_3$ in the presence of a suitable solvent, such as for example an alcohol, e.g. methanol and the like.

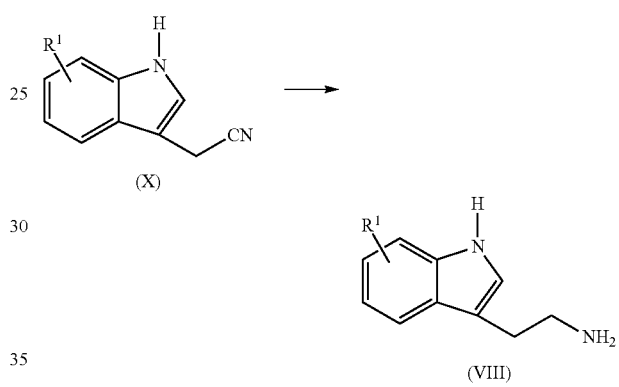

Intermediates of formula (X) wherein $R^1$ represents hydroxy$C_{1-4}$alkyl, e.g. —CH(OH)(CH$_3$), said intermediates being represented by formula (X-a), can be prepared from an intermediate of formula (XI) by reaction with CH$_3$MgCl in the presence of a suitable solvent, such as for example tetrahydrofuran.

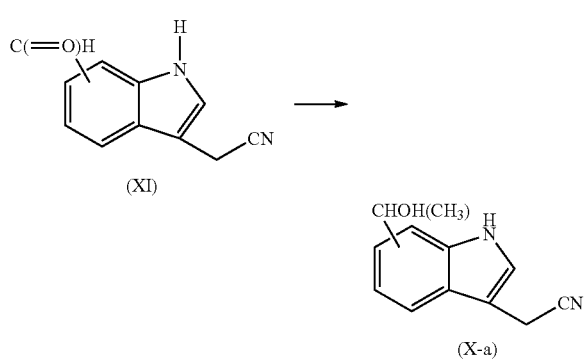

The same reaction can be used to prepare other alternatives of hydroxy$C_{1-4}$alkyl. For example intermediates wherein $R^1$ represents —C(OH)(CH$_3$)$_2$, can be prepared from the corresponding intermediate with —C(=O)—CH$_3$.

Intermediates of formula (XI) can be prepared by reacting an intermediate of formula (XII) with sodium cyanide in the presence of a suitable solvent, such as for example N,N-dimethylformamide.

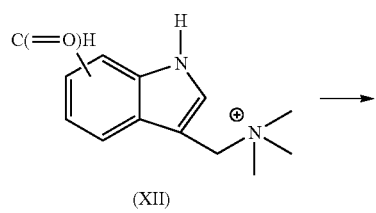

(XII)

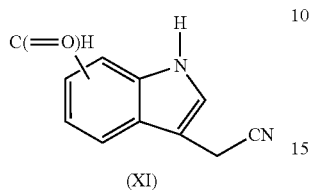

(XI)

Alternatively, intermediates of formula (XI) can also be prepared by oxidation from the corresponding hydroxyl analogue in the presence of Dess-Martin periodinane and a suitable solvent, such as for example dichloromethane.

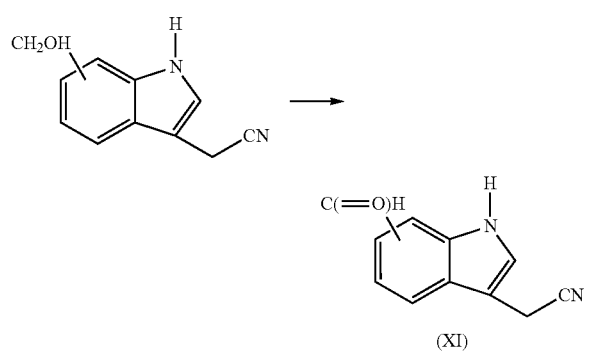

Intermediates of formula (XII) may be prepared by reacting an intermediate of formula (XIII) with $CH_3I$ in the presence of a suitable solvent, such as an alcohol, e.g. ethanol.

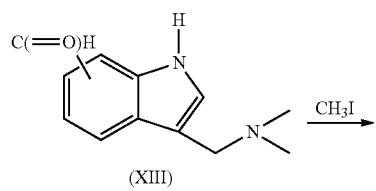

(XIII)

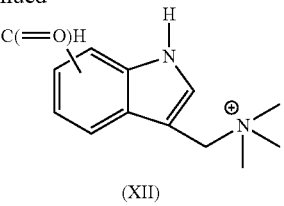

(XII)

Intermediates of formula (XIII) can be prepared by reacting an intermediate of formula (XIV) with Eschenmosser's salt in the presence of acetic acid.

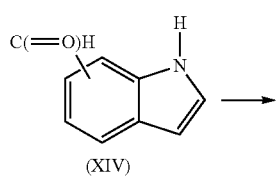

(XIV)

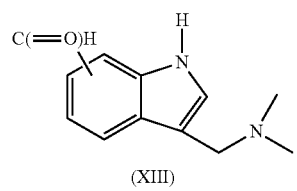

(XIII)

Intermediates of formula (XIV) can be prepared by oxidizing the corresponding hydroxyl analogue in the presence of a suitable oxidizing agent, such as for example $MnO_2$, in the presence of a suitable solvent, such as for example dichloromethane.

Intermediates of formula (III) wherein Z is a radical of formula (z-2) and $R^4$ is hydroxyl, said intermediates being represented by formula (III-a), can be prepared by reducing an intermediate of formula (III-b) with a suitable reducing agent, such as for example $NaBH_4$, in the presence of a suitable solvent, such as for example an alcohol, e.g. methanol.

Intermediates of formula (III-a) can be converted into an intermediate of formula (III-c) by reaction with $C_{1-4}$alkyliodide, in the presence of a suitable base, such as sodium hydride, and a suitable solvent, such as for example tetrahydrofuran. Intermediates of formula (III-b) can be prepared by oxidation of an intermediate of formula (III-a) by reaction with a suitable oxidizing agent, such as for example $MnO_2$, in the presence of a suitable solvent, such as for example dichloromethane. Intermediates of formula (III-b) can be converted into an intermediate of formula (III-d) by reaction with $C_{1-4}$alkylMgCl in the presence of a suitable solvent, such as for example tetrahydrofuran.

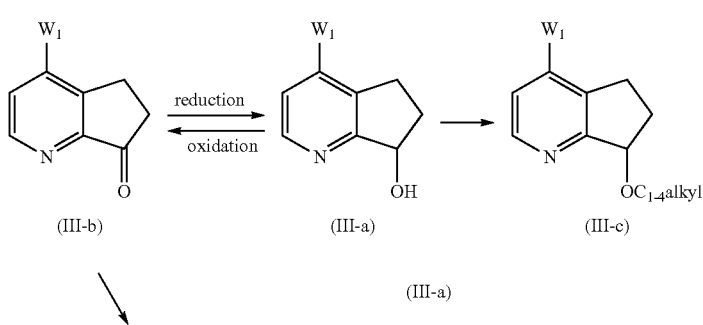

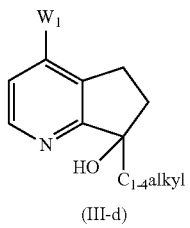

(III-d)

The intermediates of formula (III-a) can also be prepared by stirring the intermediate of formula (XV) in a mixture of methanol/NH₃. If desired the intermediate of formula (III-a) can be converted into the intermediate of formula (XV) by stirring in a mixture of acetic anhydride and pyridine.

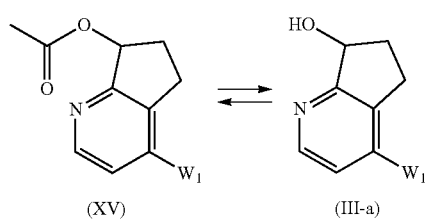

(XV)    (III-a)

The S-enantiomer of intermediate (III-a), herein referred to as the intermediate of formula (III-a-1), and the R-enantiomer of the intermediate of formula (XV), herein referred to as the intermediate of formula (XV-b), can be prepared by adding Lipase *Candida Antartica* B to a racemic mixture of the intermediate of formula (III-a) in a suitable solvent such as acetic acid ethenyl ester (see Scheme 1). When desired the intermediate of formula (XV-b) can be converted into the R enantiomer of intermediate (III-a), herein referred to as intermediate of formula (III-a-2), by reaction in MeOH/NH₃.

Starting from the racemic mixture this method affords the conversion of one of the enantiomers in its acetate with ee>99% and 58% yield and the second enantiomer is isolated with ee>99% in 42% yield.

The term enantiomeric excess (ee) is well-known to the person skilled in stereochemistry. For a mixture of (+) and (−) enantiomers, with composition given as the mole or weight fractions of F(+) and F(−) (where F(+)+F(−)=1), the enantiomeric excess for F(*) is defined as F(+)−F(−), and the percent enantiomeric excess as 100*[F(+)−F(−)].

Scheme 1

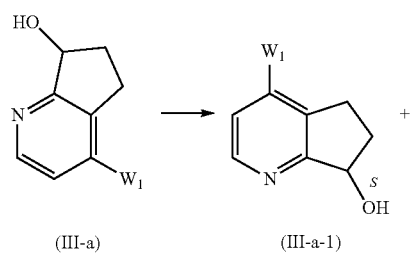

(III-a)    (III-a-1)

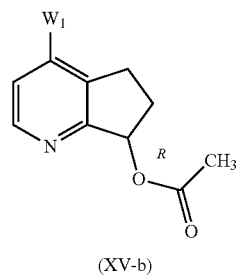

(XV-b)

Alternatively, the R-enantiomer of intermediate (III-a), herein referred to as the intermediate of formula (III-a-2), and the S— enantiomer of the intermediate of formula (XV), herein referred to as the intermediate of formula (XV-a), can be prepared by adding Lipase *Candida Antartica* B to a racemic mixture of the intermediate of formula (XV) in water (see Scheme 2). When desired, intermediate (XV-a) can be converted into intermediate (III-a-1) by reaction in MeOH/NH₃.

Scheme 2

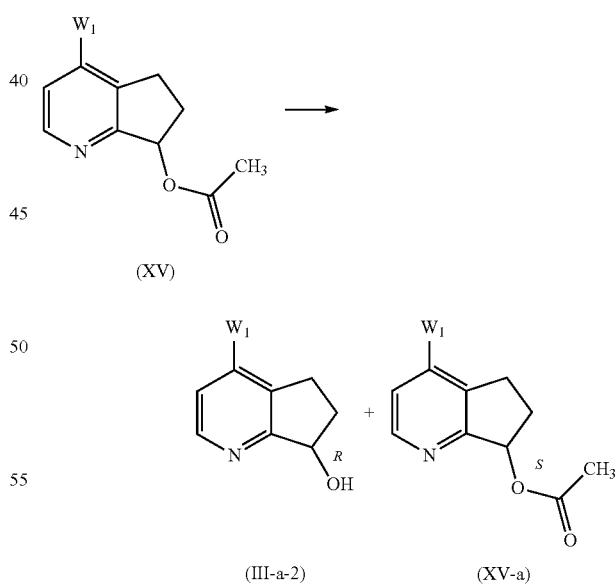

(XV)

(III-a-2)    (XV-a)

Alternatively, the intermediate of formula (III-a) can also be separated into its enantiomers by chiral column chromatography.

The intermediates of formula (XV) can be prepared by stirring the intermediate of formula (XVI) in acetic anhydride.

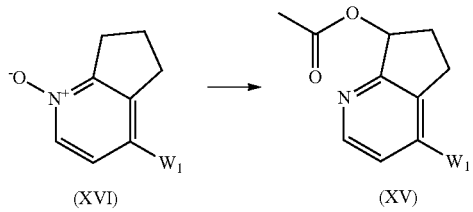

The intermediates of formula (XVI) wherein $W_1$ is chloro, herein referred to the intermediate of formula (XVI-a), can be prepared by adding benzyltriethylammonium chloride and sodium chloride to a solution of the intermediate of formula (XVII) in acetonitrile, followed by the addition of concentrated hydrochloric acid.

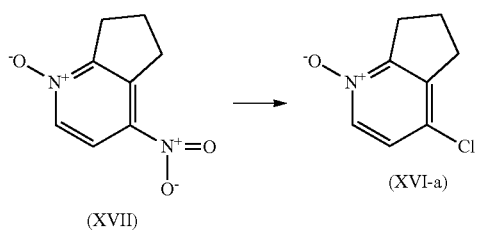

The intermediates of formula (XVII) can be prepared by adding fuming nitric acid to sulfuric acid followed by portionwise addition of 6,7-dihydro-5H-cyclopenta[b]pyridine, 1-oxide.

Intermediates of formula (IV) can be prepared according to the above reaction protocols for intermediates of formula (II).

Intermediates of formula (V) can be prepared by deprotecting an intermediate of formula (XVIII) wherein P represents a suitable protective group, such as for example —C(=O)—O—C(CH$_3$)$_3$, in the presence of a suitable acid, such as for example hydrochloric acid, and a suitable solvent, such as for example acetonitrile.

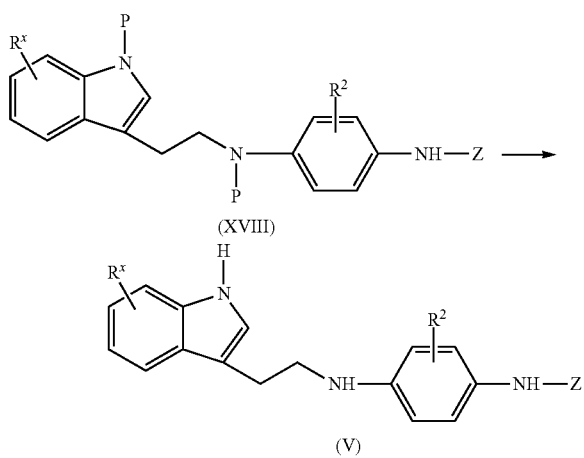

Intermediates of formula (XVIII) can be prepared by reacting an intermediate of formula (XIX) with an intermediate of formula (III) in the presence of a reaction-inert solvent such as, for example, an alcohol, e.g. methanol, ethanol, 2-methoxy-ethanol, propanol, isopropanolbutanol and the like; an ether, e.g. 1,4-dioxane preferably in the presence of a suitable acid such as for example HCl, 1,1'-oxybispropane and the like; a ketone, e.g. 4-methyl-2-pentanone; or N,N-dimethylformamide, nitrobenzene, acetonitrile and the like. The addition of an appropriate base such as, for example, an alkali or earth alkaline metal carbonate or hydrogen carbonate or an organic base, e.g. N,N-diisopropylethylamine, triethylamine, sodium carbonate or potassium carbonate, may be utilized to pick up the acid which is liberated during the course of the reaction. A small amount of an appropriate metal iodide, e.g. sodium or potassium iodide, may be added to promote the reaction. Stirring may enhance the rate of the reaction. The reaction may conveniently be carried out at a temperature ranging between room temperature and the reflux temperature of the reaction mixture and, if desired, the reaction may be carried out at an increased pressure.

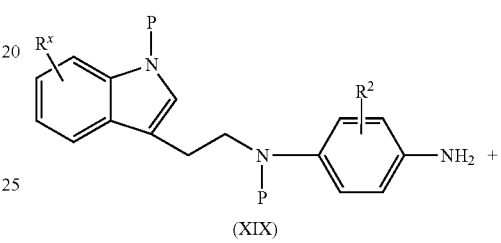

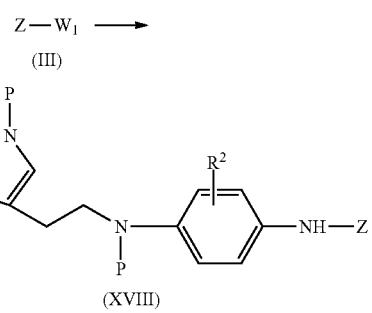

Intermediates of formula (XIX) can be prepared according to the reaction protocols described above for intermediates of formula (II).

Intermediates of formula (VI) can be prepared by reacting an intermediate of formula (XX) wherein P represents a suitable protective group as defined above and $R^y$ represents —C$_{1-4}$alkyl-O—Si(CH$_3$)$_2$C(CH$_3$)$_3$, in the presence of a suitable acid, such as for example trifluoroacetic acid, and a suitable solvent, such as for example dichloromethane.

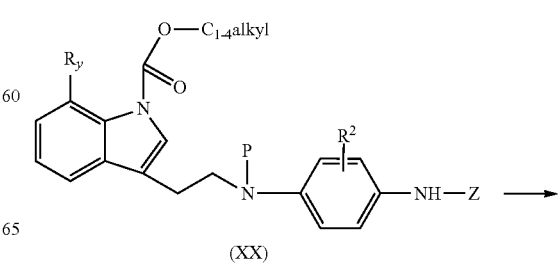

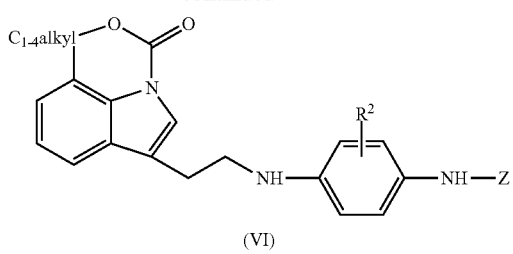

(VI)

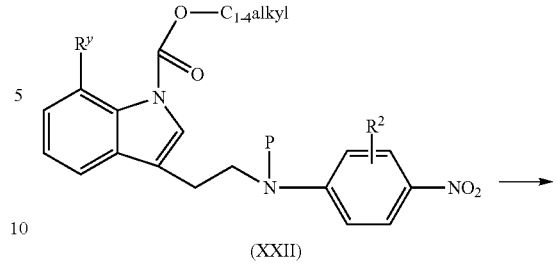

(XXII)

Intermediates of formula (XX) can be prepared by reacting an intermediate of formula (XXI) with an intermediate of formula (III) in the presence of a reaction-inert solvent such as, for example, an alcohol, e.g. methanol, ethanol, 2-methoxy-ethanol, propanol, isopropanolbutanol and the like; an ether, e.g. 1,4-dioxane preferably in the presence of a suitable acid such as for example HCl, 1,1'-oxybispropane and the like; a ketone, e.g. 4-methyl-2-pentanone; or N,N-dimethylformamide, nitrobenzene, acetonitrile and the like. The addition of an appropriate base such as, for example, an alkali or earth alkaline metal carbonate or hydrogen carbonate or an organic base, e.g. N,N-diisopropylethylamine, triethylamine, sodium carbonate or potassium carbonate, may be utilized to pick up the acid which is liberated during the course of the reaction. A small amount of an appropriate metal iodide, e.g. sodium or potassium iodide, may be added to promote the reaction. Stirring may enhance the rate of the reaction. The reaction may conveniently be carried out at a temperature ranging between room temperature and the reflux temperature of the reaction mixture and, if desired, the reaction may be carried out at an increased pressure.

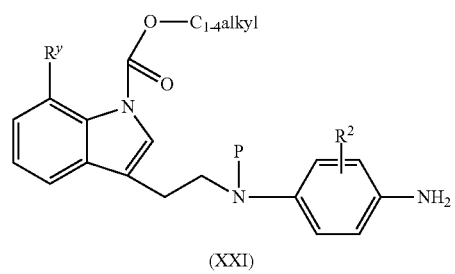

(XXI)

Intermediates of formula (XXII) wherein P represents —C(=O)—O—$C_{1-4}$alkyl, said intermediate being represented by formula (XXII-a), can be prepared by reacting an intermediate of formula (XXIII) with di-tert-butyl dicarbonate in the presence of a suitable base, such as for example triethylamine, and a suitable solvent, such as for example 4-(dimethyl)aminopyridine.

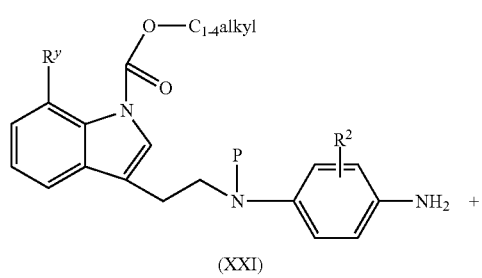

(XXI)

Z—$W_1$ ⟶
(III)

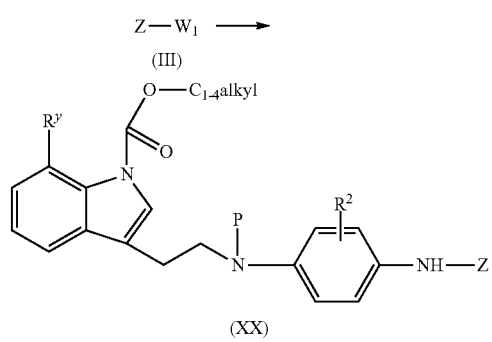

(XX)

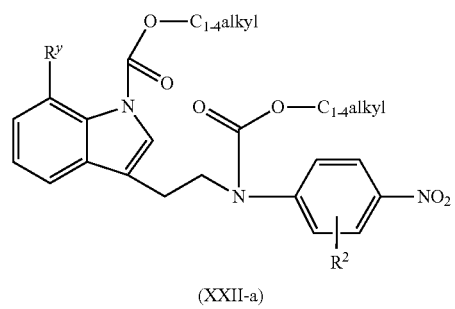

(XXIII)

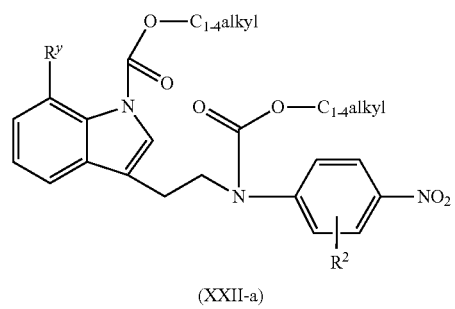

(XXII-a)

Intermediates of formula (XXI) can be prepared from the corresponding nitro intermediate of formula (XXII) by hydrogenation in the presence of a suitable catalyst, such as for example Raney nickel, and a suitable solvent, such as for example an alcohol, e.g. methanol and the like.

Intermediates of formula (XXIII) can be prepared by reacting an intermediate of formula (XXIV) with an intermediate of formula (IX) in the presence of a suitable base, such as for example sodium bicarbonate, and a suitable solvent, such as for example N,N-dimethylsulfoxide.

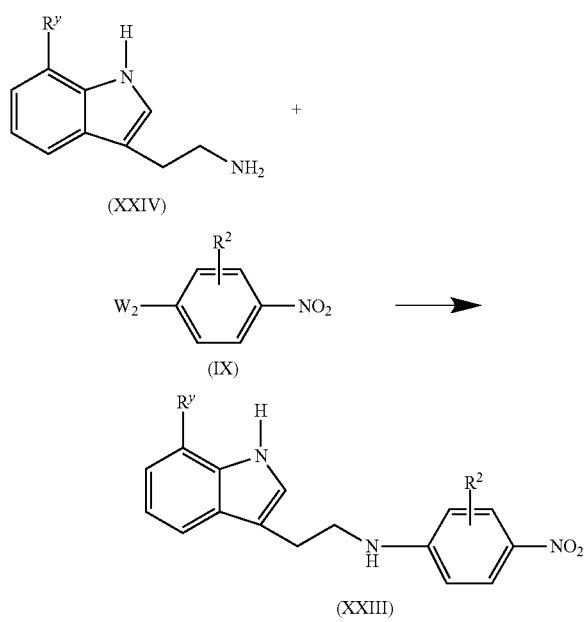

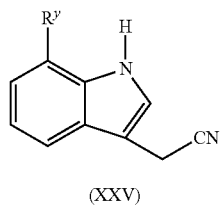

Intermediates of formula (XXVI) can be prepared as described above for intermediates of formula (XI).

The compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization, supercritical fluid chromatography or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

Intermediates of formula (XXIV) can be prepared by reacting an intermediate of formula (XXV) with $NH_3$ in the presence of a suitable catalyst, such as for example Raney Nickel, in the presence of a suitable solvent, such as for example an alcohol, e.g. methanol and the like.

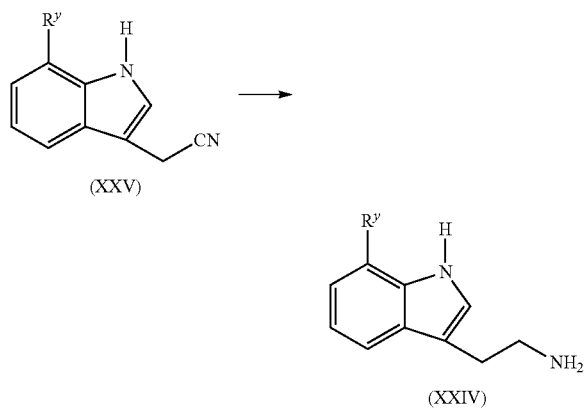

Intermediates of formula (XXV) can be prepared by reacting an intermediate of formula (XXVI) with tert-butyldimethylsilylchloride in the presence of a suitable base, such as for example imidazole, and a suitable solvent, such as for example tetrahydrofuran.

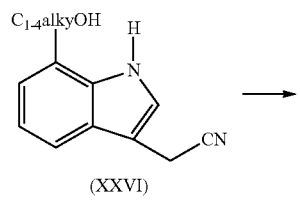

The compounds of formula (I), including any stereochemically isomeric form thereof, the pharmaceutically acceptable salts thereof or the solvates thereof have valuable pharmacological properties in that they increase the expression of p53, show potent antiproliferative activity, show potent anti-tumour activity.

As indicated before, the compounds of the invention increase the expression of p53 in the assay described in C.1. This increase may be caused by, but is not limited to, one or more of the following mechanisms of action:

- interactions with upstream or downstream targets, e.g. kinases, or enzyme activities involved in ubiquitination or SUMO modification,
- direct or indirect stabilization of the p53 protein, e.g. by keeping it in its functional structural form, or by preventing misfolding,
- enhancing p53 expression or expression of p53 family members, e.g. p63 and p73,
- increasing p53 activity, for example by (but not limited to), enhancing its transcriptional activity and/or
- increasing expression of genes and proteins of the p53-signalling pathway, for example (but not limited to) p21waf1, cip1, MIC-1 (GDF-15), PIG-3, Bax, Puma, Noxa, and ATF-3.

Hence, the present invention discloses the compounds of formula (I) for use as a medicine, in particular for the treatment of cancer or related diseases, for inhibiting tumour growth, for increasing the expression of p53.

Furthermore, the invention also concerns the use of a compound for the manufacture of a medicament for the treatment of a disorder mediated through decreased expression of p53, in particular for the treatment of cancer wherein said compound is a compound of formula (I).

The term "treating" or "treatment" as used herein covers any treatment of a disease and/or condition in an animal, particularly a human, and includes: (i) preventing a disease and/or condition from occurring in a subject which may be predisposed to the disease and/or condition but has not yet been diagnosed as having it; (ii) inhibiting the disease and/or condition, i.e., arresting its development; (iii) relieving the disease and/or condition, i.e., causing regression of the disease and/or condition.

With the term "a disorder mediated through decreased expression of p53" is meant any undesired or detrimental condition which can be inhibited by, of which the development can be arrested by, which can be relieved by or of which regression can be caused by apoptosis, induction of cellular death, or regulation of the cell cycle.

This invention also provides a method for treating a disorder mediated through a decreased expression of p53, in particular for treating cancer, by administering an effective amount of a compound of the present invention, to a subject, e.g. a mammal (and more particularly a human) in need of such treatment.

The compounds of the invention can have antiproliferative effects in tumour cells, even if such cells are devoid of functional p53. More in particular, the compounds of the invention can have antiproliferative effects in tumours with wild-type or mutant p53 and/or in tumours overexpressing MDM2. The compounds may affect angiogenesis, tumor cell migration, invasion or metastasis.

Thus, this invention also provides a method for inhibiting tumour growth by administering an effective amount of a compound of the present invention, to a subject, e.g. a mammal (and more particularly a human) in need of such treatment.

Examples of tumours including adult and pediatric malignancies, which may be inhibited by the compounds of the present invention include, but are not limited to, lung cancer including small cell lung cancer and non-small cell lung cancer (e.g. adenocarcinoma), pancreatic cancers, colon cancers (e.g. colorectal carcinomas, such as, for example, colon adenocarcinoma and colon adenoma), oesophageal cancer, oral squamous carcinoma, tongue carcinoma, gastric carcinoma, liver cancer, nasopharyngeal cancer, hematopoietic tumours of lymphoid lineage (e.g. acute lymphocytic leukemia, B-cell lymphoma, Burkitt's lymphoma), non-Hodgkin's lymphoma (e.g. mantle cell lymphoma), Hodgkin's disease, myeloid leukemias (for example, acute myelogenous leukemia (AML) or chronic myelogenous leukemia (CML)), acute lymphoblastic leukemia, chronic lymphocytic leukemia (CLL), thyroid follicular cancer, myelodysplastic syndrome (MDS), tumours of mesenchymal origin, soft tissue sarcomas, liposarcomas, gastrointestinal stromal sarcomas, malignant peripheral nerve sheath tumours (MPNST), Ewing sarcomas, leiomyosarcomas, mesenchymal chondrosarcomas, lymphosarcomas, fibrosarcomas, rhabdomyosarcomas, melanomas, teratocarcinomas, neuroblastomas, brain tumours, medulloblastoma, gliomas, benign tumour of the skin (e.g. keratoacanthomas), breast carcinoma (e.g. advanced breast cancer), kidney carcinoma, nephroblastoma, ovary carcinoma, cervical carcinoma, endometrial carcinoma, bladder carcinoma, prostate cancer including the advanced disease and hormone refractory prostate cancer, testicular cancers, osteosarcoma, head and neck cancer, epidermal carcinoma, multiple myeloma (e.g. refractory multiple myeloma), mesothelioma. Particular cancers that can be treated with the compounds of the present invention are breast cancer, colorectal cancer, non-small cell lung cancer, acute myelogenous leukemia (AML).

The compounds of the present invention can also be used for the treatment and prevention of inflammatory conditions.

Thus, this invention also provides a method for the treatment and prevention of inflammatory conditions by administering an effective amount of a compound of the present invention, to a subject, e.g. a mammal (and more particularly a human) in need of such treatment.

The compounds of the present invention can also be used for the treatment of autoimmune diseases and conditions. With the term "autoimmune diseases" is meant any disease in which an animal's immune system reacts adversely to a self-antigen. With the term "self-antigen" is meant any antigen that is normally found in the animal's body. Representative autoimmune diseases include but are not limited to: Hashimoto's thyroiditis, Grave's disease, multiple sclerosis, pernicious anemia, Addison's disease, insulin-dependent diabetes mellitus, rheumatoid arthritis, systemic lupus erythematosus (SLE or lupus), dermatomyositis, Crohn's disease, Wegener's granulomatosis, Anti Glomerular Basement Membrane Disease, Antiphospholipid Syndrome, Dermatitis Herpetiformis, Allergic Encephalomyelitis, Glomerulonephritis, Membranous Glomerulonephritis, Goodpasture Syndrome, Lambert-Eaton, Myasthenic Syndrome, Myasthenia Gravis, Bullous Pemphigoid, Polyendocrinopathies, Reiter's Disease, and Stiff-Man Syndrome.

Thus, this invention also provides a method for the treatment of autoimmune diseases and conditions by administering an effective amount of a compound of the present invention, to a subject, e.g. a mammal (and more particularly a human) in need of such treatment.

The compounds of the present invention can also be useful for the treatment of diseases associated with conformational unstable or misfolded proteins.

Examples of diseases associated with conformational unstable or misfolded proteins include but are not limited to: cystic fibrosis (CFTR), Marfan syndrom (fibrillin), Amyotrophic lateral sclerosis (superoxide dismutase), scurvy (collagen), maple syrup urine disease (alpha-ketoacid dehydrogenase complex), osteogenesis imperfecta (type1 procollagen pro-alpha), Creutzfeldt-Jakob disease (prion), Alzheimer's disease (beta-amyloid), familial amyloidosis (lysozyme), cataracts (crystallins), familial hypercholesterolemia (LDL receptor), α I-antitrypsin deficiency, Tay-Sachs disease (beta-hexosaminidase), retinitis pigmentosa (rhodopsin), and leprechaunism (insulin receptor).

Thus, this invention also provides a method for the treatment of diseases associated with conformational unstable or misfolded proteins by administering an effective amount of a compound of the present invention, to a subject, e.g. a mammal (and more particularly a human) in need of such treatment.

In view of their useful pharmacological properties, the subject compounds may be formulated into various pharmaceutical forms for administration purposes.

To prepare the pharmaceutical compositions of this invention, an effective amount of a compound of the present invention, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is administered in an amount sufficient to induce apoptosis, induce cellular death, or regulate the cell cycle.

Thus, the compound of the invention is administered in an amount sufficient to increase expression of p53, or to exert its anti-tumour activity.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, in particular 1 mg to 500 mg, more in particular 10 mg to 500 mg of active ingredient per unit dosage form.

Depending on the mode of administration, the pharmaceutical composition will preferably comprise from 0.05 to 99% by weight, more preferably from 0.1 to 70% by weight, even more preferably from 0.1 to 50% by weight of the compound of the present invention, and, from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anticancer agent is envisaged, especially for use as a medicine, more specifically in the treatment of cancer or related diseases.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrocarcin A;

glucocorticoïden for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, caminomycin, daunomycin, levamisole, plicamycin, mithramycin;

antimetabolites for example clofarabine, aminopterin, cytosine arabinoside or methotrexate, azacitidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

farnesyltransferase inhibitors for example tipifarnib;

histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;

Inhibitors of the ubiquitin-proteasome pathway for example PS-341, MLN 0.41 or bortezomib;

Yondelis;

Telomerase inhibitors for example telomestatin;

Matrix metalloproteinase inhibitors for example batimastat, marimastat, prinostat or metastat.

Recombinant interleukins for example aldesleukin, denileukin diftitox, interferon alfa 2a, interferon alfa 2b, peginterferon alfa 2b MAPK inhibitors Retinoids for example alitertinoin, bexarotene, tretinoin Arsenic trioxide Asparaginase Steroids for example dromostanolone propionate, megestrol acetate, nandrolone (decanoate, phenpropionate), dexamethasone Gonadotropin releasing hormone agonists or antagonists for example abarelix, goserelin acetate, histrelin acetate, leuprolide acetate Thalidomide, lenalidomide Mercaptopurine, mitotane, pamidronate, pegademase, pegaspargase, rasburicase BH3 mimetics for example ABT-737

MEK inhibitors for example PD98059, AZD6244, CI-1040 colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin.

a steroidal cytochrome P450 17alpha-hydroxylase-17,20-lyase inhibitor (CYP17), e.g. abiraterone, abiraterone acetate.

As stated above, the compounds of the present invention also have therapeutic applications in sensitising tumour cells for radiotherapy and chemotherapy.

Hence the compounds of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

In view of their useful pharmacological properties, the components of the combinations according to the invention, i.e. the one or more other medicinal agent and the compound according to the present invention may be formulated into various pharmaceutical forms for administration purposes. The components may be formulated separately in individual pharmaceutical compositions or in a unitary pharmaceutical composition containing all components.

The present invention therefore also relates to a pharmaceutical composition comprising the one or more other medicinal agent and the compound according to the present invention together with a pharmaceutical carrier.

The present invention further relates to the use of a combination according to the invention in the manufacture of a pharmaceutical composition for inhibiting the growth of tumour cells.

The present invention further relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The anti-tumour anthracycline derivative is advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter ($mg/m^2$) of body surface area, or as known in the art, if different. Trastuzumab is advantageously administered in a dosage of 1 to 5 mg per square meter ($mg/m^2$) of body surface area, particularly 2 to 4 $mg/m^2$ per course of treatment. These dosages may be administered for example once, twice or more per course of treatment, which may be repeated for example every 7, 14, 21 or 28 days.

The compounds of formula (I), the pharmaceutically acceptable addition salts, in particular pharmaceutically acceptable acid addition salts, and stereoisomeric forms thereof can have valuable diagnostic properties in that they can be used for detecting or identifying the formation of a complex between a labelled compound and other molecules, peptides, proteins, enzymes or receptors.

The detecting or identifying methods can use compounds that are labelled with labelling agents such as radioisotopes, enzymes, fluorescent substances, luminous substances, etc. Examples of the radioisotopes include $^{125}I$, $^{131}I$, $^{3}H$ and $^{14}C$. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase. Biological samples can be defined as body tissue or body fluids. Examples of body fluids are cerebrospinal fluid, blood, plasma, serum, urine, sputum, saliva and the like.

The following examples illustrate the present invention.

EXPERIMENTAL PART

Hereinafter, "DMF" is defined as N,N-dimethylformamide, "DCM" is defined as dichloromethane, "DIPE" is defined as diisopropyl ether, 'DMSO' is defined as dimethylsulfoxide, "EtOAc" is defined as ethyl acetate, "EtOH" is defined as ethanol, "MeOH" is defined as methanol and "THF" is defined as tetrahydrofuran.

A. Preparation of the Intermediate Compounds

Example A1 a) Preparation of Intermediate 1

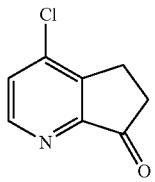

Manganese oxide (33.31 g, 13 Eq, 0.3832 mol) was added portionwise to a solution of 4-chloro-6,7-dihydro-5H-Cyclopenta[b]pyridin-7-ol (intermediate 3) [CAS 126053-15-4] (5 g, 1 Eq, 0.029 mol) in DCM (50 ml). The mixture was stirred at room temperature for 24 hours and then filtered over celite. The solvent was evaporated, yielding 3.25 g (66%) of intermediate 1.

b) Preparation of Intermediate 2

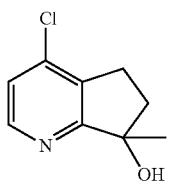

Methylmagnesium chloride (1.47 ml, 3.2 Eq, 0.0.004 mol) was added dropwise to a solution of intermediate 1 (0.220 g, 1 Eq, 0.0013 mol) in THF (4 ml) at −5 to 0° C. under $N_2$ flow. The reaction was stirred at room temperature for 1.5 hours.

At 0-10° C., ammonium chloride (10% in water) and EtOAc were added. The mixture was extracted three times with EtOAc and then the organic layer was separated, dried over MgSO₄, filtered and the solvent was evaporated. The residue (0.215 g) was purified by column chromatography over silica gel (Eluent: cyclohexane/EtOAc 50/50). The pure fractions were collected and the solvent was evaporated, yielding 0.120 g (50%) of intermediate 2.

Example A2 a) Preparation of Intermediate 3

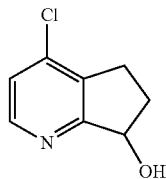 [SMILES: OC1CCc2c(Cl)ccnc21]

Sodium tetrahydroborate (1.92 g, 50.67 mmol) was added portionwise at 5° C. to a solution of intermediate 1 (7.72 g, 46.06 mmol) in MeOH (80 ml). The reaction mixture was stirred at room temperature for 1 night and then poured out into water. The mixture was extracted three times with EtOAc. The organic layer was washed with water and NaCl solution, separated, dried over MgSO₄, filtered and the solvent was evaporated, yielding 6.38 g (81.7%) of intermediate 3 (50/50 mixture RS). This product was used without further purification in the next step.

b) Preparation of Intermediate 4

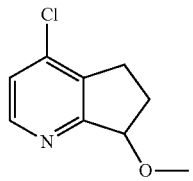

At 0° C. and under $N_2$ atmosphere, sodium hydride (1.06 g, 44.22 mmol) was added portionwise to a solution of intermediate 3 (3.00 g, 17.70 mmol) in THF (anhydrous, 30 ml). The reaction was stirred for 15 minutes at 0° C. Then at 0° C., iodomethane (1.65 ml, 26.53 mmol) was added dropwise to the mixture. The reaction was stirred at room temperature for 1 night. The mixture was cooled to room temperature and cold water was added dropwise. The mixture was stirred for 1 hour and was then extracted with EtOAc three times. The organic layer was separated, dried over MgSO₄, filtered and the solvent was evaporated, yielding 3.10 g (95.4%) of intermediate 4. This product was used without further purification in the next step.

Example A3 a) Preparation of Intermediate 5

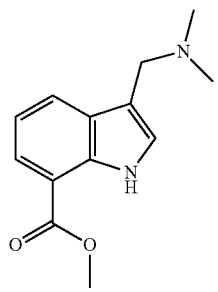 [SMILES: COC(=O)c1cccc2c(CN(C)C)c[nH]c12]

1H-Indole-7-carboxylic acid, methyl ester (0.091 mol), Eschenmoser's salt (0.1 mol) in acetic acid (300 ml) were heated at 65° C. for 2 hours. The precipitate was filtered off, dissolved in DCM and potassium carbonate 10%. Potassium carbonate (solid) was added and the mixture was stirred at room temperature for 1 hour and then extracted. The organic layer was separated, dried over MgSO$_4$, filtered and the solvent was evaporated, yielding 10 g of intermediate 5.

b) Preparation of Intermediate 6

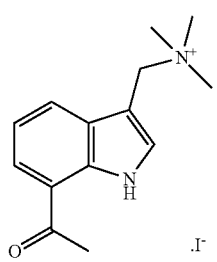 [SMILES: CC(=O)c1cccc2c(C[N+](C)(C)C)c[nH]c12 ; ".I-"]

Intermediate 5 (0.043 mol), iodomethane (0.047 mol) in EtOH (300 ml) were stirred at room temperature overnight. The precipitate was filtered off and dried, yielding 8.3 g of intermediate 6.

c) Preparation of Intermediate 7

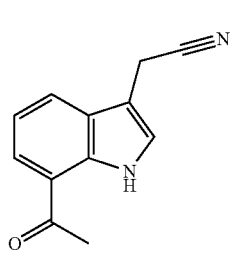

Intermediate 6 (0.023 mol), sodium cyanide (0.03 mol) in DMF (100 ml) were heated at 110° C. for 2 hours. The reaction mixture was poured out into ice water, stirred for 1 hour. The precipitate was filtered off and taken up in DCM. The solution was extracted, the organic layer was separated, dried over MgSO$_4$, filtered and evaporated, yielding 5.1 g of intermediate 7.

d) Preparation of Intermediate 8

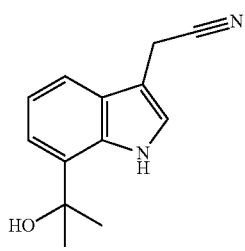 [SMILES: CC(C)(O)c1cccc2c(CC#N)c[nH]c12]

Methylmagnesium chloride (0.058 mol) was added dropwise to a solution of intermediate 7 (0.018 mol) in THF (50 ml) at 5° C. under N$_2$ flow. The reaction mixture was stirred at 5° C. for 1 hour. Ammonium chloride 10% was added dropwise at 5° C. The reaction mixture was extracted with EtOAc. The organic layer was separated, dried over MgSO$_4$, filtered and evaporated, yielding 4 g of intermediate 8.

e) Preparation of Intermediate 9

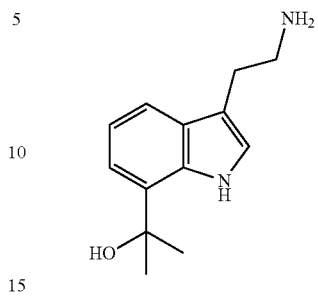

Intermediate 8 (0.019 mol), Raney nickel (4 g) in MeOH/NH$_3$ (50 ml) were hydrogenated at room temperature under 3 bars for 2 hours. The reaction mixture was filtered over celite, washed with DCM and the filtrate was evaporated, yielding 3.5 g of intermediate 9.

f) Preparation of Intermediate 10

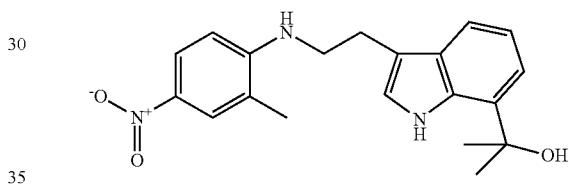

A mixture of intermediate 9 (0.016 mol), 2-fluoro-5-nitrotoluene (0.018 mol), monosodium carbonate anion (0.019 mol) in DMSO (100 ml) was heated at 60° C. overnight. The mixture was cooled to room temperature. Ice water was added, DCM was added. The reaction mixture was extracted, the organic layer was separated, dried over MgSO$_4$, filtered and concentrated. The residue was purified by column chromatography over silica gel (eluent: cyclohexane/EtOAc 60/40). The pure fractions were collected and the solvent was evaporated, yielding 2.8 g of intermediate 10.

g) Preparation of Intermediate 11

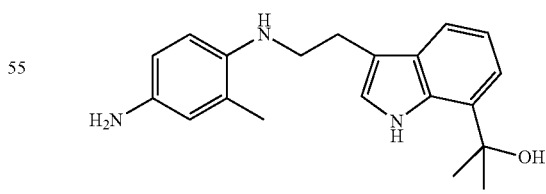

Intermediate 10 (0.0079 mol), vanadium oxide (0.05 g), thiophene (4%) solution in DIPE (1 ml), Pt/C$_5$% (1.3 g) in THF (50 ml) were hydrogenated at atmospheric pressure for 1 night at room temperature. The reaction was filtered and the solvent was evaporated, yielding intermediate 11. This product was used without further purification in the next step.

47

Following intermediates are made according to method A3 intermediate No. 44
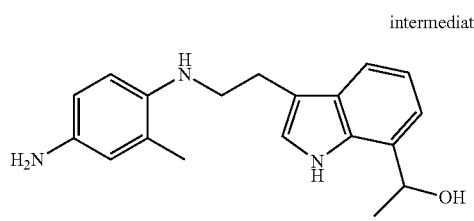

intermediate No. 45
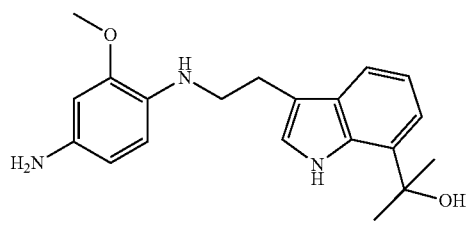

intermediate No. 46
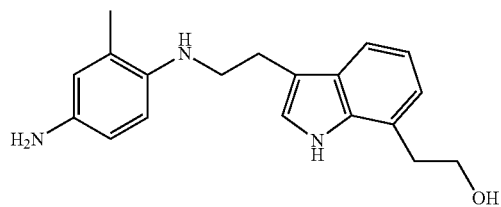

intermediate No. 47
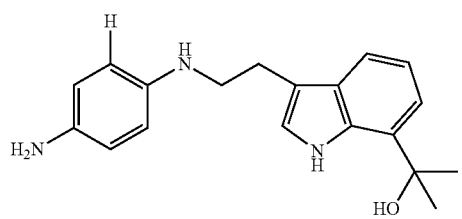

intermediate No. 48
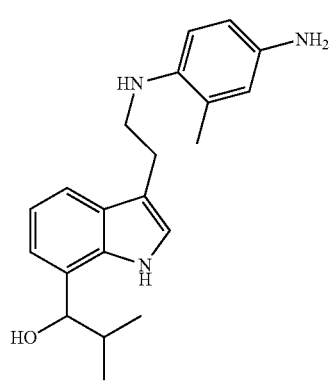

48

-continued intermediate No. 49
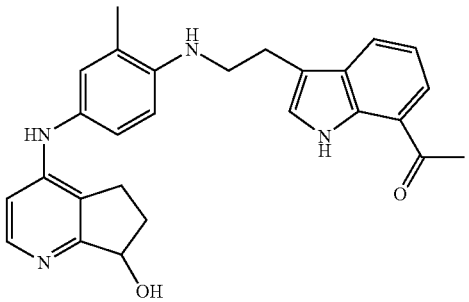

Example A4

Intermediate 7 was also alternatively prepared as follows a) Preparation of Intermediate 12

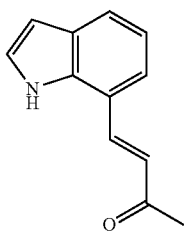

1-(triphenylphosphoranylidene)-2-propanone (34.4 mmol) was added portionwise at room temperature to a solution of 1H-Indole-7-carboxaldehyde (34.44 mmol) in methyl-benzene (60 ml). The reaction mixture was heated at 100° C. for 3 hours and then cooled to room temperature and evaporated to dryness. The residue (17.4 g) was purified by HPLC over silica: 20-45 µm (450 g). (eluent 99.5/0.5 DCM/MeOH). The pure fractions were collected and the solvent was evaporated, yielding 4.3 g of intermediate 12.

b) Preparation of Intermediate 13

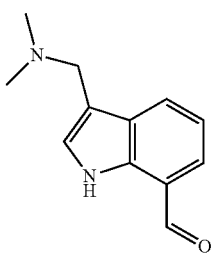

Intermediate 12 (3.4 mmol) and Eschenmoser's salt (3.8 mmol) in acetic acid (10 ml) were heated at 65° C. for 2 hours. The precipitate was filtered off, dissolved in DCM and potassium carbonate 10%. Potassium carbonate (solid) was added and the mixture was stirred at room temperature for 1 hour. The reaction mixture was extracted, the organic layer was separated, dried over MgSO$_4$, filtered and the solvent was evaporated, yielding 0.7 g of intermediate 13.

c) Preparation of Intermediate 14

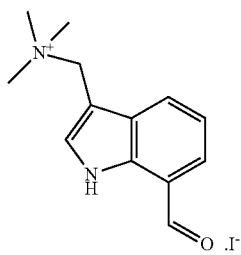

Intermediate 13 (0.13 mol), iodomethane (0.14 mol) in EtOH (300 ml) were stirred at room temperature for 2 days. The precipitate was filtered off and dried, yielding 47 g of intermediate 14.

d) Preparation of Intermediate 15

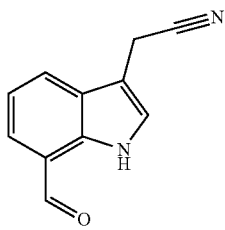 [SMILES: N#CCc1c[nH]c2c(C=O)cccc12]

Intermediate 14 (136.5 mmol), sodium cyanide (177.5 mmol) in DMF (400 ml) were stirred at room temperature for 2 hours. Water was added and the reaction mixture was extracted with EtOAc. The organic layer was separated, dried over MgSO$_4$, filtered and evaporated. The residue was purified by high-performance liquid chromatography (Irregular SiOH 20-45 µm 1000 g MATREX). Mobile phase: cyclohexane 70%/EtOAc 30%). The pure fractions were collected and the solvent was evaporated, yielding 11.8 g of intermediate 15.

e) Preparation of Intermediate 16

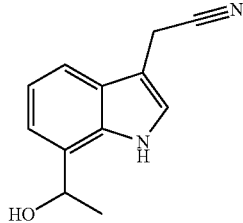

Methylmagnesium chloride (0.07 mol) was added dropwise to a solution of intermediate 15 (0.022 mol) in THF (50 ml). NH$_4$Cl 10% and EOAc were added. The reaction mixture was extracted, the organic layer was separated, dried over MgSO$_4$, filtered and the solvent was evaporated. The residue (2.9 g) was purified by high-performance liquid chromatography (Irregular SiOH 20-45 µm 450 g MATREX). Mobile phase: cyclohexane 60%/EtOAc 40%). The pure fractions were collected and the solvent was evaporated, yielding 2 g of intermediate 16.

f) Preparation of Intermediate 7

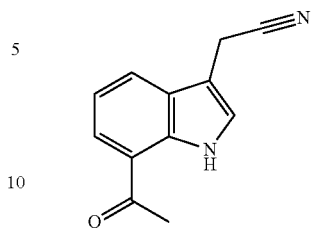

Dess-Martin periodinane (24.9 ml) was added dropwise at room temperature to a solution of intermediate 16 (10 mmol) in DCM (20 ml). The reaction mixture was stirred at room temperature for 1 hour then poured out into ice water, filtered over celite and the filtrate was extracted with DCM. The organic layer was separated, dried over MgSO$_4$, filtered and the solvent was concentrated. The residue (2.8 g) was purified by column chromatography over silica gel (eluent cyclohexane/EtOAc 60/40). The pure fractions were collected and the solvent was evaporated, yielding 0.8 g of intermediate 7.

Example A5

Intermediate 15 was also alternatively prepared as follows.

a) Preparation of Intermediate 17

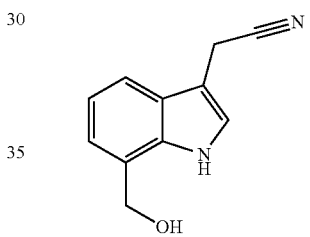

Lithium tetrahydroaluminate (0.018 mol, 0.69 g) was added portionwise to a solution of 3-(cyanomethyl)-1H-Indole-7-carboxylic acid, methyl ester (0.012 mol, 2.6 g) in THF (50 ml) at 5° C. under N$_2$ flow. The reaction mixture was stirred at room temperature for 30 minutes. Water was added dropwise at 5° C. and the reaction mixture was filtered over celite, washed with EtOAc and extracted. The organic layer was separated, dried over MgSO$_4$, filtered and concentrated, yielding 2.4 g of intermediate 17.

b) Preparation of Intermediate 15

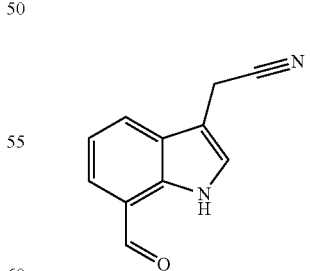

Dess-Martin periodinane (0.016 mol) was added dropwise at 5° C. to a solution of intermediate 17 (0.0081 mol) in DCM (15 ml). The reaction mixture was stirred at room temperature for 2 hours. The reaction mixture was filtered over celite, the filtrate was evaporated. The residue was purified over silica gel by column chromatography (eluent cyclohexane/EtOAc 70/30). The pure fractions were collected and the solvent was evaporated, yielding 0.5 g of intermediate 15.

Example A6

Preparation of Intermediates 18, 19 and 20

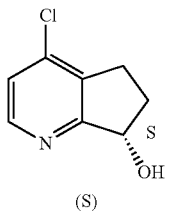
intermediate 18

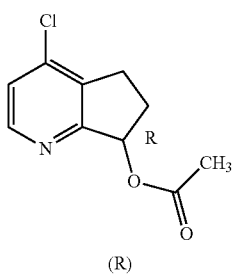
intermediate 19

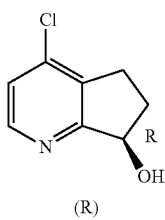
intermediate 20

A mixture of 4-chloro-6,7-dihydro-5H-cyclopenta[b]pyridin-7-ol (5 g, 0.029 mol) and Lipase *Candida Antartica* B (2.5 g) in acetic acid ethenyl ester (50 ml) was stirred at room temperature for 4 hours. The reaction mixture was filtered over Celite. The Celite was washed with DCM. The filtrate's solvent was evaporated. The residue (6.3 g) was purified by column chromatography over silica gel (eluent: DCM/MeOH from 100/0 till 98/2; 15-40 μm). Two different product fractions were collected and the solvent of each product fraction was evaporated, yielding 2.1 g of intermediate 18 (42%; S-enantiomer), and 3.6 g of intermediate 19 (58%; R-enantiomer). When desired intermediate 19 can be converted into the R enantiomer of intermediate 18 by reaction in MeOH/NH₃, yielding intermediate 20.

Intermediates 18 and 20 were also alternatively prepared as follows.

Sodium tetrahydroborate (1.37 g, 36.10 mmol) was added portionwise at 5° C. to a solution of intermediate 1 (5.50 g, 32.82 mmol) in MeOH (50 ml). The reaction mixture was stirred at room temperature for 1 night and then poured out into water and the mixture was extracted three times by EtOAc. The organic layer was washed by water and NaCl solution in water, separated, dried over MgSO₄, filtered and the solvent was evaporated. The residue (4.42 g) was purified by chiral Super critical fluid chromatography on CHIRALPAK AD-H 5 μm 250×20 mm. Mobile phase: 85% CO₂, 15% MeOH.

The pure fractions were collected and the solvent was evaporated, yielding 1.625 g of (29.2%) of compound 18 (S-enantiomer) (DMF, 20° C., concentration 0.33 w/v %, 589 nm: −77.58°) and 1.620 g (29.1%) of compound 20 (R-enantiomer) (DMF, 20° C., concentration 0.33 w/v %, 589 nm: +76.74°).

Example A7

Preparation of Intermediate 21

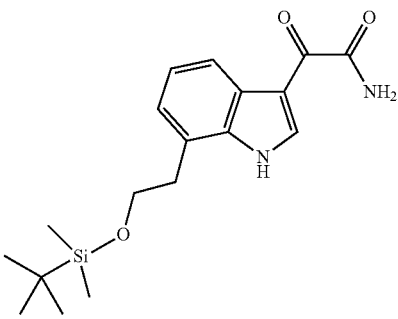 [SMILES: CC(C)(C)[Si](C)(C)OCCc1cccc2c(C(=O)C(N)=O)c[nH]c12]

Oxalyl chloride (0.0079 mol) was added dropwise to 7-[2-[[(1,1-dimethylethyl)dimethylsilyl]oxy]ethyl]-1H-indole (0.0047 mol) in diethyl ether (20 ml) at 5° C. The reaction mixture was stirred at 5° C. for 2 hours. NH₄OH (concentrated, 20 ml) was added dropwise to the solution at 5° C. The reaction mixture was stirred at room temperature overnight. Water and EtOAc were added. The organic layer was separated, dried over MgSO₄, filtered and concentrated, yielding 1.8 g of intermediate 21.

Preparation of Intermediate 22

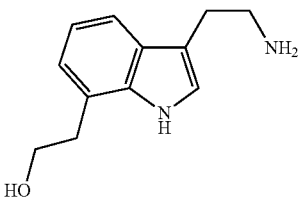 [SMILES: NCCc1c[nH]c2c(CCO)cccc12]

Lithium tetrahydroaluminate (0.021 mol) was added portionwise to a solution of intermediate 21 (0.0052 mol) in THF (50 ml) at 5° C.

The mixture was stirred at reflux overnight then cooled down at 5° C. over ice bath. Excess of lithium tetrahydroaluminate was hydrolyzed cautiously with addition of water dropwise. The mixture was filtered off over celite, washed with DCM and extracted.

The organic layer was separated, dried over MgSO₄, filtered and concentrated, yielding 0.6 g of intermediate 22.

Example A8 a) Preparation of Intermediate 23

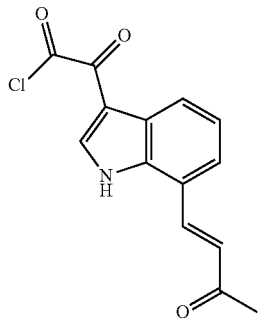 [SMILES: CC(=O)/C=C/c1cccc2c(C(=O)C(=O)Cl)c[nH]c12]

Oxalyl chloride (2.9 mmol) was added dropwise at 5° C. to a solution of 4-(1H-indol-7-yl)-3-buten-2-one (2.7 mmol) in diethyl ether (10 ml). The cold bath was removed and the reaction was allowed to warm to room temperature (1.5 hour). The precipitate was filtered off and dried, yielding 0.49 g of intermediate 23.

b) Preparation of Intermediate 24

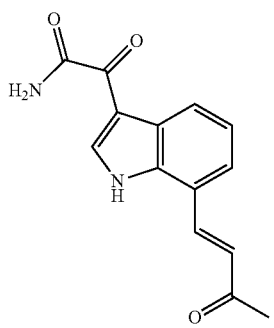 [SMILES: CC(=O)/C=C/c1cccc2c(C(=O)C(N)=O)c[nH]c12]

Ammonium hydroxide (10 ml) was added dropwise to a solution of intermediate 23 (0.725 mmol) in diethyl ether (10 ml) at 5° C. The reaction mixture was stirred at room temperature overnight. The precipitate was filtered off and dried, yielding 0.11 g of intermediate 24.

c) Preparation of Intermediate 25

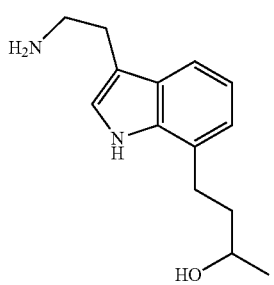 [SMILES: CC(O)CCc1cccc2c(CCN)c[nH]c12]

Lithium tetrahydroaluminate (39.5 mmol) was added portionwise to a solution of intermediate 24 (7.9 mmol) in THF (20 ml) at 5° C. The mixture was stirred at 80° C. for 2 hours then cooled down at 5° C. over ice bath. Excess of lithium tetrahydroaluminate was hydrolyzed cautiously with addition of water dropwise. The mixture was filtered off over celite, washed with DCM and extracted. The organic layer was separated, dried over MgSO$_4$, filtered and concentrated, yielding 1 g of intermediate 25.

d) Preparation of Intermediate 26

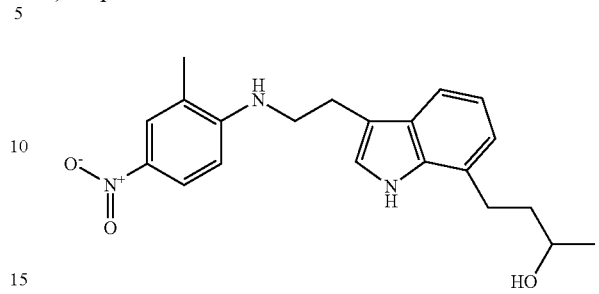

A mixture of intermediate 25 (4.3 mmol), 2-fluoro-5-nitrotoluene (4.7 mmol), monosodium carbonate anion (5.1 mmol) in DMSO (10 ml) was heated at 60° C. overnight. The mixture was cooled to room temperature. Ice water was added, DCM was added. The reaction mixture was extracted, the organic layer was separated, dried over MgSO$_4$, filtered and evaporated. The residue was purified by column chromatography (eluent: DCM/MeOH 97/3). The pure fractions were collected and the solvent was evaporated. The residue was purified by high-performance liquid chromatography (Irregular SiOH 15-40 µm 300 g MERCK). Mobile phase (NH$_4$OH 0.1%-dichloromethane 99%-MeOH 1%). The pure fractions were collected and the solvent was evaporated, yielding 200 mg of intermediate 26.

e) Preparation of Intermediate 27

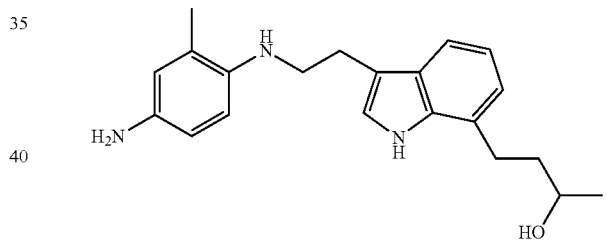

A mixture of intermediate 26 (0.35 mmol), Raney nickel (200 mg) in MeOH (5 ml) was hydrogenated under atmospheric pressure at room temperature. The residue was filtered over celite, washed with DCM and the residue was evaporated, yielding 0.14 g of intermediate 27.

Example A9 a) Preparation of Intermediate 28

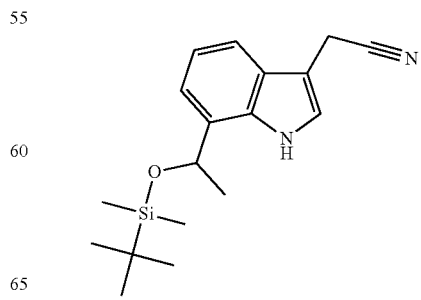

Tert-butyldimethylsilyl chloride (195 mg, 0.91 mmol) was added to a solution of intermediate 16 (162 mg, 0.81 mmol), imidazole (143 mg, 2.1 mmol) in THF (5 ml) at room temperature. The reaction mixture was stirred at room temperature overnight. The precipitate was filtered off and washed with DCM. The filtrate was evaporated. The residue (365 mg) was purified by flash chromatography over silica gel (15-40 μm, 30 g, DCM/MeOH:100/0 to 99/1). The pure fractions were collected and evaporated to dryness, yielding 190 mg of intermediate 28.

b) Preparation of Intermediate 29

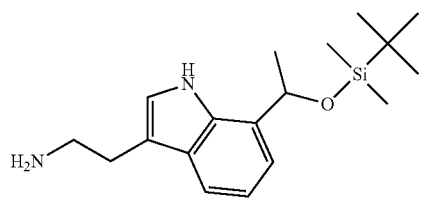 [SMILES: CC(O[Si](C)(C)C(C)(C)C)c1cccc2c(CCN)c[nH]c12]

Intermediate 28 (190 mg, 0.6 mmol), Raney nickel (0.7 g) in $NH_3$ in MeOH 7N (10 ml) were stirred at room temperature under 3 bars of $H_2$ for 4 hours. The reaction was filtered over celite and the celite was washed with DCM/MeOH (90/10) three times. The solvent was evaporated to give 147 mg of intermediate 29.

c) Preparation of Intermediate 30

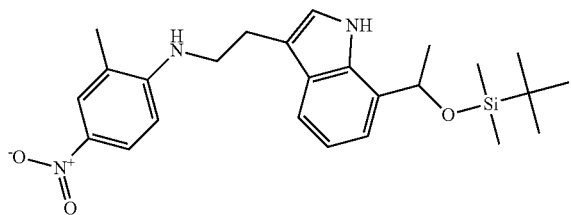

A mixture of intermediate 29 (147 mg, 0.46 mmol), 1-fluoro-2-methyl-4-nitro-benzene (78 mg, 0.51 mmol), carbonic acid sodium salt (1:1) (85 mg, 1 mmol) in DMSO (2 ml) was heated at 65° C. for 1 night. The mixture was poured into ice and stirred 10 minutes, DCM was added and the mixture was extracted with DCM twice. The organic layer was washed with water then was dried over $MgSO_4$, filtered and the solvent was evaporated. The residue was purified by flash chromatography over silica gel (15-40 μm, 30 g, cyclohexane/EtOAc 85/15). The pure fractions were collected and evaporated to dryness, yielding 200 mg of intermediate 30.

d) Preparation of Intermediate 31

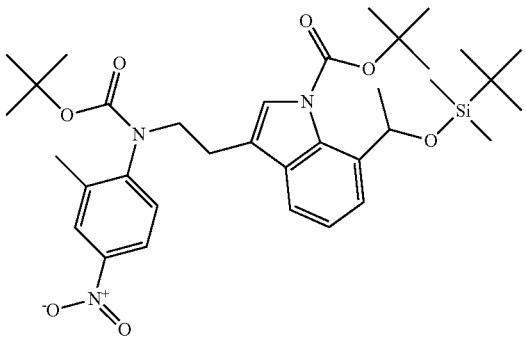

Intermediate 30 (2.8 g, 6.17 mmol), di-tert-butyl dicarbonate (8 g, 37 mmol), 4-dimethylaminopyridine (0.15 g, 1.2 mmol) and triethylamine (1.89 ml, 13.6 mmol) in THF (50 ml) were stirred for 24 hours at 60° C. The mixture was evaporated to dryness. The residue (7.4 g) was purified by high-performance liquid chromatography on silica gel (Cartridge 15-40 μm, 90 g). Mobile phase (cyclohexane 50%; dichloromethane 50%). The pure fractions were collected and the solvent was evaporated, yielding 3.3 g of intermediate 31.

e) Preparation of Intermediate 32

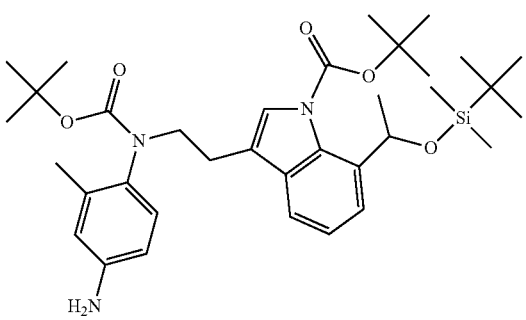 [SMILES: Cc1cc(N)ccc1N(CCc1cn(C(=O)OC(C)(C)C)c2c(C(C)O[Si](C)(C)C(C)(C)C)cccc12)C(=O)OC(C)(C)C]

A mixture of intermediate 31 (3.3 g, 5 mmol), Raney nickel (3 g) in MeOH (100 ml) was hydrogenated at 2.5 bars for 2 hours. The residue was filtered over celite, washed with DCM and the residue was evaporated, yielding 2.7 g of intermediate 32.

f) Preparation of Intermediate 33

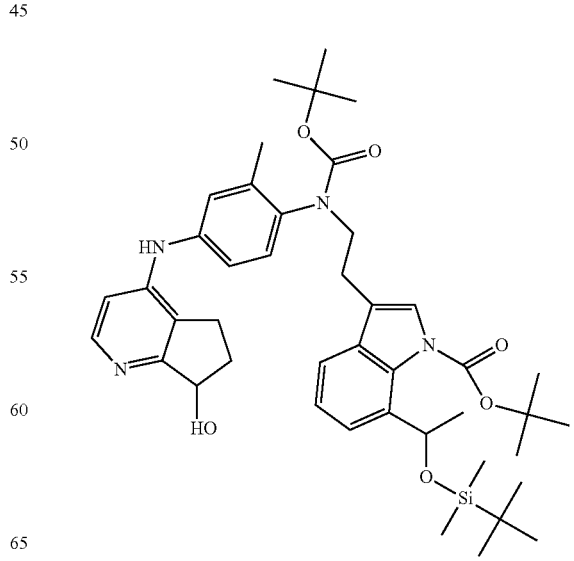

Intermediate 32 (2.6 g, 4.2 mmol), 4-chloro-6,7-dihydro-5H-cyclopenta[b]pyridin-7-ol (0.78 g, 4.6 mmol), HCl 4M in dioxane (0.21 ml, 0.8 mmol) in acetonitrile (28 ml) and EtOH (7 ml) were heated at 65° C. for 72 hours. After cooling down to room temperature, water and potassium carbonate powder were added and the mixture was extracted twice with EtOAc. The organic layer was washed with water, dried over MgSO₄, filtered and evaporated. The residue was purified by high-performance liquid chromatography (Irregular SiOH 20-45 μm 450 g MATREX). Mobile phase (NH₄OH 0.5%; dichloromethane 95%; MeOH 5%). The pure fractions were collected and the solvent was evaporated, yielding 2.35 g of intermediate 33.

g) Preparation of Intermediate 34

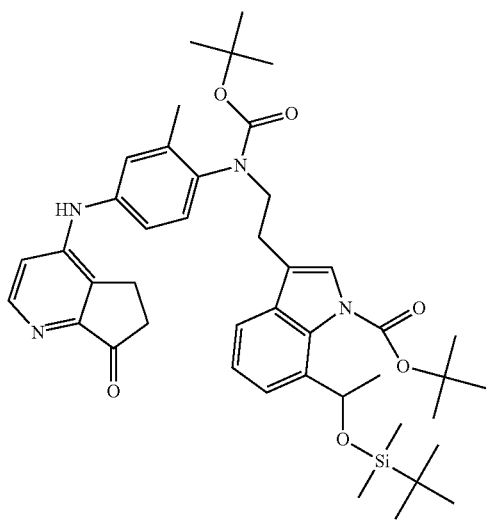 [SMILES: Cc1cc(Nc2ccnc3c2CCC3=O)ccc1N(CCc1cn(C(=O)OC(C)(C)C)c2c(C(C)O[Si](C)(C)C(C)(C)C)cccc12)C(=O)OC(C)(C)C]

Manganese (IV) oxide (4.3 g) was added portionwise to intermediate 33 (2.2 g, 2.9 mmol) and tris(2-(2-methoxyethoxy)ethyl)amine (47 mg, 0.145 mmol) in solution at room temperature in DCM (50 ml). The mixture was stirred at room temperature for 18 hours. The mixture was filtered over celite. Celite was washed with DCM and the solvent evaporated, yielding 1.84 g of intermediate 34.

h) Preparation of Intermediate 35

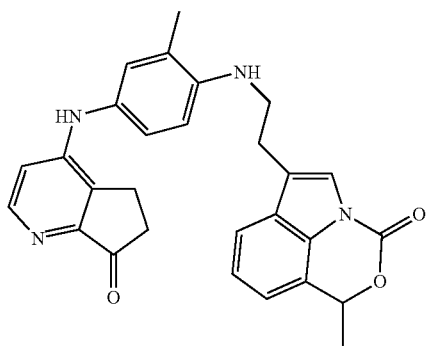 [SMILES: Cc1cc(Nc2ccnc3c2CCC3=O)ccc1NCCc1cn2c3c(cccc13)C(C)OC2=O]

Intermediate 34 (1.2 g, 1.6 mmol) in trifluoroacetic acid (1.2 ml, 15.9 mmol) and DCM (10 ml) was stirred at room temperature for 2 days. Potassium carbonate 10% was added and the mixture was extracted twice with DCM. The organic layer was dried over MgSO₄, filtered and evaporated to give 0.8 g of intermediate 35, used without further purification for the next step.

Example A10 a) Preparation of Intermediate 36

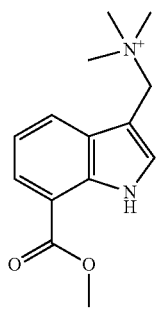 [SMILES: COC(=O)c1cccc2c(C[N+](C)(C)C)c[nH]c12]

Iodomethane (0.024 mol) was added to a solution of 3-[(dimethylamino)methyl]-1H-indole-7-carboxylic acid, methyl ester (0.022 mol) in EtOH (50 ml). The mixture was stirred at room temperature overnight, then concentrated in vacuo till dryness, yielding 5.6 g (68%) of intermediate 36.

b) Preparation of Intermediate 37

A mixture of intermediate 36 (0.015 mol) and sodium cyanide (0.019 mol) in DMF (60 ml) was stirred at 100° C. for 2 hours. Water was added. The precipitate was filtered. The filtrate was evaporated, yielding 3.5 g (100%) of intermediate 37.

c) Preparation of Intermediate 38

A mixture of intermediate 37 (0.016 mol) and Raney nickel (3 g) in MeOH/NH₃ (50 ml) was hydrogenated at room temperature under a 3 bar pressure, then filtered over celite. The filtrate was evaporated, yielding 3.2 g (89%) of intermediate 38.

d) Preparation of Intermediate 39

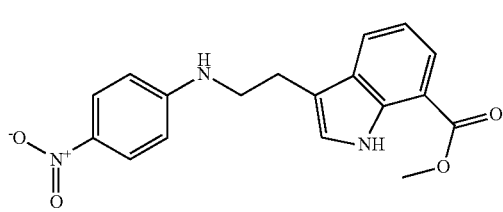

A mixture of intermediate 38 (0.0092 mol), 1-fluoro-4-nitro-benzene (0.01 mol) and diisopropylethylamine (0.023 mol) was stirred at 180° C. for 2 hours. Water was added. The mixture was extracted with DCM. The organic layer was separated, dried (MgSO$_4$), filtered and the solvent was evaporated. The residue (2.6 g) was purified by column chromatography over kromasil (eluent: cyclohexane/EtOAc 60/40). The pure fractions were collected and the solvent was evaporated, yielding 1.4 g (45%) of intermediate 39.

e) Preparation of Intermediate 40

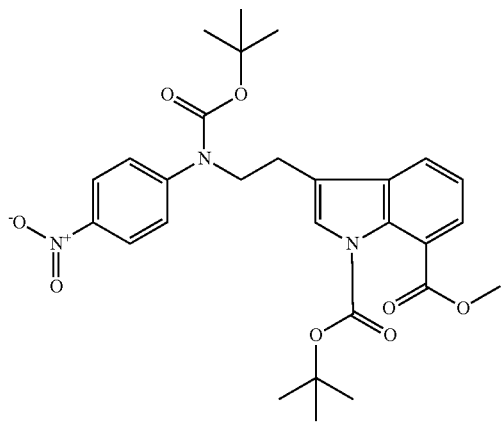

Tert-butoxycarbonyl anhydride (0.015 mol) was added at room temperature to a mixture of intermediate 39 (0.05 mol) and 4-(dimethylamino)pyridine (few) in THF (50 ml). The mixture was stirred at room temperature overnight. The mixture was extracted with EtOAc. The organic layer was washed with water, dried (MgSO$_4$), filtered and the solvent was evaporated. The residue (4 g) was purified by column chromatography over silica gel (eluent: cyclohexane/EtOAc 60/40). The pure fractions were collected and the solvent was evaporated, yielding 3.3 g (82%) of intermediate 40.

f) Preparation of Intermediate 41

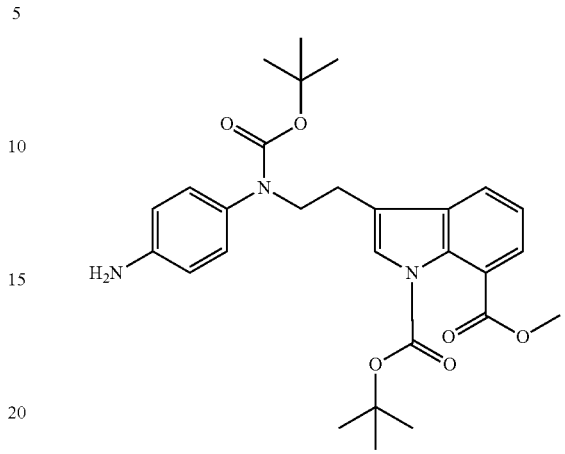

A mixture of intermediate 40 (0.0061 mol) and Raney nickel (3.3 g) in MeOH (50 ml) was hydrogenated at room temperature under a 3 bar pressure, then filtered over celite. Celite was washed with DCM/MeOH (98/2). The filtrate was evaporated. The residue (2.8 g) was purified by column chromatography over silica gel (eluent: cyclohexane/EtOAc 70/30). The pure fractions were collected and the solvent was evaporated, yielding 1.3 g (42%) of intermediate 41.

g) Preparation of Intermediate 42

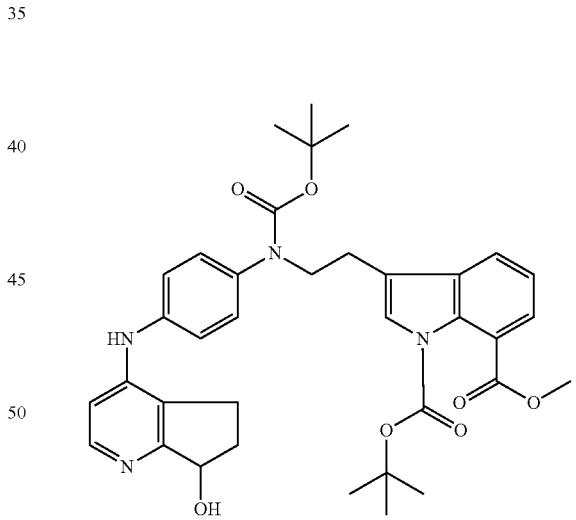

A mixture of intermediate 41 (0.0018 mol), 4-chloro-6,7-dihydro-5H-cyclopenta[b]pyridin-7-ol (0.33 g) and HCl/isopropanol (5 drops) in acetonitrile (20 ml) was stirred at 65° C. for 24 hours. Potassium carbonate 10% was added. The mixture was extracted with EtOAc. The organic layer was separated, dried (MgSO$_4$), filtered and the solvent was evaporated. The residue (1.1 g) was purified by column chromatography over silica gel (eluent: DCM/MeOH/NH$_4$OH 95/5/0.1). The pure fractions were collected and the solvent was evaporated, yielding 0.054 g of intermediate 42.

h) Preparation of Intermediate 43

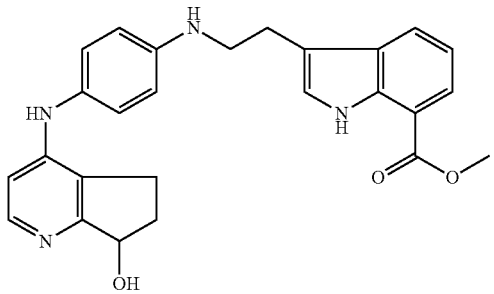 [SMILES: COC(=O)c1cccc2c(CCNc3ccc(Nc4ccnc5c4CCC5O)cc3)c[nH]c12]

A mixture of intermediate 42 (0.0009 mol) and HCl 3N (0.0039 mol) in acetonitrile (10 ml) was stirred at 65° C. for 3 hours. Potassium carbonate 10% was added. The mixture was extracted with EtOAc. The organic layer was separated, dried (MgSO$_4$), filtered and the solvent was evaporated. The residue (0.4 g, 100%) was crystallized from diethyl ether/acetonitrile. The precipitate was filtered off and dried, yielding 0.3 g of intermediate 43, melting point 164° C.

B. Preparation of the Final Compounds

Example B1

Preparation of Compound 1

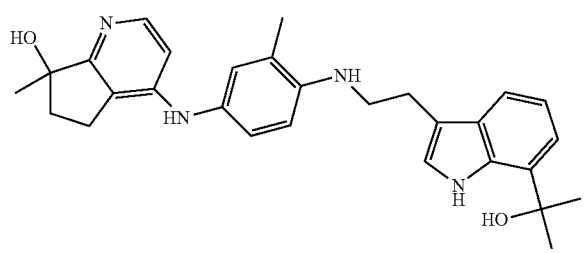 [SMILES: Cc1cc(Nc2ccnc3c2CCC3(C)O)ccc1NCCc1c[nH]c2c(C(C)(C)O)cccc12]

Intermediate 11 (1.00 g, 3.092 mmol), intermediate 2 (0.437 g, 2.381 mmol), HCl (0.155 ml, 0.618 mmol) in acetonitrile (10 ml) were stirred for 5 hours at 65° C. The reaction was cooled to room temperature and then basified by potassium carbonate (10% in water) and extracted with DCM three times. The organic layer was washed by water, dried over MgSO$_4$, filtered and the solvent was evaporated. The residue (1.37 g) was purified by Normal phase over silica 5 μm 150×30.0 mm) Mobile phase (Gradient from 0% NH$_4$OH, 100% DCM, 0% MeOH to 0.8% NH$_4$OH, 92% DCM, 8% MeOH) The pure fractions were collected and the solvent was evaporated. The residue (0.350 g) was taken up into acetonitrile for 1 week at room temperature. This product crystallized and was filtered and dried under vacuum, yielding 300 mg (20.8%) of compound 1, melting point 209° C.

Example B2

Preparation of Compounds 2 and 3

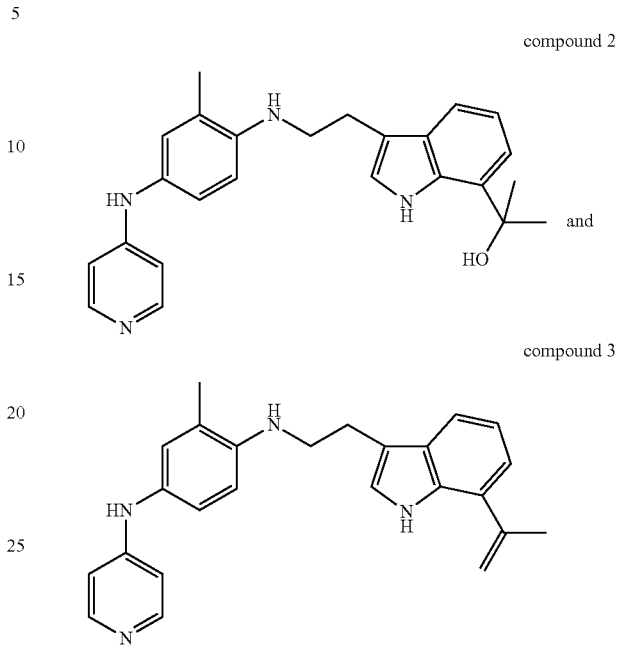

A solution of intermediate 11 (0.0031 mol), N,N-diisopropylethylamine (0.0028 mol), 4-bromopyridine hydrochloride (0.0034 mol) in acetonitrile (20 ml) was heated at 65° C. for 6 hours. Potassium carbonate 10% and EtOAc were added. The reaction mixture was extracted, the organic layer was separated, dried over MgSO$_4$, filtered and concentrated. The residue (1.3 g) was purified by column chromatography over silica gel (eluent 95/5/0.5 DCM/MeOH/NH$_4$OH). Two fractions were collected and the solvent was evaporated to give 60 mg of compound 3 and 80 mg of F2. The residue F2 (80 mg) was purified by supercritical fluid chromatography (AMINO column 150×21.2 mmm) eluent: MeOH/CO$_2$ 30/70). The pure fractions were collected and the solvent was evaporated, yielding 43 mg of compound 2.

Example B3

Preparation of Compound 4

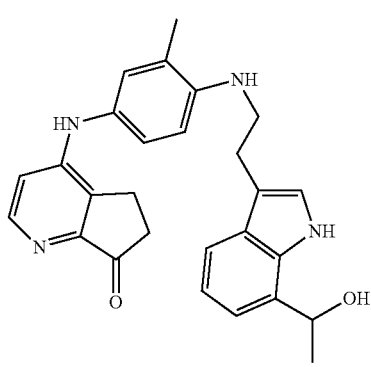 [SMILES: Cc1cc(Nc2ccnc3c2CCC3=O)ccc1NCCc1c[nH]c2c(C(C)O)cccc12]

Intermediate 35 (0.8 g, 1.7 mmol) and sodium hydroxide 3N (2.57 ml, 2.57 mmol) in EtOH (22 ml) and THF (10 ml)

were stirred at room temperature for 30 minutes. NH₄Cl 10% and DCM were added and the mixture was filtered over Celite. The organic layer was decanted, dried over MgSO₄, filtered and evaporated. The residue was purified by Normal phase over Spherical SiOH 10 μm 60 g PharmPrep MERCK). Mobile phase (NH4OH 0.1%, 95% DCM, 5% MeOH). The pure fractions were collected and the solvent was evaporated, yielding 250 mg of compound 4.

Example B4

Preparation of Compound 5

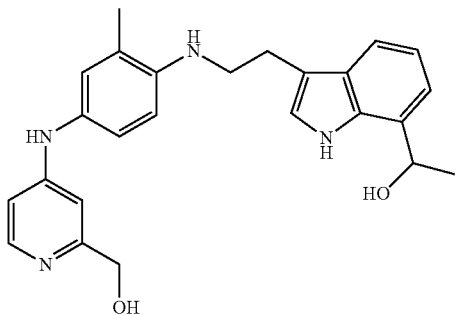 [SMILES: Cc1cc(Nc2ccnc(CO)c2)ccc1NCCc1c[nH]c2c(C(C)O)cccc12]

Sodium tetrahydroborate (0.69 mmol) was added to a solution of intermediate 49 (0.46 mmol) in MeOH (5 ml) at 5° C. The reaction mixture was stirred at room temperature overnight. Water was added, the reaction mixture was extracted with EtOAc, the organic layer was separated, dried over MgSO₄, filtered and evaporated. The residue (0.14 g) was crystallized in acetonitrile, the precipitate was filtered off and dried, yielding 0.1 g of compound 5.

Example B5

Preparation of Compound 6

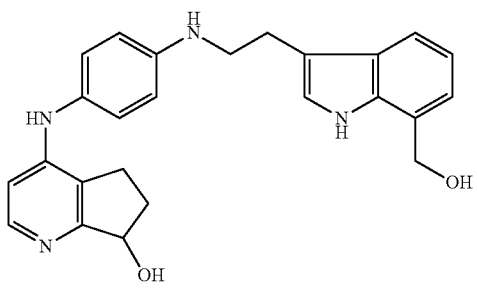 [SMILES: OCc1cccc2c(CCNc3ccc(Nc4ccnc5c4CCC5O)cc3)c[nH]c12]

Lithium tetrahydroaluminate (0.0003 mol) was added portionwise at 5° C. to a solution of intermediate 43 (0.0002 mol) in THF (4 ml) under N₂ flow. The mixture was stirred at room temperature for 2 hours. Water was added. The mixture was extracted with EtOAc. The organic layer was separated, dried (MgSO₄) filtered and the solvent was evaporated. The residue (0.18 g) was purified by column chromatography over kromasil (eluent: DCM/MeOH/NH₄OH 98/2/0.2 to 85/15/1; 3.5 μm). The pure fractions were collected and the solvent was evaporated, yielding 0.066 g (70%) of compound 6.

Example B6

Preparation of Compounds 7 and 8

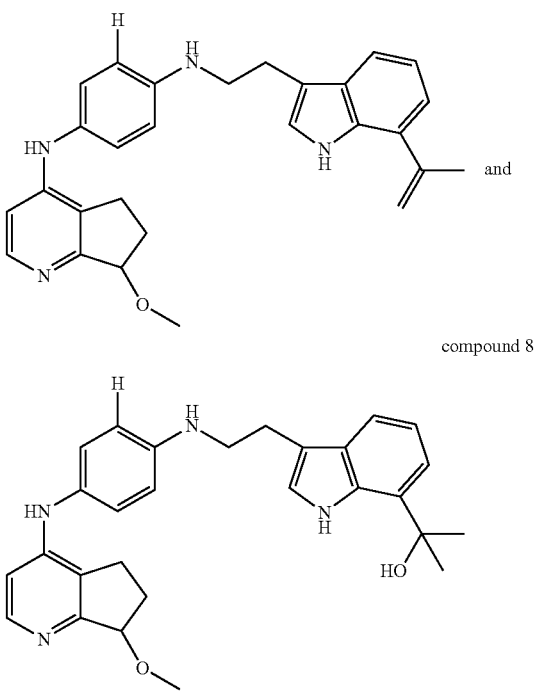

Intermediate 47 ((1.00 g, 3.23 mmol), intermediate 4 (0.653 g, 3.55 mmol), HCl/dioxane (0.242 ml, 0.97 mmol) in acetonitrile (15 ml) were stirred for 1 night at 70° C. The reaction mixture was cooled to room temperature. Water then potassium carbonate (10% in water) were added. The mixture was extracted three times with DCM. The organic layer was separated, dried over MgSO₄, filtered and the solvent was evaporated. The residue was purified by Normal phase over silica gel (Cartridge 15-40 μm 30 g). Mobile phase (96% DCM, 4% MeOH) The pure fractions were collected and the solvent was evaporated, yielding 0.092 g (6.5%) of compound 7 and 0.030 g of (2.0%) of compound 8.

Example B7

Preparation of Compound 9

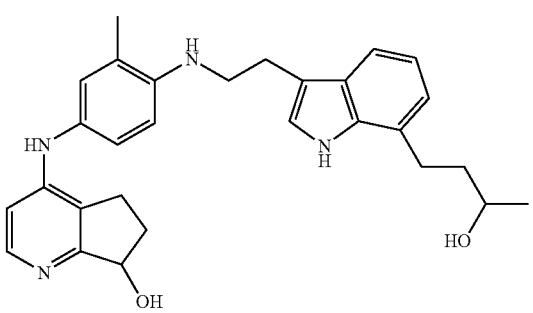 [SMILES: Cc1cc(Nc2ccnc3c2CCC3O)ccc1NCCc1c[nH]c2c(CCC(C)O)cccc12]

Intermediate 27 (0.41 mmol) and 4-chloro-6,7-dihydro-5H-cyclopenta[b]pyridin-7-ol (0.46 mmol) were heated at 125° C. for 2 hours. The residue was purified by column chromatography over silica gel (eluent 90/10/0.1 DCM/MeOH/NH₄OH). The pure fractions were collected and the solvent was evaporated, yielding 58 mg of compound 9.

Example B8

Preparation of Compounds 24 and 25

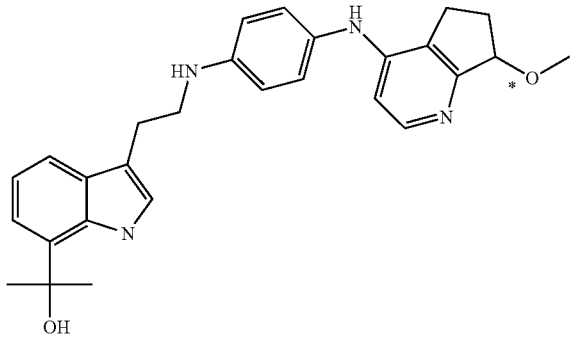

Co.No.24: *S
Co.No.25: *R

*means relative stereochemistry (absolute stereochemistry not known). So if compound 24 is the S enantiomer than compound 25 is the R enantiomer or if compound 24 is the R enantiomer than compound 25 is the S enantiomer The reaction was performed under N₂ atmosphere.

A mixture of intermediate 47 (11.31 mmol), intermediate 4 (12.44 mmol), Pd(dba)₂ (1.13 mmol), BINAP (1.13 mmol) and tBuONa (22.62 mmol) in toluene (100 ml) was stirred at reflux overnight. The mixture was filtered, wash with MeOH and purified by high-performance liquid chromatography (column Synergi 50*250 mm, 10 μm; eluent: CH₃CN/H₂O (0.1% trifluoroacetic acid) gradient of 15% CH₃CN at time 0 min to 40% CH₃CN at time 25 min) The desired fraction was collected and the solvent was evaporated in vacuo. The residue was extracted with DCM, washed with aqueous NaHCO₃, dried over Na₂SO₄, filtered and evaporated to give compound 8 (3.8 g, 98% purity, 65% yield), which was separated by Supercritical Fluid Chromatography Chiralcel OJ, 20 μm, 250 mm*20 mm; Supercritical CO₂: isopropanol (0.05% diethylamine), 40:60 v/v, 70 ml/min) to give two fractions; 1000.79 mg (19%) of compound 24, melting point 110.5-111.6° C.

(ee %=99%, $[\alpha]_D^{20}$=+5.034°, (wavelength=589, 20° C. in methanol, concentration 10.33 mg/ml).

and 939.19 mg (18%) of compound 25, melting point 111.4-113.3° C.

(ee %=99%, $[\alpha]_D^{20}$=−3.443°, (wavelength=589, 20° C. in MeOH, concentration 10.74 mg/ml).

Example B9

Preparation of Compounds

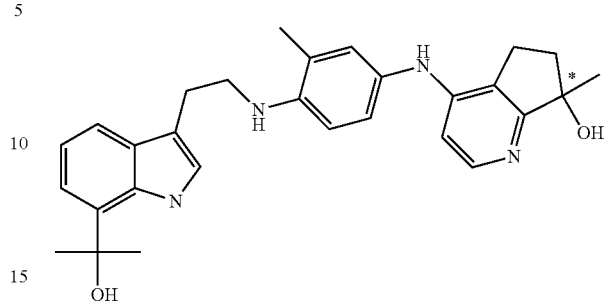

Co.No.26: *S
Co.No.27: *R

*means relative stereochemistry (absolute stereochemistry not known). So if compound 26 is the S enantiomer than compound 27 is the R enantiomer or if compound 26 is the R enantiomer than compound 27 is the S enantiomer Reaction was performed under N₂ atmosphere.

A mixture of intermediate 11 (9.25 mmol), intermediate 2 (9.25 mmol), tBuONa (18.5 mmol), Pd(dba)₂ (0.93 mmol) and BINAP (0.93 mmol) in toluene (40 ml) was heated to reflux and stirred for 3 hours. The resulting mixture was cooled to room temperature and filtered. The filtration was evaporated in vacuo and the residue was purified by high performance liquid chromatography (column Synergi 50*250 mm, 10 μm; eluent: CH₃CN/H₂O (0.1% trifluoroacetic acid) gradient of 10% CH₃CN at time 0 min to 40% CH₃CN at time 25 min) The desired fractions were collected and adjust to pH>7. The solvent was concentrated and extracted with ethyl acetate (3 times 100 ml) and desired organic layers were washed with brine, dried over Na₂SO₄, filtered and the solvent was evaporated in vacuo to get 2.5 g (57%) of compound 1 which was separated by Supercritical Fluid Chromatography (AD 250 mm*20 mm, 20 μm; Supercritical CO₂: isopropanol (0.05% diethylamine) 40:60, v/v, 70 ml/min) to give 2 fractions. Fraction 1 (1 g) was further purified by high performance liquid chromatography (column Synergi 50*250 mm, 10 μm; eluent: CH₃CN/H₂O (0.1% trifluoroacetic acid) gradient of 10% CH₃CN at time 0 min to 40% CH₃CN at time 25 min) to give 0.88 g (20%) compound No. 26, melting point 122.3-124° C., (ee=100%).

Fraction 2 (1 g) was further purified by high performance liquid chromatography (column Synergi 50*250 mm, 10 μm; eluent: CH₃CN/H₂O (0.1% trifluoroacetic acid) gradient of 10% CH₃CN at time 0 min to 40% CH₃CN at time 25 min) to give 0.96 g (22%) of compound 27, melting point 121.4-122.6° C., (ee=99%).

Table 1 lists the compounds that were prepared according to one of the above Examples.

TABLE 1

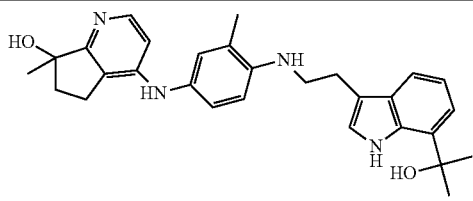

Co. No. 1; Ex. [B1];

TABLE 1-continued
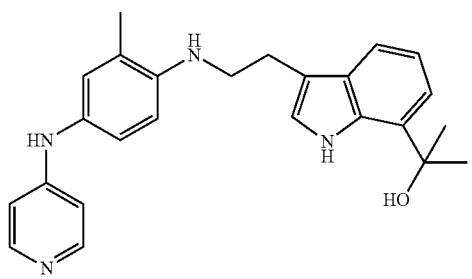
Co. No. 2; Ex. [B2];
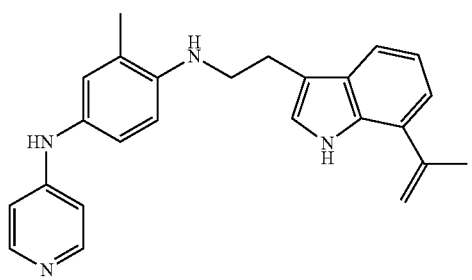
Co. No. 3; Ex. [B2];
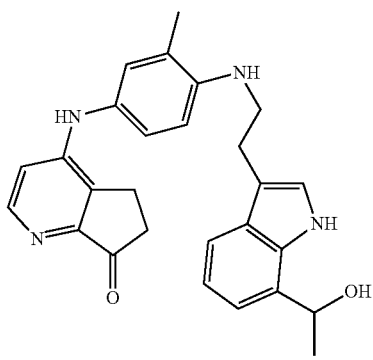
Co. No. 4; Ex. [B3];
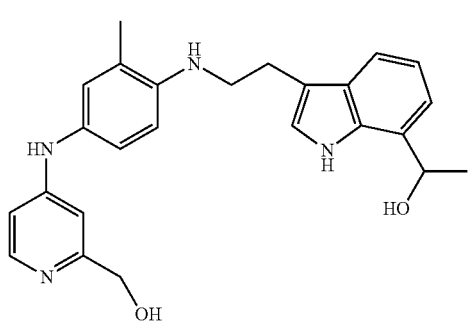
Co. No. 5; Ex. [B4];
TABLE 1-continued
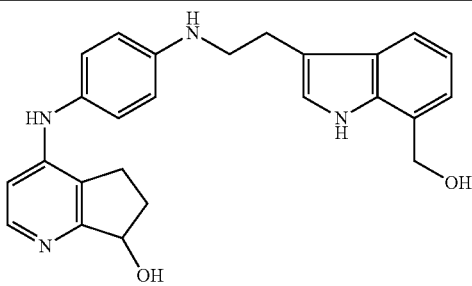
Co. No. 6; Ex. [B5];
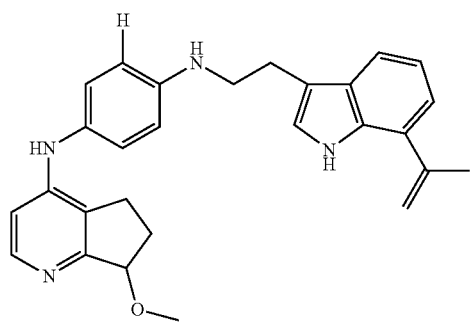
Co. No. 7; Ex. [B6];
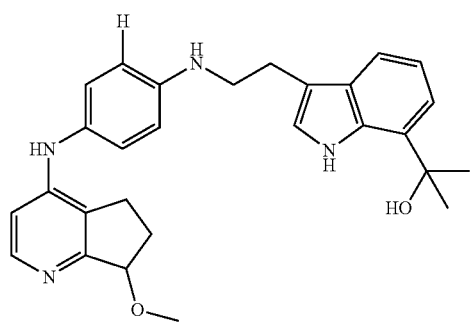
Co. No. 8; Ex. [B6];
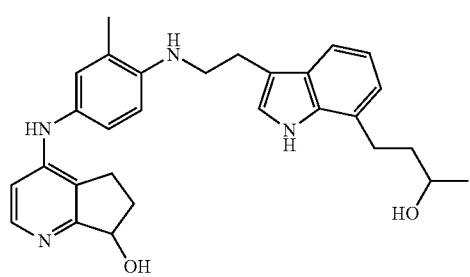
Co. No. 9; Ex. [B7];
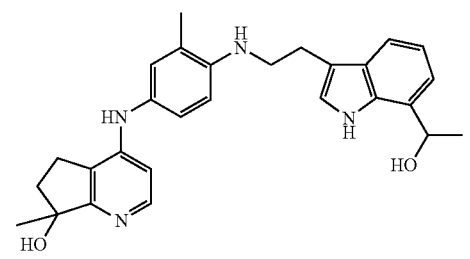
Co. No. 10; Ex. [B1];

TABLE 1-continued
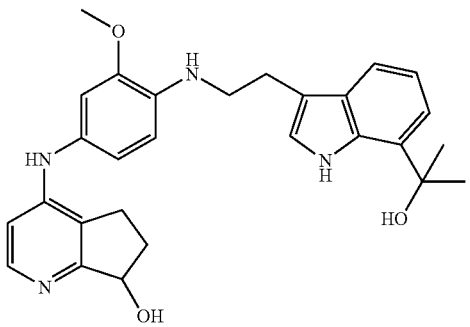
Co. No. 11; Ex. [B1];
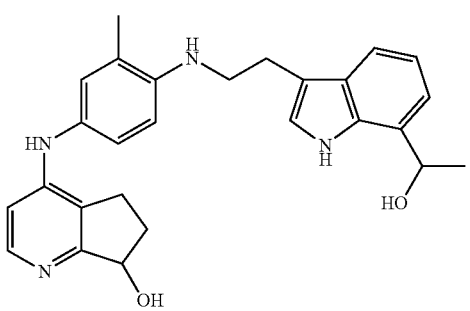
Co. No. 12; Ex. [B1];
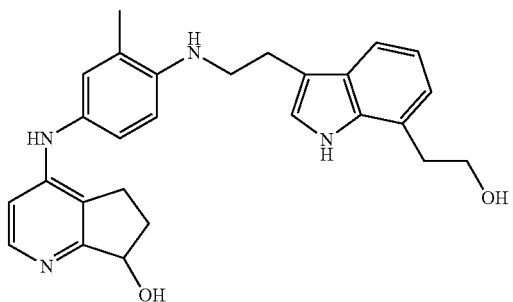
Co. No. 13; Ex. [B1];
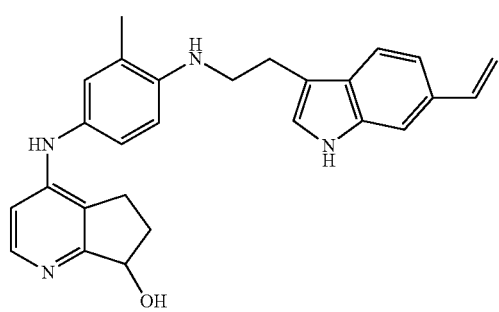
Co. No. 14; Ex. [B1];
TABLE 1-continued
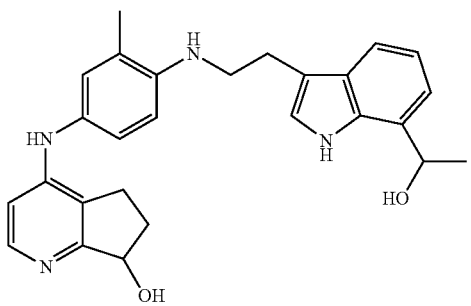
Co. No. 15; Ex. [B1];
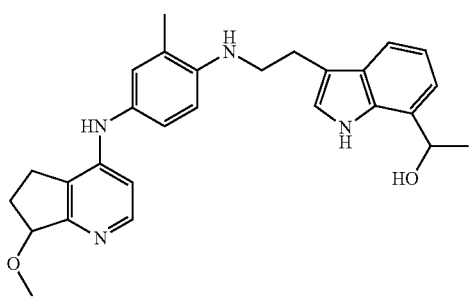
Co. No. 16; Ex. [B1];
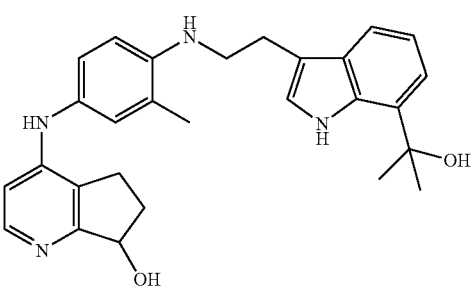
Co. No. 17; Ex. [B1];
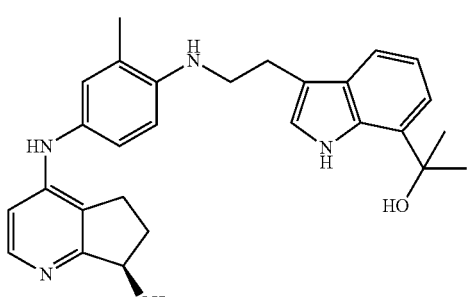
Co. No. 18; Ex. [B1];

TABLE 1-continued
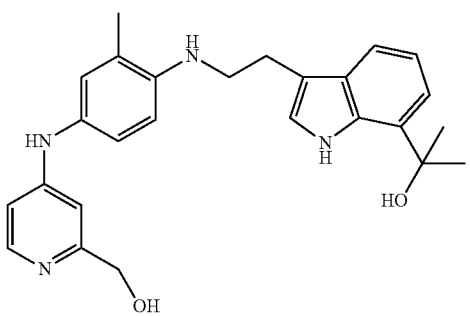
Co. No. 19; Ex. [B1];
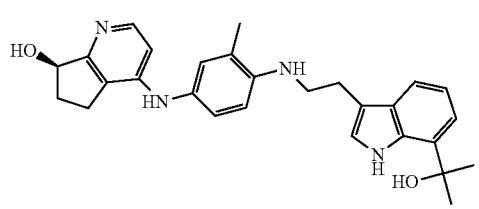
Co. No. 20; Ex. [B1];
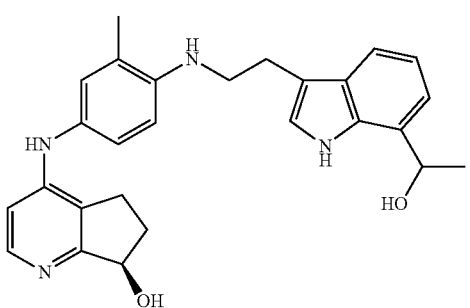
Co. No. 21; Ex. [B1];
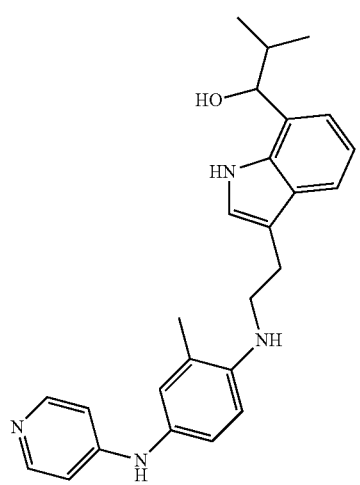
Co. No. 22; Ex. [B2];
TABLE 1-continued
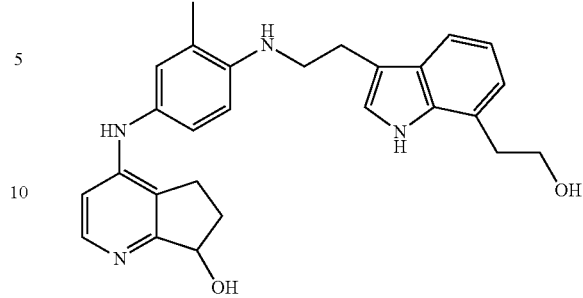
Co. No. 23; Ex. [B1];
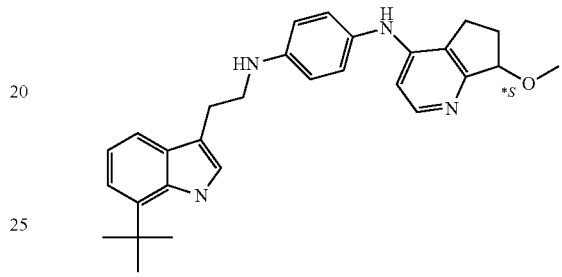
Co. No. 24; Ex. [B8]
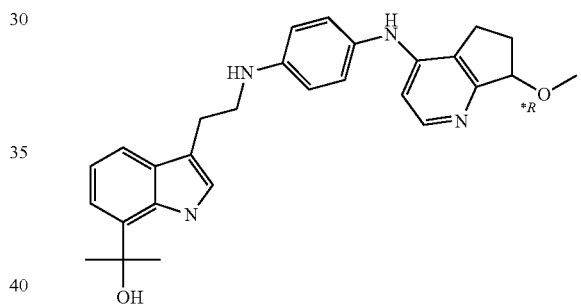
Co. No. 25; Ex. [B8]
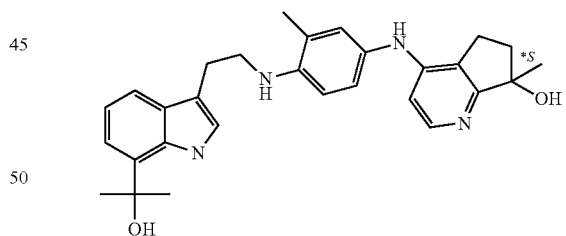
Co. No. 26; Ex. [B9]
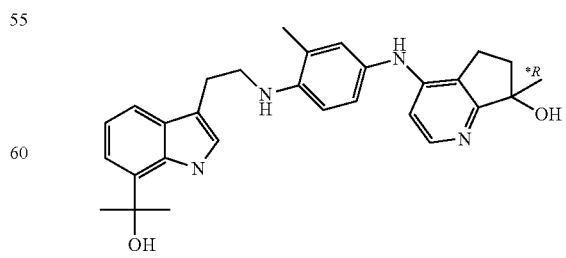
Co. No. 27; Ex. [B9]

TABLE 1-continued

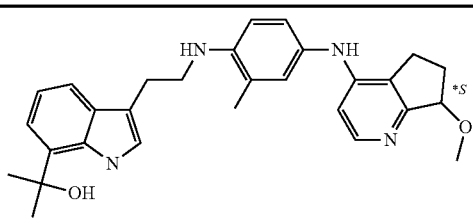

Co. No. 28; Ex. [B8, 9]

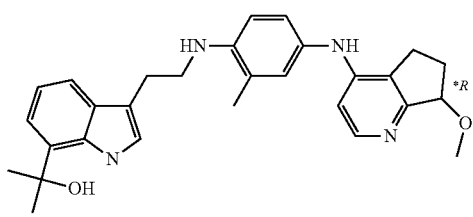

Co. No. 29; Ex. [B8, 9]

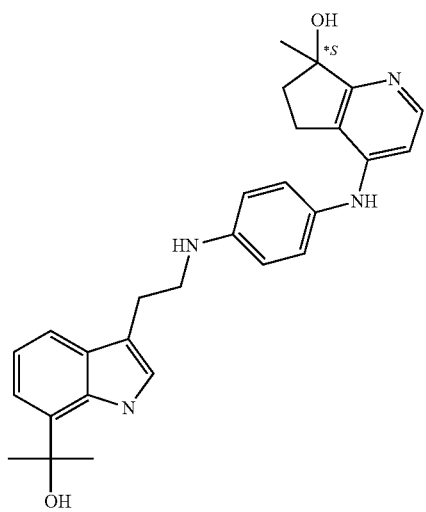

Co. No. 30; Ex. [B8, 9]

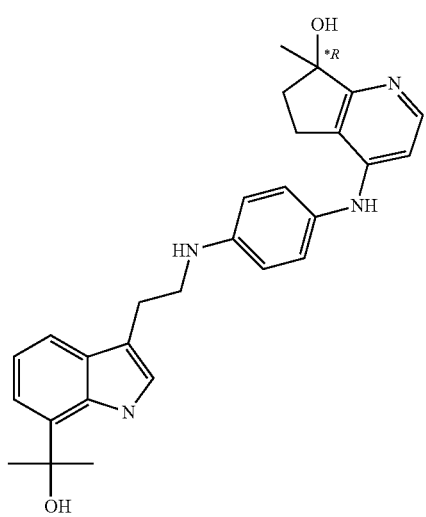

Co. No. 31; Ex. [B8, 9]

*means relative stereochemistry

Compound Characterization

Melting Points:

Values are either peak values or melt ranges, and were obtained with experimental uncertainties that are commonly associated with this analytical method.

Kofler

For compound 4 the melting point was obtained with a Kofler hot bench, consisting of a heated plate with linear temperature gradient, a sliding pointer and a temperature scale in degrees Celsius.

WRS-2A

For compound 11, 24, 25, 26, 27, 28, 29, 30, 31, the melting point was determined with a WRS-2A melting point apparatus that was purchased from Shanghai Precision and Scientific Instrument Co. Ltd. Melting point was measured with a linear heating up rate of 0.2-5.0° C./minute. The reported value is a melt range. The maximum temperature was 300° C.

DSC

For compound 1, the melting point was determined with DSC (differential scanning calorimetry). The melting point was measured with a temperature gradient of 10° C./minute. Maximum temperature was 350° C. Values are peak values.

LCMS

For LCMS-characterization of the compounds of the present invention, the following procedures were used.

General Procedure A

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3 kV and the source temperature was maintained at 100° C. on the LCT (Time of Flight Zspray™ mass spectrometer from Waters. Nitrogen was used as the nebulizer gas. Data acquisition was performed with a Waters-Micromass MassLynx-Openlynx data system.

General Procedure B

The LC measurement was performed using a HPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

General Procedure C

The HPLC measurement was performed using an Agilent 1100 module comprising a pump, a diode-array detector (DAD) (wavelength used 220 nm), a column heater and a column as specified in the respective methods below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50V. Drying gas temperature was maintained at 350° C. at a flow of 10 l/min.

Method 1

In addition to the general procedure A: Reversed phase HPLC was carried out on a Xterra-MS C18 column (5 μm, 4.6×150 mm) with a flow rate of 1.0 ml/min. Two mobile phases (mobile phase A: 100% 7 mM ammonium acetate; mobile phase B: 100% acetonitrile; were employed to run a gradient condition from 85% A, 15% B (hold for 3 minutes) to 20% A, 80% B in 5 minutes, hold at 20% A and 80% B for 6 minutes and reequilibrated with initial conditions for 3 minutes. An injection volume of 20 µl was used. Cone voltage was 20 V for positive ionization mode and 20 V for negative ionization mode. Mass spectra were acquired by scanning from 100 to 900 in 0.8 seconds using an interscan delay of 0.08 seconds.

Method 2

In addition to the general procedure B: Reversed phase HPLC was carried out on a Waters Acquity BEH (bridged ethylsiloxane/silica hybrid) C18 column (1.7 µm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 µl was used. Cone voltage was 20 V for positive and negative ionization mode. Mass spectra were acquired by scanning from 100 to 1000 in 0.2 seconds using an interscan delay of 0.1 seconds.

Method 3

In addition to general procedure C: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05% TFA) were used. First, 90% A and 10% B was hold for 0.8 minutes. Then a gradient was applied to 20% A and 80% B in 3.7 minutes and hold for 3 minutes. Typical injection volumes of 2 µl were used. Oven temperature was 50° C. (MS polarity: positive)

TABLE 2

LCMS data and melting points (Retention time: $R_t$ in minutes), $(MH)^+$ peak, LCMS procedure refers to the method used for LCMS.

| Comp. No. | $R_t$ | $(MH)^+$ | Procedure | melting points |
|---|---|---|---|---|
| 1 | 3.39 | 471 | 2 | 209° C. |
| 2 | 3.35 | 401 | 2 | |
| 4 | 3.19 | 441 | 2 | 121° C. |
| 5 | 2.97 | 417 | 2 | |
| 6 | 7.47 | 415 | 1 | |
| 7 | 3.94 | 439 | 2 | |
| 8 | 3.45 | 457 | 2 | |
| 9 | 8.51 | 471 | 1 | |
| 10 | 3.05 | 457 | 2 | |
| 11 | 3.01 | 473 | 3 | 221.0-222.5° C. |
| 12 | 3.07 | 443 | 2 | |
| 13 | 3.00 | 443 | 2 | |
| 14 | 3.49 | 425 | 2 | |
| 15 | 8.22 | 443 | 1 | |
| 16 | 3.34 | 457 | 2 | |
| 17 | 3.32 | 457 | 2 | |
| 18 | 8.68 | 457 | 1 | |
| 20 | 8.62 | 457 | 1 | |
| 21 | 8.2 | 443 | 1 | |
| 22 | 8.95 | 415 | 1 | |
| 23 | 2.93 | 443 | 3 | |
| 24 | | | | 110.5-111.6° C. |
| 25 | | | | 111.4-113.3° C. |
| 26 | | | | 122.3-124° C. |
| 27 | | | | 121.4-122.6° C. |
| 28 | | | | 98.3-100° C. |
| 29 | | | | 96.8-99° C. |

TABLE 2-continued

LCMS data and melting points (Retention time: $R_t$ in minutes), $(MH)^+$ peak, LCMS procedure refers to the method used for LCMS.

| Comp. No. | $R_t$ | $(MH)^+$ | Procedure | melting points |
|---|---|---|---|---|
| 30 | | | | 111.5-112.3° C. |
| 31 | | | | 112.7-113.6° C. |

Optical Rotation

The optical rotation was measured using a polarimeter. $[\alpha]_D^{20}$ indicates the optical rotation measured with light at the wavelength of the D-line of sodium (589 nm) at a temperature of 20° C. The cell pathlength is 1 dm. Behind the actual value the concentration and solvent of the solution which was used to measure the optical rotation are mentioned.

TABLE 3

Optical rotation

| Comp. Nr. | $[\alpha]_D^{20}$ | concentration | solvent |
|---|---|---|---|
| 18 | −37.4° | 0.516 w/v % | DMF |
| 20 | +36.87° | 0.575 w/v % | DMF |
| 21 | −39.68° | 0.378 w/v % | DMF |
| 24 | +5.03° | 10.30 mg/ml | MeOH |
| 25 | −3.44° | 10.70 mg/ml | MeOH |
| 26 | −13.74 | 8.59 mg/ml | Chloroform |
| 27 | +11.89 | 9.00 mg/ml | Chloroform |
| 30 | −5.25 | 4.00 mg/ml | MeOH |
| 31 | +7.99 | 4.00 mg/ml | MeOH |
| 28 | −4.90 | 10.00 mg/ml | MeOH |
| 29 | +5.69 | 9.89 mg/ml | MeOH |

C. Pharmacological Example:

The capacity of the present compounds to preserve p53 in A2780 cells was measured with the p53 enzyme linked immunosorbent assay. The p53 assay is a "sandwich" enzyme immunoassay employing two polyclonal antibodies. A polyclonal antibody, specific for the p53 protein, has been immobilized onto the surface of the plastic wells. Any p53 present in the sample to be assayed will bind to the capture antibody. The biotinylated detector polyclonal antibody also recognizes p53 protein, and will bind to any p53, which has been retained by the capture antibody. The detector antibody, in turn, is bond by horseradish peroxidase-conjugated streptavidin. The horseradish peroxidase catalyses the conversion of the chromogenic substrate o-phenylene diamine, the intensity of which is proportional to the amount of p53 protein bond to the plate. The colored reaction product is quantified using a spectrophotometer. Quantitation is achieved by the construction of a standard curve using known concentrations of purified recombinant HIS tagged p53 protein (see example C.1.).

C.1. p53 ELISA

A2780 cells (ATCC) were cultivated in RPMI 1640 supplemented with 10% fetal calf serum (FCS), 2 mM L-glutamine and gentamycin at 37° C. in a humidified incubator with 5% $CO_2$.

A2780 cells were seeded at 20.000 cells per well in a 96 well plate, cultured for 24 hours and treated with compound for 16 hours at 37° C. in a humidified incubator. After incubation, the cells were washed once with phosphate-buffered saline and 30 µl, per well, low salt RIPA buffer (20 mM tris, pH7.0, 0.5 mM EDTA, 1% Nonidet P40, 0.5% DOC, 0.05% SDS, 1 mM PMSF, 1 µg/ml aprotinin and 0.5 µ/ml leupeptin) was added. Plates were placed on ice for 30 minutes to complete the lysis. p53 protein was detected in de lysates by using the sandwich ELISA, described below.

High binding polystyrene EIA/RIA 96 well plates (Costar 9018) were coated with the capture antibody pAb1801 (Abcam ab28-100) at a concentration of 1 µg/ml in coating buffer (0.1 M NaHCO$_3$ pH8.2), 50 µl per well. The antibody was allowed to adhere overnight at 4° C. Coated plates were washed once with phosphate-buffered saline (PBS)/0.05% Tween 20 and 300 µl of blocking buffer (PBS, 1% bovine serum albumins (BSA)) was added, for an incubation period of 2 hours at room temperature. Dilutions of purified recombinant HIS tagged p53 protein, ranging from 3-200 ng/ml, were made in blocking buffer and used as standards.

Plates were washed twice with PBS/0.05% Tween 20 and blocking buffer or standards were added at 80 µl/well. To the standards, 20 µl of lysis buffer was added. The samples were added to the other wells at 20 µl lysate/well. After an overnight incubation at 4° C., plates were washed twice with PBS/0.05% Tween 20. Aliquots of 100 µl secondary polyclonal antibody p53(FL-393) (Tebubio, sc-6243) at a concentration of 1 µg/ml in blocking buffer were added to each well and allowed to adhere for 2 hours at room temperature. Plates were washed three times with PBS/0.05% Tween 20. Detection antibody anti-rabbit HRP (sc-2004, Tebubio) at 0.04 µg/ml in PBS/1% BSA was added and incubated for 1 hour at room temperature. Plates were washed three times with PBS/0.05% Tween 20 and 100 µl of substrate buffer was added (substrate buffer was prepared shortly before use by adding 1 tablet of 10 mg o-phenylene diamine (OPD) from Sigma and 125 µl 3% H$_2$O$_2$ to 25 ml OPD buffer: 35 mM citric acid, 66 mM Na$_2$HPO$_4$, pH5.6). After 5 to 10 minutes, colour reaction was stopped by adding 50 µl stop buffer (1 M H$_2$SO$_4$) per well. The absorbance at dual wavelengths of 490/655 nm was measured using a Biorad micro plate reader and the results were then analyzed.

For each experiment, controls (containing no drug) and a blank incubation (containing no cells or drugs) were run in parallel. The blank value was subtracted from all control and sample values. For each sample, the value of p53 (in absorbance units) was expressed as the percentage of the value for p53 present in the control. Percentage preservation higher than 140% was defined as significant. Herein the effects of test compounds are expressed as the lowest dose giving at least 140% of the value for p53 present in the control (LAD) (see Table 4).

In some of the experiments the assay was adapted for and used in 384-well culture plates.

TABLE 4

Results of the compounds that were tested in the above p53 ELISA protocol (A2780 cells)

| Comp. No. | p53-elisa LAD [microM] |
|---|---|
| 6 | 1.0 |
| 17 | 0.10 |
| 12 | 0.10 |
| 13 | 1.00 |
| 19 | 0.10 |
| 2 | 0.10 |
| 5 | 0.10 |
| 22 | 3.00 |
| 15 | 0.10 |
| 20 | 0.03 |
| 18 | 0.03 |
| 21 | 1.0 |
| 9 | 1.0 |
| 11 | 0.30 |
| 14 | 1.0 |
| 4 | 0.10 |
| 10 | 1.0 |
| 7 | 0.30 |
| 8 | 0.10 |
| 16 | 0.30 |
| 23 | 3.00 |
| 1 | 0.10 |
| 27 | 0.10 |
| 24 | 0.03 |
| 25 | 0.10 |
| 31 | 0.10 |
| 26 | 0.10 |
| 30 | 0.10 |
| 29 | 0.03 |
| 28 | 0.10 |

C.2 Proliferation Assay

The human A2780 ovarian cancer cells were a kind gift from Dr. T. C. Hamilton (Fox Chase Cancer Centre, Pennsylvania, U.S.A.). The cells were cultured in RPMI 1640 medium supplemented with 2 mM L-Glutamine, 50 µg/ml gentamicin and 10% fetal calf serum.

Reagents Used in the Alamar Blue Assay

Resazurin was purchased from Aldrich (Prod. No. 199303). Potassium ferrocyanide, potassium ferricyanide, KH$_2$PO$_4$ and K$_2$HPO$_4$ were purchased from Sigma (Prod. Nos. P9387, P8131, P5655 and P8281, respectively).

Potassium Phosphate Buffer 0.1 M (PPB) was made as follows: 2.72 gram KH$_2$PO$_4$ and 13.86 gram K$_2$HPO$_4$ were dissolved in 500 ml milli-Q H$_2$O, the pH was adjusted to pH 7.4 and the volume was brought to 1 liter with milli-Q H$_2$O; the buffer was filter sterilised and stored at room temperature. Resazurin stock solution (PPB-A) was prepared fresh by dissolving 45 mg resazurin in 15 ml PBS. 30 mM potassium ferricyanide (PPB-B) was prepared by dissolving 0.987 gram potassium ferricyanide in 100 ml PPB. 30 mM potassium ferrocyanide (PPB-C) was prepared by dissolving 1.266 gram potassium ferrocyanide in 100 ml PPB.

Mixture of PPB-A, PPB-B and PPB-C was prepared by mixing equal volumes of the respective solutions. Resazurin work solution (herein termed "Alamar Blue" solution) was prepared by diluting said mixture 20×(vol/vol) in PPB and filter sterilising; the Alamar Blue solution could be kept at 4° C. for a maximum of 2 weeks.

Procedure of the Alamar Blue Assay

For experiments in 384 wells plates the cells were seeded at a density of 5×10$^3$ cells/ml in Falcon 384-well culture plates (Life Technologies, Merelbeke, Belgium), black with clear bottom, in 45 µl culture medium. Cells were allowed to adhere to plastic for 24 hr. The tested compound was pre-diluted (1/50 in culture medium) and 5 µl pre-diluted compound was added to the wells. Following 4-day incubation, 10 µl of the Alamar Blue solution was added to each well and the cells were further incubated for 5 hrs (A2780) at 37° C. The fluorescence intensity was measured for each well with a Fluorescence plate reader (Fluorskan, Labsystems, 540 nm excitation and 590 nm emission)

The antiproliferative activity was calculated as percentage of remaining viable cells in treated versus control (untreated cells) conditions. Within an experiment, the result for each experimental condition is the mean of 3 replicate wells. When appropriate, the experiments were repeated to establish full concentration-response curves. When appropriate, IC$_{50}$-values (concentration of the drug, needed to reduce cell growth to 50% of the control) were computed using probit analysis for graded data (Finney, D. J., Probit Analyses, $2^{nd}$ Ed. Chapter 10, Graded Responses, Cambridge University Press, Cambridge 1962). Herein the effects of test compounds are expressed as $pIC_{50}$ (the negative log value of the $IC_{50}$-value (M)) (see Table 5A).

TABLE 5A

Results of the compounds that were tested in the above cell proliferation protocol (A2780 cells)

| Comp. No. | A2780 cell proliferation inhibition $pIC_{50}$ |
|---|---|
| 6 | 6.67 |
| 17 | 7.40 |
| 12 | 7.20 |
| 13 | 6.90 |
| 19 | 7.34 |
| 2 | 7.38 |
| 5 | 7.28 |
| 22 | 6.26 |
| 15 | 7.27 |
| 20 | 7.29 |
| 18 | 7.47 |
| 21 | 6.85 |
| 9 | 6.85 |
| 11 | 6.55 |
| 14 | 6.43 |
| 4 | 6.74 |
| 10 | 6.70 |
| 7 | 6.96 |
| 8 | 7.06 |
| 16 | 6.87 |
| 23 | 6.52 |
| 1 | 6.94 |
| 27 | 6.85 |
| 24 | 7.18 |
| 31 | 6.84 |
| 26 | 7.11 |
| 30 | 7.04 |
| 29 | 7.14 |
| 28 | 6.89 |

Compounds were also tested according to the above protocol but using other cell lines: colorectal cancer cell line HCT116, non-small cell lung cancer cell line H1299, human prostate cancer cell line DU145. Results are reported in Table 5B.

TABLE 5B

| Comp. No. | HCT116 cell proliferation inhibition $pIC_{50}$ | H1299 cell proliferation inhibition $pIC_{50}$ | DU145 cell proliferation inhibition $pIC_{50}$ |
|---|---|---|---|
| 6 | 5.39 | 5.03 | |
| 17 | 7.05 | 6.18 | 6.17 |
| 12 | 6.06 | 5.2 | |
| 13 | 5.61 | <5 | |
| 19 | | 5.46 | 5.74 |
| 2 | | 5.94 | 6.16 |
| 5 | 6.46 | 5.23 | 5.56 |
| 22 | | 5.09 | 5.07 |
| 15 | 6.69 | 5.82 | |
| 20 | | 5.72 | 5.73 |
| 18 | 7.27 | 6.38 | 6.40 |
| 21 | 6.83 | 6.12 | 5.22 |
| 9 | 6.02 | 5.17 | 5.26 |
| 11 | 6.67 | 5.81 | 6.21 |
| 14 | <5 | 5.40 | 5.14 |
| 4 | 6.00 | 5.43 | 5.29 |
| 10 | 6.47 | 5.68 | 5.65 |
| 7 | 7.00 | 6.39 | 6.60 |
| 8 | 7.06 | | |
| 16 | 6.68 | 6.73 | 5.98 |
| 23 | 5.53 | 5.61 | 5 |
| 1 | 6.82 | 6.06 | 5.92 |
| 27 | 7.08 | 5.99 | 6.00 |
| 24 | 7.42 | 6.63 | 6.53 |
| 31 | 6.94 | 5.84 | 6.04 |
| 26 | 7.26 | 6.27 | 6.18 |
| 30 | 7.19 | 6.02 | 6.14 |
| 29 | 7.37 | 6.67 | 6.58 |
| 28 | 7.11 | 6.73 | 6.52 |

C.3. P450 Assay

The CYP P450 (*E. coli* expressed) proteins (3A4, 2D6, 2C9, 1A2 & 2C19) convert their specific substrates into a fluorescent molecule[1,2]. The fluorescent molecule is measured using a fluorescent plate reader. Compounds inhibiting the enzymatic reaction will result in a decrease of fluorescent signal.

Conversions Mediated by the Respective cDNA Expressed Cytochrome P450 Isoenzymes.

| Substrate | enzyme | fluorescent molecule |
|---|---|---|
| CEC | CYP1A2 → | CHC |
| MFC | CYP2C9 → | 7-HFC |
| CEC | CYP2C19 → | CHC |
| AMMC | CYP2D6 → | AHMC |
| BFC | CYP3A4 → | 7-HFC |
| DBF | CYP3A4 → | Fluorescein |
| 7-BQ | CYP3A4 → | Quinolinol |

Abbreviations:
CEC: 7-ethoxy-3-cyanocoumarin;
CHC: 3-cyano-7-hydroxycoumarin,
MFC: 7-Methoxy-4-trifluoromethyl coumarin;
7-HFC: 7-Hydroxy-trifluoromethyl coumarin,
CEC: 7-ethoxy-3-cyanocoumarin;
CHC: 3-cyano-7-hydroxycoumarin,
AMMC: 3-[2-(N,N-diethyl-N-methylamino)ethyl]-7-methoxy-4-methylcoumarin;
AHMC: 3-[2-(N,N-diethylamino)ethyl]-7-hydroxy-4-methylcoumarin hydrochloride,
BFC: 7-Benzyloxy-trifluoromethyl coumarin;
DBF: Dibenzylfluorescein,
7-BQ: Benzyloxyquinoline.

Cofactor Mix: (for all CYP Enzymes Except for CYP 2D6)

| | working solution | | final concentration | |
|---|---|---|---|---|
| G-6-P | 8.25 | mM | 25.10 mg | 3.3 mM |
| G-6-P-DH | 1 | U/ml | 14.29 μl | 0.4 U/ml |
| 0.5M MgCl$_2$•6H$_2$O | 8.25 | mM | 165.0 μl | 3.3 mM |
| NADP | 3.25 | mM | 25.59 mg | 1.3 mM |
| dissolved in a 0.1M Na—K-phosphate buffer | | | 10 ml | |

Abbreviations: G-6-P: glucose-6-phosphate; G-6-P-DH: glucose-6-phosphate-dehydrogenase.

Cofactor Mix: (for CYP2D6)

|  | working solution |  | final concentration |
|---|---|---|---|
| G-6-P | 1.025 mM | 3.12 mg | 0.41 mM |
| G-6-P-DH | 1 U/ml | 14.29 µl | 0.4 U/ml |
| 0.5M MgCl$_2$•6H$_2$O | 1.025 mM | 20.5 µl | 0.41 mM |
| NADP | 20.5 µM | 0.161 mg | 8.2 µM |
| dissolve in a 0.1M Na—K-phosphate buffer |  | 10 ml |  |

CYP P450 Enzyme Solutions:

| CYP1A2: | (CEC) | final concentration 5 pmol P450/ml |
|---|---|---|
| CYP2C9: | (MFC) | final concentration 60 pmol P450/ml |
| CYP2C19: | (CEC) | final concentration 2.5 pmol P450/ml |
| CYP2D6: | (AMMC) | final concentration 40 pmol P450/ml |
| CYP3A4: | (BFC) | final concentration 83 pmol P450/ml |
|  | (DBF) | final concentration 5 pmol P450/ml |
|  | (7-BQ) | final concentration 20 pmol P450/ml |

All these CYP enzymes were dissolved in 0.01 M Na—K-phosphate buffer+1.15% KCl, and kept on ice until use. The CYP P450 enzymes were stored at −80° C.

Compound and Reference Inhibitor Dilution:

Compounds and reference inhibitors were delivered to the department as a 5 mM solution in DMSO. A working solution of $5.10^{-4}$M was made by serial dilution using acetonitrile. The final compound concentration was $10^{-5}$M for the primary screen, and the final solvent concentration 2%. After a primary screen at a concentration of $10^{-5}$M, the IC$_{50}$ values of selected potent inhibitors were tested at a concentration range of $3.10^{-9}$-$10^{-5}$ M. In the primary screen, all compounds were tested in triplicate.

Reference inhibitors were tested at a concentration range of $10^{-9}$-$10^{-4}$ M.

Reference Inhibitors:

| Furafylline: | (Ultra Fine Chemicals) | for CYP1A2 |
|---|---|---|
| Sulfaphenazole: | in house | for CYP2C9 |
| Tranylcypromine: | in house | for CYP2C19 |
| Quinidine: | in house | for CYP2D6 |
| Ketoconazole: | in house | for CYP3A4 |

Substrate Solutions:

| CEC | (CYP1A2 substrate) | 6.25 µl 20 mM CEC solution/5 ml total volume | 5 µM |
|---|---|---|---|
| MFC | (CYP2C9 substrate) | 200 µl 25 mM MFC solution/5 ml total volume | 200 µM |
| CEC | (CYP2C19 substrate) | 31.25 µl 20 mM CEC solution/5 ml total volume | 25 µM |
| AMMC | (CYP2D6 substrate) | 150 µl 0.5 mM AMMC solution/5 ml total volume | 3 µM |
| BFC | (CYP3A4 substrate) | 750 µl 5 mM BFC solution/5 ml total volume | 150 µM |
| DBF | (CYP3A4 substrate) | 12.5 µl 2 mM DBF solution/5 ml total volume | 1 µM |
| 7-BQ | (CYP3A4 substrate) | 60 µl 25 mM 7-BQ solution/5 ml total volume | 60 µM |

The substrate stock solutions were dissolved in acetonitrile, and stored at −20° C. The final working solution was dissolved in 0.1 M Na—K-phosphate buffer pH 7.4, and this solution was always prepared fresh before starting the assay.

Data Analysis

Plate preparation, data linking, data analysis, results validation & approval and data upload were semi-automatically performed by the Lexis-Laplace software (Laplace-DLM-RVAM)

The formula used in the calculations are:

% activity=(100/(avg positive control−avg negative control))×(avg sample−avg negative control).

% inhibition=100−% activity

When calculated, the IC$_{50}$ value was automatically generated by graphical extrapolation in RVAM, based on the intersection with the 50% of control axis.

Method

The assay was performed in a black 96 well Costar plate. Per well the assay comprises: 40 µl CYP P450 enzyme solution (in the negative control samples 40 µl of 0.1M Na—K-phosphate buffer pH 7.4 without enzyme was added); 40 µl cofactor mix; 2 µl compound or reference inhibitor for negative control samples or solvent for positive control samples. After 5 min preincubation at 37° C. in a shaking incubator, 20 µl substrate solution was added. The plates were incubated at 37° C. for 10 min (CYP3A4/DBF), 15 min (CYP1A2), 30 min (CYP2C9, CYP3A4/BFC and CYP3A4/7-BQ & CYP2C19) and 45 min (CYP2D6). The reaction was stopped by addition of 200 µl acetonitrile. For CYP3A4/DBF the reaction was stopped by addition of 200 µl 2M NaOH. For CYP3A4/7-BQ the reaction was stopped by addition of 40 µl Tris/acetonitrile (1:5) (V:V, followed by a 10 minute centrifugation at 2000 rpm. The fluorescent signal was detected by a fluorescent Victor2 (Wallac) or Fluoroskan (Labsystems) reader. The excitation and emission wavelength for the different enzymes and their specific substrate are mentioned in the Table 6.

TABLE 6

| Excitation and emission wavelengths | | | |
|---|---|---|---|
| Enzyme | Substrate | Excitation wavelength | Emission wavelength |
| CYP1A2 | CEC | 410 nm | 460 nm |
| CYP3A4 | BFC | 405 nm | 535 nm |
| CYP3A4 | DBF | 485 nm | 538 nm |
| CYP3A4 | 7-BQ | 405 nm | 535 nm |
| CYP2C9 | MFC | 405 nm | 535 nm |
| CYP2C19 | CEC | 410 nm | 460 nm |
| CYP2D6 | AMMC | 390 nm | 460 nm |

REFERENCES

[1] Microtiter Plate Assays for Inhibition of Human, Drug-Metabolizing Cytochromes P450 Charles L. Crespi, Vaughn P. Miller, Bruce W. Penman (Gentest) Analytical Biochemistry 248, 188-190 (1997) Article n° AB972145

[2] Novel High Throughput fluorescent P450 assays V. P. Miller, J. Ackermann, D. M. Stresser, C. L. Crespi Gentest Internet site.

Table 7 gives data for the compounds of the present invention (compounds no 18, 20, 9, 14 and 4) tested in the seven tests when compared with compounds of the prior art. As described above five P450 enzymes were tested, one of them on three different substrates (thus seven tests in total). In the table 7 is indicated on how many P450 tests a compound showed an inhibitory activity with an IC$_{50}$<1.00E-06.

TABLE 7

Comparative data on CYP inhibition

| compound | P450 effects IC$_{50}$ |
|---|---|
| 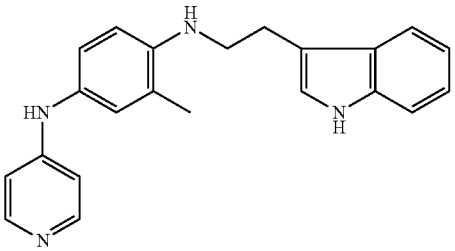<br>Compound No. 47 or EP1809622 | 7 times < 1.00E−06 |
| 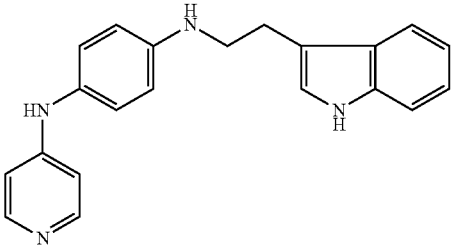<br>Compound No. 36 of EP1809622 | 3 times < 1.00E−06 |
| 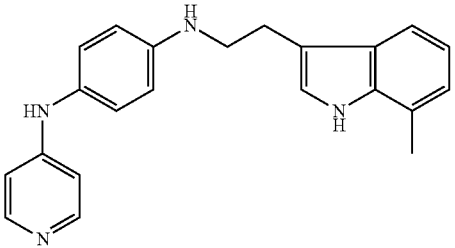<br>Compound of No. 197 of EP1809622 | 7 times < 1.00E−06 |
| 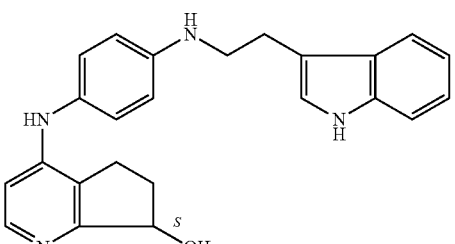<br>Compound No. 195 of EP1809622 | 0 times < 1.00E−06 |

TABLE 7-continued

Comparative data on CYP inhibition

| compound | P450 effects IC$_{50}$ |
|---|---|
| 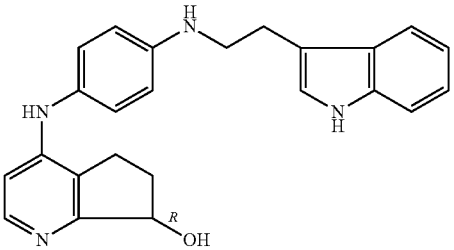<br>Compound No. 229 of EP1809622 | 0 times < 1.00E−06 |
| 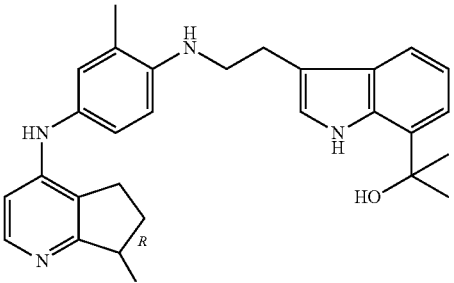<br>Compound No 20 | 0 times < 1.00E−06 |
| 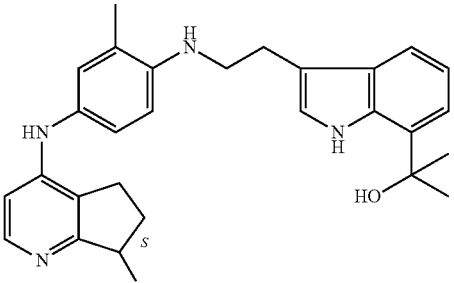<br>Compound No 18 | 0 times < 1.00E−06 |
| 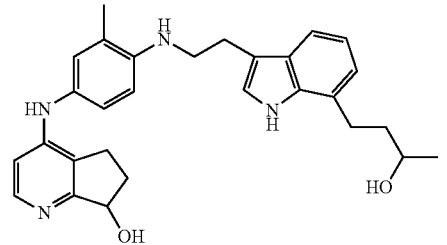<br>Compound No 9 | 0 times < 1.00E−06 |

TABLE 7-continued

Comparative data on CYP inhibition

| compound | P450 effects IC$_{50}$ |
|---|---|
| 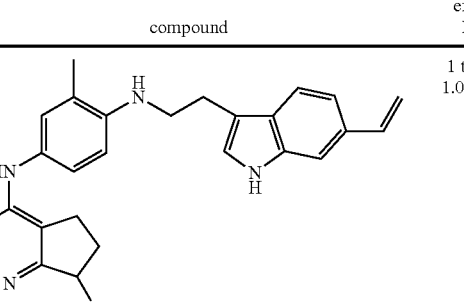  Compound No 14 | 1 time < 1.00E−06 |
| Compound No 4 | 0 times < 1.00E−06 |

C.4. Ro-4-1284 Antagonism in Mice[3,4,5]

The test is a modification of a procedure described by Colpaert et al. (1975).[3] Male NMRI mice (22±3 g) were housed in macrolon observation cages (L×W×H: 11×12×17 cm; n=3 per cage). At the start of the experiments immediately before test compound administration, the initial body temperature of the mice was measured with a precision of 0.1° C. by inserting the thermo-sensitive probe (1.0 mm diameter) of an electric thermometer (Comark) to a constant depth of 3 cm into the esophagus until a stable reading was obtained. The right eye pupil diameter was measured with a graduated microscope and expressed in 1/24 mm units. Fifteen min after test compound administration, the mice were challenged with Ro-4-1284 (10 mg/kg, s.c.). Ro-4-1284 is a reserpine-like vesicular monoamine transport (VMAT-2) inhibitor, which rapidly depletes secretory vesicles.[3,4] Fifteen, 30 and 60 min after challenge, the mice were scored for palpebral opening (0, 1, 2, 3, 4, 5) and locomotor activity (−1, 0, 1, 2, 3). At the 60-min interval, immediately after the scoring of overt behavior, the right eye pupil diameter and the esophageal temperature were measured again. Abnormal phenomena such as intensive sniffing, chewing, rearing, hyperemia, piloerection, salivation, tremors, convulsions and death were noted (the latter phenomena were also noted when occurring before Ro-4-1284 administration). Criteria for drug-induced effects: reversal of ptosis: palpebral opening score >1 at 15, 30 or 60 min (2.7, 0.5 and 0% false positive controls, respectively; n>350); induction of prostration: score −1 for locomotion at 15, 30 or 60 min (never observed in controls); reversal of hypomotility: score >0 for locomotion at 15, 30 and 60 min (2.2, 0.8 and 0% false positive controls, respectively); reversal of miosis: pupil diameter >5 units at 60 min (0.8% false positives); potentiation of hypothermia: temperature decrease (over the 1-h time interval)>9.0° C. (1.4% false positives); reversal of hypothermia: temperature decrease <3.0° C. (1.8% false positives).

According to the standard procedure, R0-4-1284 is injected 15 min following subcutaneous or oral administration and observations start 15 min later. Doses are initially given to 3 animals. When at least 2 out of the 3 animals show activity for at least one of the observations, the compound is considered active. In other cases, the compound is considered inactive at the particular time-route-dose regimen and classified as finished.

Compound No. 20, 18, 1, 27, 24, 25, 31, 30, 7, 29, 28, 26 and 17 were each tested on 3 animals at a concentration of 80 mg/kg following oral administration and they did not show activity on reversal of miosis, reversal of ptosis, reversal of hypomotility. Compound 4 was only tested at 40 mg/kg and did not show activity on reversal of miosis, reversal of ptosis, reversal of hypomotility.

Compounds of EP 1809622 were also tested in the same test and the results are shown in the below Table 8.

TABLE 8

Comparative data

| compound | drug induced neurological side effects |
|---|---|
| 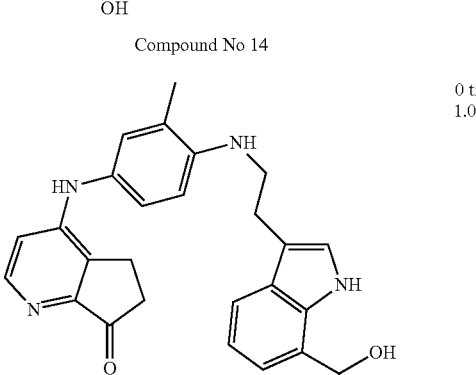  Compound No. 47 of EP1809622 | yes |
| Compound No. 36 of EP1809622 | yes |
| Compound No. 187 of EP1809622 | yes |

TABLE 8-continued

Comparative data

| compound | drug induced neurological side effects |
|---|---|
| 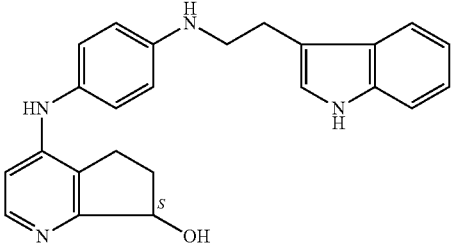<br>Compound No. 195<br>of EP1809622 | yes |
| 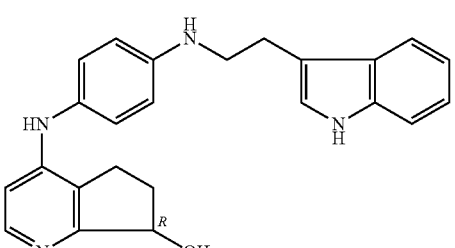<br>Compound No. 229<br>of EP1809622 | yes |

REFERENCES

[3] Colpaert, F. C., Lenaerts, F. M., Niemegeers, C. J. E., Janssen, P. A. J.: "A critical study on Ro-4-1284 antagonism in mice.", Arch. Int. Pharmacodyn. 215 40-90 (1975).

[4] Colzi, A., D'Agostini, R., Cesura, A. M., Borroni, E., Da Prada, M.: "Monoamine oxidase-A inhibitors and dopamine metabolism in rat caudatus: evidence that an increased cytosolic level of dopamine displaces reversible monoamine oxidase-A inhibitors in vivo.", J. Pharmacol. Exp. Ther. 265 103-111 (1993).

[5] Filinger, E. J.: "Effect of a reserpine-like agent on the release and metabolism of [$^3$H]NA in cell bodies and terminals.", Gen. Pharmacol. 25 1039-1043 (1994).

C.5 Patch-clamp Test-Inhibition of HERG-mediated K+ Current in HEK293 Cells

Experiments were performed using HEK293 cells stably expressing the HERG potassium channel. Cells were grown at 37° C. and 5% $CO_2$ in culture flasks in MEM Medium supplemented with 10% heat-inactivated fetal bovine serum, 1% L-Glutamine-Penicillin-Streptomycin-solution, 1% non-essential amino acids (100×), 1% sodium pyruvate (100 mM) and 0.8% Geneticin (50 mg/ml). Before use the cells were subcultured in MEM medium in the absence of 5 ml L-Glutamine-Penicillin-Streptomycin. For use in the automated patch-clamp system PatchXpress 7000A (Axon Instruments) cells were harvested to obtain cell suspension of single cells. Extracellular solution contained (mM): 150 NaCl, 4 KCl, 1 $MgCl_2$, 1.8 $CaCl_2$, 10 HEPES, 5 Glucose (pH 7.4 with NaOH). Pipette solution contained (mM): 120 KCl, 10 HEPES, 5 EGTA, 4 ATP-Mg2, 2 $MgCl_2$, 0.5 $CaCl_2$ (pH 7.2 with KOH).

Patch-clamp experiments were performed in the voltage-clamp mode and whole-cell currents were recorded with an automated patch-clamp assay utilizing the PatchXpress 7000A system (Axon Instruments). Current signals were amplified and digitized by a Multiclamp amplifier, stored and analyzed by using the PatchXpress, DataXpress software and Igor 5.0 (Wavemetrics).

The holding potential was −80 mV. The HERG current (K+-selective outward current) was determined as the maximal tail current at −40 mV after a 2 second depolarization to +60 mV. Pulse cycling rate was 15 s. Before each test pulse a short pulse (0.5 s) from the holding potential to −60 mV was given to determine (linear) leak current. After establishing whole-cell configuration and a stability period, the vehicle was applied for 5 minutes followed by the test substance by increasing concentrations of 10-7 M, 3×10-7 M and 3×10-6 M. Each concentration of the test substance was applied twice. The effect of each concentration was determined after 5 min as an average current of 3 sequential voltage pulses. To determine the extent of block the residual current was compared with vehicle pre-treatment. Data (Table 9) are presented as mean values (±standard error of the mean (SEM) if available) of percentage inhibition compared to control (control is 100%) (n=number of experiments).

TABLE 9

Inhibition of HERG-mediated K+ current in HEK293 cells

| Compound | $1.10^{-7}$M | $3.10^{-7}$M | $3.10^{-6}$M |
|---|---|---|---|
| 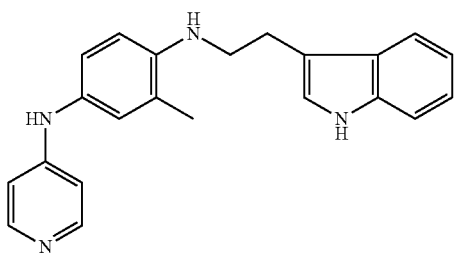<br>Compound No. 47<br>of EP1809622<br>(n = 3) | 76 ± 1.6 | 58 ± 2.7 | 13 ± 3.1 |

TABLE 9-continued

Inhibition of HERG-mediated K+ current in HEK293 cells

| Compound | $1 \cdot 10^{-7}$ M | $3 \cdot 10^{-7}$ M | $3 \cdot 10^{-6}$ M |
|---|---|---|---|
| Compound No. 36 of EP1809622 (n = 3) | 68 ± 3.5 | 41 ± 2.9 | 5 ± 0.33 |
| Compound No. 187 of EP1809622 (n = 3) | 68 ± 3.2 | 36 ± 6.1 | 5 ± 1 |
| Compound No. 195 of EP1809622 (n = 3) | 80 ± 3.7 | 65 ± 2 | 19 ± 0.4 |
| Compound No. 229 of EP1809622 (n = 3) | 81 ± 4.8 | 63 ± 5.5 | 18 ± 1.1 |

TABLE 9-continued
Inhibition of HERG-mediated K⁺ current in HEK293 cells
| Compound | $1.10^{-7}$M | $3.10^{-7}$M | $3.10^{-6}$M |
|---|---|---|---|
| 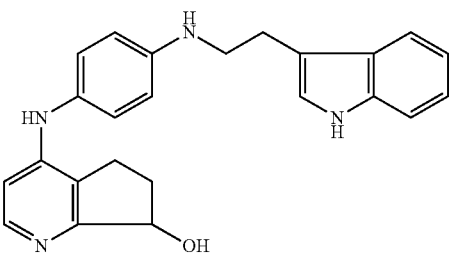<br>Compound No 110<br>of EP1809622<br>(N = 4) | 86 ± 4.6 | 66 ± 5.2 | 22 ± 4.6 |
| 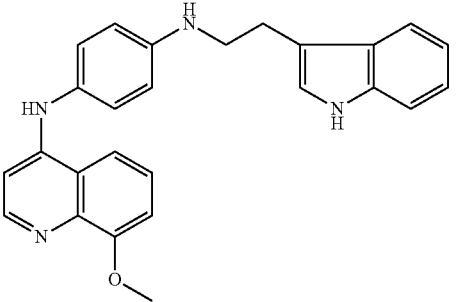<br>Compound No 21<br>of EP1809622<br>(n = 3) | 35 ± 8.6 | 8 ± 3.6 | 0 ± 0 |
| 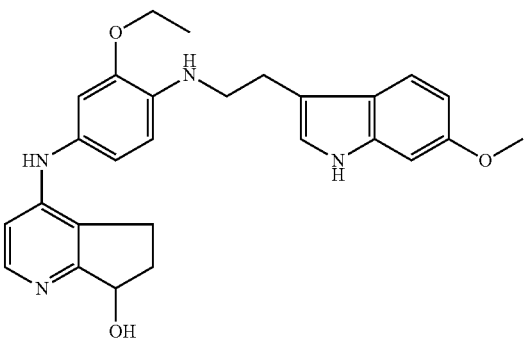<br>Compound 112 of EP1809622 (n = 3) | 74 ± 3.2 | 46 ± 7.3 | 6 ± 3.1 |
| 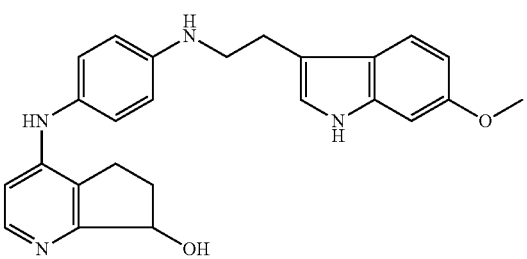<br>Compound 196 of EP1809622 (n = 3) | 87 ± 0.9 | 76 ± 1.6 | 38 ± 3.1 |

TABLE 9-continued

Inhibition of HERG-mediated K⁺ current in HEK293 cells

| Compound | $1.10^{-7}$M | $3.10^{-7}$M | $3.10^{-6}$M |
|---|---|---|---|
| Compound No 2 (n = 3) | 89 ± 3.9 | 75 ± 0.8 | 18 ± 4.6 |
| Compound No. 20 (n = 3) | 88 ± 5.1 | 76 ± 1.8 | 26 ± 7.1 |
| Compound No 18 (n = 3) | 90 ± 1.8 | 82 ± 3.8 | 41 ± 4.3 |
| Compound No. 1 (n = 4) | 86 ± 2.5 | 82 ± 1.1 | 69 ± 5.1 |

TABLE 9-continued
Inhibition of HERG-mediated K⁺ current in HEK293 cells
| Compound | $1.10^{-7}$M | $3.10^{-7}$M | $3.10^{-6}$M |
|---|---|---|---|
| 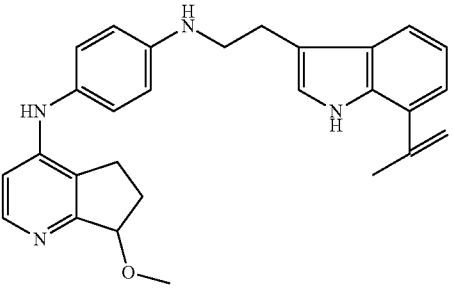<br>Compound No. 7 (n = 3) | 86 ± 2.9 | 53 ± 6.8 | 2 ± 0.3 |
| 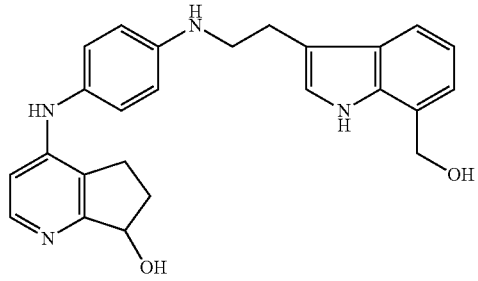<br>No. 6 (n = 4) | 89 ± 2.9 | 87 ± 4.8 | 69 ± 3.4 |
| 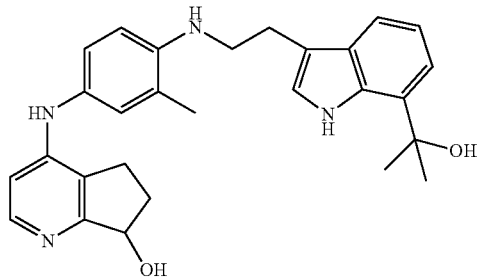<br>No. 17 (n = 3) | 84 ± 3.9 | 70 ± 4.7 | 21 ± 3.3 |
| 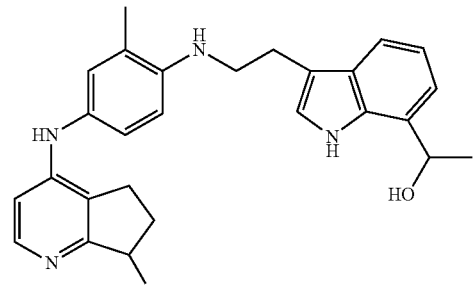<br>No. 12 (n = 6) | 87 ± 0.9 | 78 ± 2.8 | 58 ± 2.9 |

TABLE 9-continued

Inhibition of HERG-mediated K⁺ current in HEK293 cells

| Compound | $1 \cdot 10^{-7}$M | $3 \cdot 10^{-7}$M | $3 \cdot 10^{-6}$M |
|---|---|---|---|
| No. 13 (n = 3) | 91 ± 2.8 | 85 ± 4.2 | 75 ± 1.8 |
| No. 19 (n = 3) | 89 ± 2.4 | 72 ± 3.2 | 26 ± 4.7 |
| No. 5 (n = 3) | 88 ± 1.9 | 74 ± 6.1 | 33 ± 10.5 |
| No. 22 (n = 3) | 76 ± 5.2 | 49 ± 7.8 | 9 ± 2.3 |

TABLE 9-continued

Inhibition of HERG-mediated K⁺ current in HEK293 cells

| Compound | $1.10^{-7}$M | $3.10^{-7}$M | $3.10^{-6}$M |
|---|---|---|---|
| No. 15 (n = 3) | 93 ± 1.2 | 88 ± 0.8 | 66 ± 4.4 |
| No. 21 (n = 3) | 91 ± 0.9 | 86 ± 1.8 | 65 ± 1.2 |
| No. 9 (n = 3) | 87 ± 2.1 | 72 ± 3.4 | 47 ± 3.2 |
| No. 11 (n = 3) | 90 ± 8.7 | 80 ± 7.2 | 43 ± 3.3 |

TABLE 9-continued
Inhibition of HERG-mediated K⁺ current in HEK293 cells
| Compound | $1.10^{-7}$M | $3.10^{-7}$M | $3.10^{-6}$M |
|---|---|---|---|
| 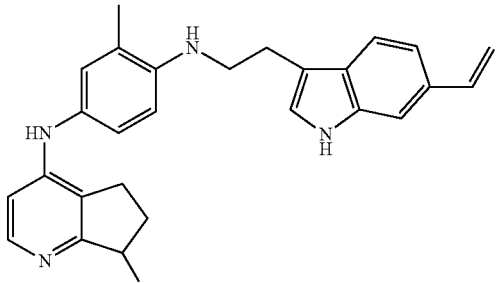 No. 14 (n = 4) | 84 ± 2.1 | 57 ± 5.4 | 10 ± 3.8 |
| 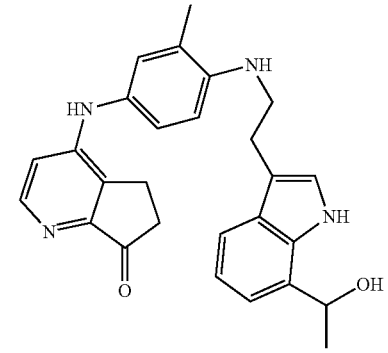 No. 4 (n = 3) | 89 ± 4.2 | 85 ± 1.7 | 66 ± 3.3 |
| 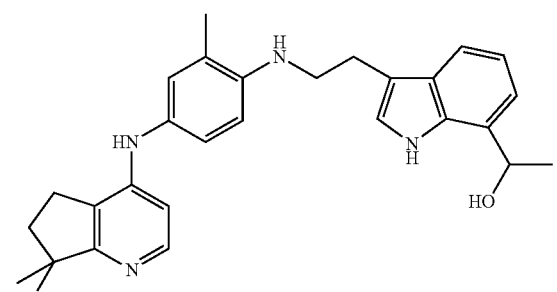 No. 10 (n = 3) | 82 ± 2.1 | 72 ± 2.6 | 62 ± 1.8 |
| 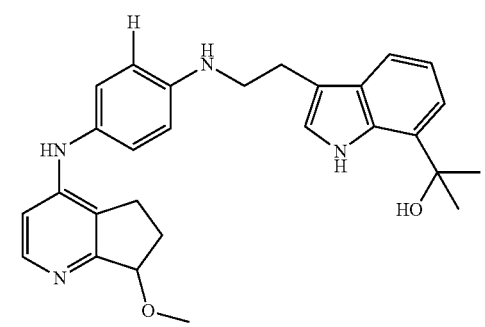 No. 8 (n = 3) | 93 ± 7.3 | 83 ± 6.4 | 25 ± 5.4 |

TABLE 9-continued

Inhibition of HERG-mediated K⁺ current in HEK293 cells

| Compound | $1.10^{-7}$M | $3.10^{-7}$M | $3.10^{-6}$M |
|---|---|---|---|
| No. 16 (n = 3) | 89 ± 6.0 | 74 ± 7.9 | 34 ± 4.4 |
| No. 23 (n = 3) | 92 ± 1.0 | 87 ± 2.0 | 72 ± 0.4 |
| No. 27 (n = 3) | 90 ± 1.8 | 75 ± 3.3 | 53 ± 8.1 |
| No. 24 (n = 3) | 88 ± 3.2 | 77 ± 4.2 | 29 ± 2.9 |

TABLE 9-continued
| Inhibition of HERG-mediated K⁺ current in HEK293 cells | | | |
|---|---|---|---|
| Compound | $1.10^{-7}$M | $3.10^{-7}$M | $3.10^{-6}$M |
| 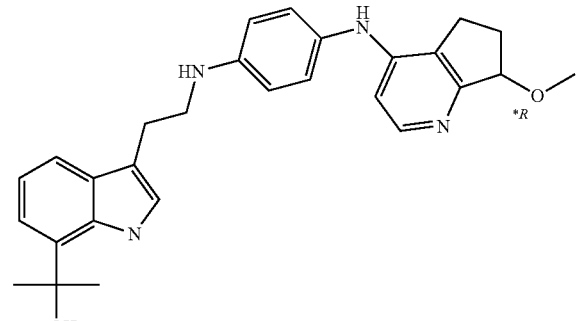 No. 25 (n = 3) | 82 ± 1.7 | 65 ± 2.8 | 27 ± 2.7 |
| 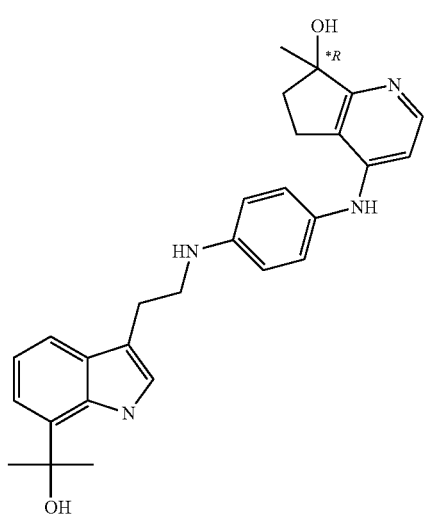 No. 31 (n = 3) | 91 ± 0.9 | 82 ± 2.3 | 55 ± 3.8 |
| 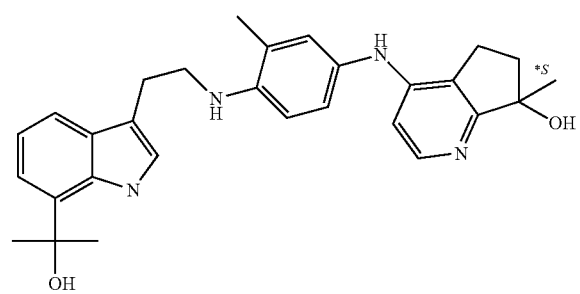 No. 26 (n = 3) | 87 ± 1.7 | 78 ± 1.8 | 51 ± 5.9 |

TABLE 9-continued

| Inhibition of HERG-mediated K⁺ current in HEK293 cells | | | |
|---|---|---|---|
| Compound | $1.10^{-7}$M | $3.10^{-7}$M | $3.10^{-6}$M |
| No. 30 (n = 3) | 98 ± 1.6 | 93 ± 6.3 | 80 ± 7.2 |
| No. 29 (n = 3) | 89 ± 2.3 | 82 ± 3.9 | 39 ± 0.8 |
| No. 28 (n = 4) | 84 ± 4.4 | 79 ± 8.8 | 60 ± 6.4 |

Surprisingly, the present compounds show excellent in-vitro activity, which is combined with low affinity for P450 enzymes and no in vivo drug induced neurological effects and low cardiovascular effects.

C.6. In vivo Anti Tumour Effects

In vivo antitumoral activity can be tested as follows:

NCI Standard Reference:

Bissery, M-C., and Chabot, G. G. History and new development of screening and evaluation methods of anticancer drugs used in vivo and in vitro. Bull. Cancer. 1991, 78: 587-602.

Animal Model:

Immuno-deficient (athymic) male NMRI Nude (Nu/Nu) mice (20-25 g obtained from Janvier, France) were used for these studies. Initial weight was approximately 23 to 34 g. All animals were maintained under SPF "full barrier" conditions with free access to food and water. Mice were group housed under a 12-h light:dark cycle (lights on at 06:00 h) at a temperature of 19 to 22° C. and 35 to 40% humidity in Techniplast type-3 IVC cages. Mice were fed a standard Laboratory chow. All experiments were carried out in accordance with the European Communities Council Directives (86/609/EEC) and had to be approved by the local ethical committee. For an established tumor xenograft model (tumor volume ~200 mm³), mice were randomized according to tumor volumes, with 5 mice per treatment group.

Test System:

The human U87 glioma tumor cell line was derived from a 44 year old female Caucasian patient. Cells were cultured at 37° C. in a humidified atmosphere (5% $CO_2$, 95% air), in DMEM medium supplemented with 2 mM L-glutamine, 2.0 mM sodium pyruvate, 25 units/ml penicillin/25 µg/ml streptomycin and 10% fetal bovine serum. Cells were maintained as cell monolayer cultures, being passaged twice weekly at $3\times10^6$ cells per T175 flask using the following procedure. Briefly cells were washed with PBS (without $Mg^{2+}$, $Ca^{2+}$), before addition of trypsin-EDTA to the culture flasks. After detachment of cells the trypsin-EDTA was inactivated by addition of complete medium. Cell suspension was then transferred to 50 ml Falcon tube and centrifuged for 3 min at 1200 rpm. Medium was aspirated, with the cells being re-suspended in an appropriate volume of complete medium. The cells were counted in a haemocytometer and their viability was assessed by 0.25% trypan blue exclusion. An appropriate volume of cell suspension was then added to either a new T175 culture flask(s) or roller bottle containing fresh medium. For large scale-up growth of U87 tumor cells, an appropriate number of roller bottles were seeded with 0.5 to $1\times10^7$ cells 1 week prior to inoculation of mice. The medium was changed twice during this period, with the last change being the day prior to cell injection. Cells were collected as described above, with the exception that after centrifugation, the cells were re-suspended in cold (4° C.) serum-free medium. Mice were injected in the inguinal region with $1\times10^7$ cells total in a 200 µl volume.

Study Design:

Human U87 glioma cells were injected directly into the inguinal region of the male NMRI Nude mice ($1\times10^7$ cells/200 µl/animal) on day 0 (D0). On day 7-10 (can vary due to tumor take/growth between cell batches) when tumor volume had reached an approximate average of 200 mm³, mice were randomized according to tumor volume, with 5 mice per treatment group. Mice were then treated once daily (QD) with either vehicle (10% HP-β-CD) or vehicle containing test compound (20 mg/kg) by gavage (p.o.) administered in a volume of 10 ml/kg body weight for 5 days. Specific tumor measurements were taken on day 6 (24 hours post $5^{th}$ dose) and then again on day 10. Tumor re-growth (after dosing has stopped) was monitored so that the time-to-reach a volume of 2000 mm³ (TTR2000) can be recorded. This gives extra information on the duration of drug action on the tumor growth. In general, tumor size and body weights were measured twice weekly, with mice monitored daily for clinical signs of toxicity for the duration of the treatment. Clinical signs of toxicity included (but not limited to), persistent anorexia or dehydration, posture, moribund, lethargy, hypothermia and/or laboured respiration (according to the UKCCCR guidelines for welfare of animals in experimental neoplasia (The UKCCCR (UK Coordinating Committee on Cancer Research) guidelines for the welfare of animals in experimental neoplasia (July 1997); and Workman, P. et al. UKCCCR guideline. *Br. J. Cancer.* 1998, 77: 1-10).

Data Analysis:

For each individual animal, body weight and tumor size [using the commonly accepted formula: Tumor Volume (mm³)=(a×b²/2); where 'a' represents the length, and 'b' the width of the tumor as determined by caliper measurements], were monitored twice weekly throughout the study. A sustained body weight loss greater than 15% of the initial body weight was considered as clinical toxicity, with the animal removed from the study and sacrificed. Time-course of tumor growth is expressed as median values, or can be normalized to initial tumor volume on the day treatment started and expressed as mean±standard error of the mean (SEM) (5 animals per group). For pre-established tumors, relative tumor volumes can be calculated for each mouse (treated tumor volume/tumor volume on day 0) and expressed as mean±SEM for each treatment group. Statistical significance is indicated by one-sided p-values from Wilcoxon-Mann-Whitney analysis (Wilcoxon rank sum test) and p<0.05 is considered as statistically significant. Treatment/control (T/C) ratios are calculated based on final relative tumor volumes, using the NCI criteria on day 6 and 10 (day 1=start of treatment, once mice have been randomized and assigned to the appropriate treatment groups). The effective criteria for T/C ratios is 42%.

TABLE 10

% T/C at day 6 and day 10 after start dosing

| Comp. No. | % T/C day 6 | % T/C day 10 |
| --- | --- | --- |
| 6 | 105 | 99 |
| 12 | 64 | 71 |
| 19 | 57 | 40 |
| 2 | 14 | −0.23 |
| 5 | 103 | 67 |
| 22 | 40 | 55 |
| 15 | 53 | 88 |
| 18 | 9 | −3 |
| 21 | 102 | 95 |
| 9 | 145 | 113 |
| 11 | 72 | 79 |
| 4 | 77 | 129 |
| 10 | 96 | 71 |
| 16 | 63 | 64 |
| 23 | 72 | 95 |
| 1 | 17 | 8 |
| 27 | 193 | 22 |
| 24 | 60 | 1 |
| 31 | 179 | 1 |
| 26 | 354 | −11 |
| 30 | −61 | −10 |
| 29 | −196 | −13 |
| 28 | −280 | −10 |
| 25 | 330 | −3 |

D. Composition Example: Film-coated Tablets

Preparation of Tablet Core

A mixture of 100 g of a compound of formula (I), 570 g lactose and 200 g starch is mixed well and thereafter humidified with a solution of 5 g sodium dodecyl sulphate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol, 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:
1. A compound of formula (I)

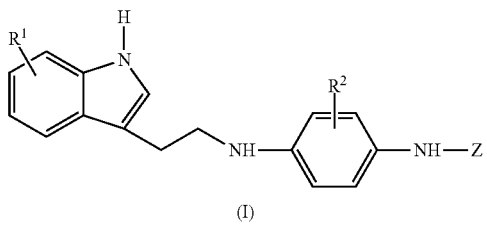
(I)

including any stereochemically isomeric form thereof, wherein
$R^1$ is hydroxy$C_{1-6}$alkyl or $C_{2-6}$alkenyl; provided that the $R^1$ substituent is placed in position 6 or 7 of the indole moiety;
$R^2$ is hydrogen or $C_{1-4}$alkyl;
Z is a radical selected from

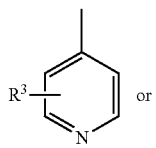
(z-1)

or

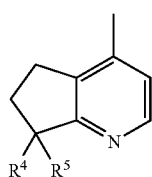
(z-2)

$R^3$ is hydrogen or hydroxy$C_{1-4}$alkyl;
$R^4$ is hydroxy or $C_{1-4}$alkyloxy;
$R^5$ is hydrogen or $C_{1-4}$alkyl; or
$R^4$ and $R^5$ are taken together to form oxo;
a pharmaceutically acceptable salt thereof or a solvate thereof.

2. A compound as claimed in claim 1 wherein the compound has the following formula

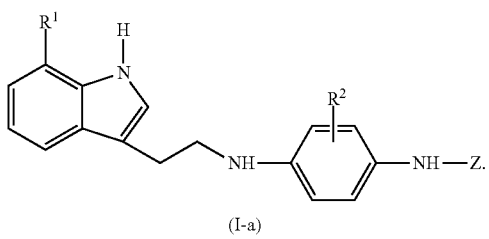
(I-a)

3. A compound as claimed in claim 2 wherein $R^1$ is hydroxy$C_{1-6}$alkyl.
4. A compound as claimed in claim 3 wherein $R^2$ is $C_{1-4}$alkyl.
5. A compound according to claim 4 wherein Z is a radical of formula (z-1).
6. A compound as claimed in claim 4 wherein Z is a radical of formula (z-2).
7. A compound as claimed in claim 6 wherein $R^4$ is hydroxyl and $R^5$ is hydrogen.

8. A compound as claimed in claim 6 wherein $R^4$ is hydroxyl and $R^5$ is $C_{1-4}$alkyl.
9. A compound as claimed in claim 1 wherein the compound is an enantiomer having the formula

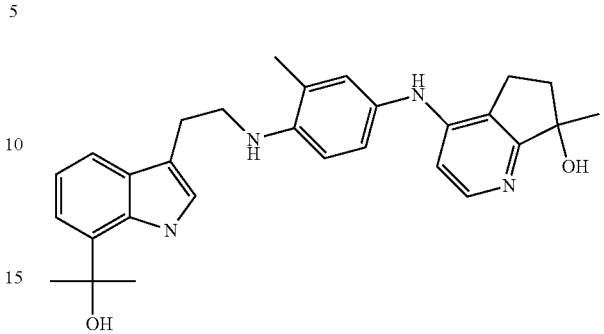

and having a levorotatory rotation measured with light at the wavelength of the D-line of sodium (589 nm) at a temperature of 20° C. and a cell pathlength of 1 dm in chloroform at a concentration of 8.59 mg/ml; or
a pharmaceutically acceptable salt thereof or a solvate thereof.

10. A compound as claimed in claim 1 wherein the compound is an enantiomer having the formula

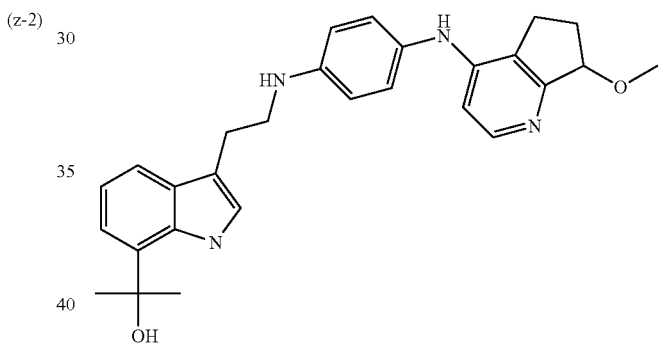

and having a dextrorotatory rotation measured with light at the wavelength of the D-line of sodium (589 nm) at a temperature of 20° C. and a cell pathlength of 1 dm in methanol at a concentration of 10.33 mg/ml; or
a pharmaceutically acceptable salt thereof or a solvate thereof.

11. A compound according to claim 10 for use as a medicine.
12. A pharmaceutical composition comprising a pharmaceutically acceptable carrier and as an active ingredient a therapeutically effective amount of a compound as claimed in claim 10.
13. A combination of one or more anti-cancer agents and a compound as claimed in claim 10.
14. A process for preparing a compound as claimed in claim 1, comprising
a) reacting an intermediate of formula (II) with an intermediate of formula (III) wherein $W_1$ is a suitable leaving group, in a reaction-inert solvent optionally in the presence of an appropriate base or reacting an intermediate of formula (II) with an intermediate of formula (III) wherein $W_1$ is a suitable leaving group in the presence of a suitable catalyst, a suitable ligand, a suitable base and a suitable solvent

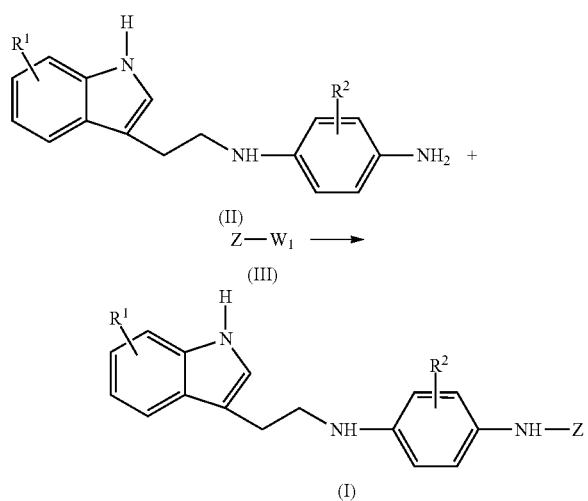

(II) + Z—W₁ ⟶ (III)

with $R^1$, $R^2$ and Z as defined in claim 1;

b) reducing the corresponding carbonyl derivative of formula (IV) in the presence of a suitable reducing agent and a suitable solvent,

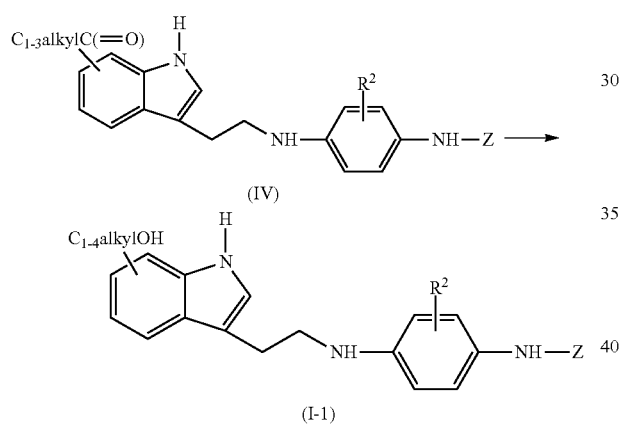

with $R^2$ and Z as defined in claim 1;

c) reducing the corresponding ester derivative of formula (V) wherein $R^x$ represents —$C_{1-3}$alkylC(=O)O$C_{1-4}$alkyl, in the presence of a suitable reducing agent and a suitable solvent,

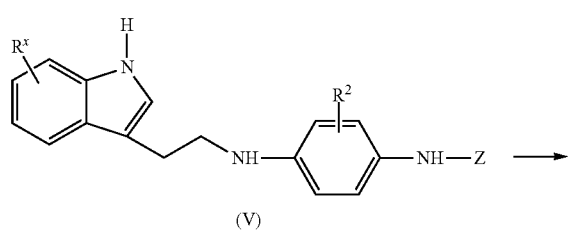

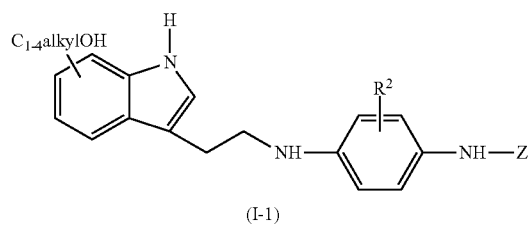

with $R^2$ and Z as defined in claim 1;

d) hydrolysing an intermediate of formula (VI) with a suitable base in the presence of a suitable solvent,

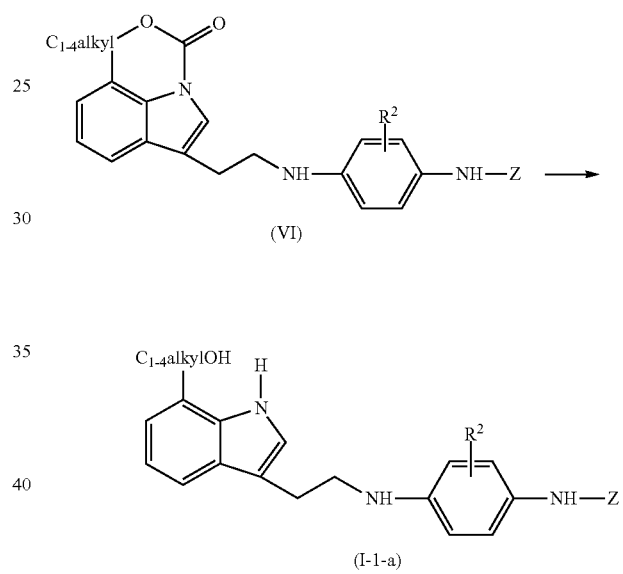

with $R^2$ and Z as defined in claim 1;

or, if desired, converting compounds of formula (I) into each other following art-known transformations, and further, if desired, converting the compounds of formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; or, if desired, preparing stereochemically isomeric forms or solvates thereof.

\* \* \* \* \*